(12) United States Patent
Rau et al.

(10) Patent No.: US 9,913,912 B2
(45) Date of Patent: Mar. 13, 2018

(54) CARRIER-LINKED PROSTANOID PRODRUGS

(71) Applicant: Ascendis Pharma A/S, Hellerup (DK)

(72) Inventors: Harald Rau, Dossenheim (DE); Guillaume Maitro, Mannheim (DE); Ulrich Hersel, Heidelberg (DE); Oliver Keil, Berlin (DE); Thomas Wegge, Heidelberg (DE)

(73) Assignee: Ascendis Pharma A/S, Hellerup (DE)

( * ) Notice: Subject to any disclaimer, the term of this patent is extended or adjusted under 35 U.S.C. 154(b) by 0 days.

(21) Appl. No.: 14/650,175

(22) PCT Filed: Dec. 6, 2013

(86) PCT No.: PCT/EP2013/075761
§ 371 (c)(1),
(2) Date: Jun. 5, 2015

(87) PCT Pub. No.: WO2014/086961
PCT Pub. Date: Jun. 12, 2014

(65) Prior Publication Data
US 2015/0306239 A1 Oct. 29, 2015

(30) Foreign Application Priority Data
Dec. 7, 2012 (EP) .................... 12196052

(51) Int. Cl.
*A61K 47/60* (2017.01)
*A61K 31/5585* (2006.01)
*A61K 47/48* (2006.01)

(52) U.S. Cl.
CPC .... *A61K 47/48215* (2013.01); *A61K 31/5585* (2013.01); *A61K 47/48038* (2013.01)

(58) Field of Classification Search
None
See application file for complete search history.

(56) References Cited

U.S. PATENT DOCUMENTS 6,242,482 B1  6/2001  Shorr et al.

FOREIGN PATENT DOCUMENTS

| EP | 0369463 | 5/1990 |
|---|---|---|
| WO | WO 06/003014 | 1/2006 |
| WO | WO 08/094659 | 8/2008 |
| WO | WO 09/133137 | 11/2009 |
| WO | WO 11/012715 | 2/2011 |
| WO | WO 12/139164 | 10/2012 |
| WO | WO 13/024047 | 2/2013 |
| WO | WO 13/024048 | 2/2013 |
| WO | WO 13/024049 | 2/2013 |
| WO | WO 13/024052 | 2/2013 |
| WO | WO 14/056926 | 4/2014 |

OTHER PUBLICATIONS

Pan, Huaizhong. Journal of Drug Targeting 14(6). (2006) 425-435.*
"Medicament." Merriam-Webster.com. Merriam-Webster, n.d. Web. Oct. 12, 2016.*
Center for Disease Control and Prevention. Division for Heart Disease and Stroke Prevention: Pulmonary Hypertension Fact Sheet. (2014) Web: <https://www.cdc.gov/dhdsp/data_statistics/fact_sheets/fs_pulmonary_hypertension.htm>.*
Barst, Robyn. Journal of the American College of Cardiology. 41(12) (2003) 2119-2125.*
Pedersen, et al. "Prostaglandin phospholipid conjugates with unusual biophysical and cytotoxic properties", Bioorganic & Medicinal Chemistry Letters, 2010 4456-4458, vol. 20.
Thomas A. Walker, "Separation of Beraprost sodium isomers using different cyclodextrin stationary phases" Journal of Chromatography, (1993) pp. 97-103, vol. 633.
International Preliminary Report on Patentability corresponding with PCT/EP2013/075761, dated Jun. 5, 2015, 7 pages.

* cited by examiner

*Primary Examiner* — Deepak R Rao
*Assistant Examiner* — Laura M Daniel
(74) *Attorney, Agent, or Firm* — Haug Partners LLP

(57) ABSTRACT

The present invention relates to carrier-linked prostanoid prodrugs of formula (I) $Z^1-(X^0-L^0-PG^0)_y$, (I), wherein $Z^1$, $X^0$, $L^0$, $PG^0$ and y have the meaning as indicated in the description and claims; pharmaceutically acceptable salts thereof and pharmaceutical compositions comprising the same. It further relates to their use as medicaments, especially for treating, controlling, delaying or preventing pulmonary arterial hypertension.

21 Claims, No Drawings

CARRIER-LINKED PROSTANOID PRODRUGS

The present application claims priority from PCT Patent Application No. PCT/EP2013/075761 filed on Dec. 6, 2013, which claims priority from European Patent Application No. EP 12196052.0 filed on Dec. 7, 2012, the disclosures of which are incorporated herein by reference in their entirety.

The present invention relates to carrier-linked prostanoid prodrugs, pharmaceutically acceptable salts thereof and pharmaceutical compositions comprising the same. It further relates to their use as medicaments, especially for treating, controlling, delaying or preventing pulmonary arterial hypertension.

Pulmonary arterial hypertension (PAH) is an increase in blood pressure in the pulmonary artery, pulmonary vein, or pulmonary capillaries, leading to shortness of breath, dizziness, fainting, and other symptoms, all of which are exacerbated by exertion. PAH can be a severe disease with a markedly decreased exercise tolerance and heart failure. It is an orphan disease with an incidence of about 2-3 per million per year and a prevalence of about 15 per million. Median survival of patients with untreated PAH is in the range of 2-3 years from time of diagnosis, with the cause of death usually being right ventricular failure.

Pulmonary arterial hypertension involves the vasoconstriction or tightening of blood vessels connected to and within the lungs. Over time, fibrosis causes the affected blood vessels to become both stiffer and thicker which further increases the blood pressure within the lungs and impairs their blood flow. In addition, the increased workload of the heart causes hypertrophy of the right ventricle which ultimately causes right heart failure. As the blood flowing through the lungs decreases, the left side of the heart receives less blood and thus oxygen supply is below the required level, especially during physical activity.

A number of agents have been introduced for the treatment of PAH of which prostanoids, in particular prostacyclins and prostaglandins, are commonly considered to be the most effective. One prostacyclin is Epoprostenol which is a synthetic prostacyclin and marketed as Flolan® (GlaxoSmithKline). It is given to patients via continuous infusion and requires a semi-permanent central venous catheter which can cause sepsis and thrombosis. Flolan® is unstable, and therefore has to be kept on ice during administration. Since it has a half-life of only 3 to 5 minutes, the infusion has to be continuous night and day and any interruption can be fatal. Thus, treatment of PAH with Flolan® is a huge burden for the patient.

Another prostacyclin, Iloprost (Ilomedin) which is marketed as Ventavis® (Bayer), was the only inhaled form of prostacyclin approved for use in the US and Europe, until the inhaled form of treprostinil was approved by the FDA in July 2009 which is marketed under the trade name TYVASO® (United Therapeutics).

Both prostacyclins and prostaglandins are subclasses of prostanoids. The prostacylins most commonly used in the treatment of PAH are treprostinil, beraprost, cicaprost, epoprostenol, iloprost, and isocarbacyclin, and the prostaglandin most commonly used in the treatment of PAH is alprostadil.

All prostaglandins and prostacyclins have short half-lives in common. Therefore, the treatment of PAH with one or more of these compounds requires high application frequencies. This makes the maintenance of therapeutically effective levels not only inconvenient for the patient, but also technically difficult.

International application WO2013/024052A1 already teaches prodrugs of treprostinil which release treprostinil over an extended period from a depot.

Therefore, there exists a need to provide a more efficacious and/or more comfortable treatment for patients with prostanoides except treprostinil.

This object is achieved with a carrier-linked prostanoid prodrug of formula (I):

$$Z^1-(X^0-L^0-PG^0)_y \quad (I),$$

wherein each $PG^0$ is independently a prostanoid moiety except treprostinil which is attached to $L^0$ through a hydroxyl or carboxyl group of $PG^0$;

each $L^0$ is independently —(C=O)— or —O—(C=O)—, if $PG^0$ is attached to $L^0$ through a hydroxyl group; and —O—, if $PG^0$ is attached to $L^0$ through a carboxyl group;

y is an integer ranging of from 1 to 64;

each $X^0$ is independently $(X^{0B})_{m1}$—$(X^{0A})_{m2}$;

m1 and m2 are independently 0; or 1;

each $X^{0A}$ is independently $T^0$;

each $X^{0B}$ is independently a linear or branched $C_{1-50}$ alkyl, $C_{2-50}$ alkenyl or $C_{2-50}$ alkynyl which is optionally one or more times interrupted by phenyl, naphthyl, azulenyl, indenyl, indanyl, $C_{3-7}$ cycloalkyl, 3- to 7-membered heterocyclyl, or 8- to 11-membered heterobicyclyl; and/or which is optionally interrupted by one or more of the following bivalent groups

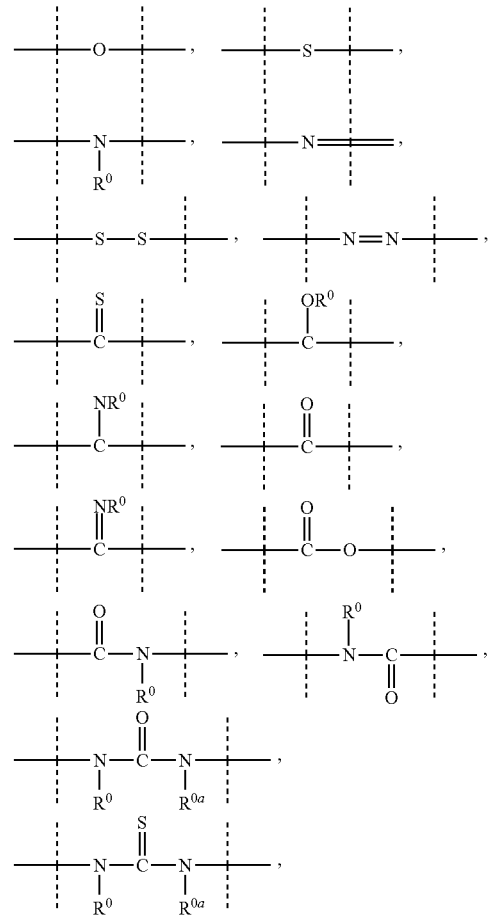

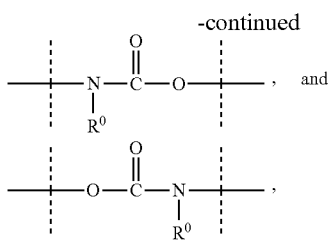

wherein
dashed lines indicate attachment points, and
$R^0$ and $R^{0a}$ are independently of each other selected from H and $C_{1-6}$ alkyl;

which $X^{0B}$ is optionally substituted with one or more $R^0$, which are the same or different;

$R^1$ is halogen, $C_{1-6}$ alkyl, CN, $C(O)R^2$, $C(O)OR^2$, oxo (=O), $OR^2$, $C(O)R^2$, $C(O)N(R^2R^{2a})$, $S(O)_2N(R^2R^{2a})$, $S(O)N(R^2R^{2a})$, $S(O)_2R^2$, $S(O)R^2$, $N(R^2)S(O)_2N(R^{2a}R^{2b})$, $SR^2$, $N(R^2R^{2a})$, $NO_2$, $OC(O)R^2$, $N(R^2)C(O)R^{2a}$, $N(R^2)SO_2R^{2a}$, $N(R^2)S(O)R^{2a}$, $N(R^2)C(O)N(R^{2a}R^{2b})$, $N(R^2)C(O)OR^{2a}$, $OC(O)N(R^2R^{2a})$, or $T^0$;

$R^2$, $R^{2a}$, $R^{2b}$ are independently H, $T^0$, $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl are optionally substituted with one or more $R^3$, which are the same or different;

$R^3$ is halogen, CN, $C(O)R^4$, $C(O)OR^4$, $OR^4$, $C(O)R^4$, $C(O)N(R^4R^{4a})$, $S(O)_2N(R^4R^{4a})$, $S(O)N(R^4R^{4a})$, $S(O)_2R^4$, $S(O)R^4$, $N(R^4)S(O)_2N(R^{4a}R^{4b})$, $SR^4$, $N(R^4R^{4a})$, $NO_2$, $OC(O)R^4$, $N(R^4)C(O)R^{4a}$, $N(R^4)SO_2R^{4a}$, $N(R^4)S(O)R^{4a}$, $N(R^4)C(O)N(R^{4a}R^{4b})$, $N(R^4)C(O)OR^{4a}$, or $OC(O)N(R^4R^{4a})$;

$R^4$, $R^{4a}$, $R^{4b}$ are independently H, $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl are optionally substituted with one or more halogen, which are the same or different;

$T^0$ is phenyl, naphthyl, azulenyl, indenyl, indanyl, $C_{3-10}$ cycloalkyl, 3 to 7 membered heterocyclyl, or 8- to 11-membered heterobicyclyl; wherein $T^0$ is optionally substituted with one or more $R^5$, which are the same or different;

$R^5$ is halogen, CN, $COOR^6$, $OR^6$, $C(O)R^6$, $C(O)N(R^6R^{6a})$, $S(O)_2N(R^6R^{6a})$, $S(O)N(R^6R^{6a})$, $S(O)_2R^6$, $S(O)R^6$, $N(R^6)S(O)_2N(R^{6a}R^{6b})$, $SR^6$, $N(R^6R^{6a})$, $NO_2$, $OC(O)R^6$, $N(R^6)C(O)R^{6a}$, $N(R^6)S(O)_2R^{6a}$, $N(R^6)S(O)R^{6a}$, $N(R^6)C(O)OR^{6a}$, $N(R^6)C(O)N(R^{6a}R^{6b})$, $OC(O)N(R^6R^{6a})$, oxo (=O) where the ring is at least partially saturated, $C_{1-6}$ alkyl, $C_{2-6}$ alkenyl, or $C_{2-6}$ alkynyl; wherein said $C_{1-6}$ alkyl, $C_{2-6}$ alkenyl, and $C_{2-6}$ alkynyl are optionally substituted with one or more $R^7$, which are the same or different;

$R^6$, $R^{6a}$, $R^{6b}$ are independently H, $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl are optionally substituted with one or more $R^8$, which are the same of different;

$R^7$ and $R^8$ are independently halogen, CN, $C(O)R^9$, $C(O)OR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, or $OC(O)N(R^9R^{9a})$;

$R^9$, $R^{9a}$, $R^{9b}$ are independently H, $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl are optionally substituted with one or more halogen, which are the same of different;

$Z^1$ is a carrier comprising a covalently bound polymer, preferably a pharmaceutically acceptable polymer, or a covalently bound $C_{10-24}$ fatty acid;

wherein the carrier is covalently attached to a moiety $X^0$, provided that at least one of m1, m2 is 1 and wherein the carrier is covalently attached to $L^0$ in case m1, m2=0;

or a pharmaceutically acceptable salt thereof.

It was surprisingly found that such carrier-linked prostanoid prodrugs can be used to obtain longer-lasting dosage forms of prostanoids which at least partially overcome the above mentioned shortcomings.

Certain structures based on treprostinil are disclosed in prior art document WO2013/024052. Treprostinil has the following structure:

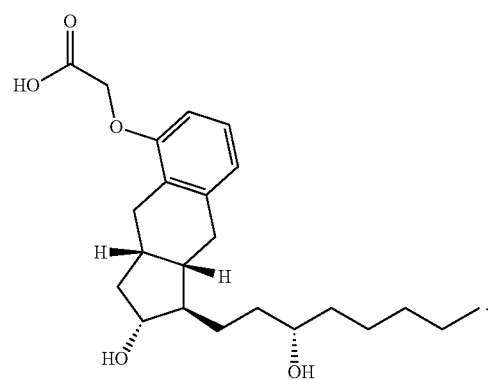 [SMILES: CCCCC[C@H](O)CC[C@@H]1[C@H]2Cc3cccc(OCC(=O)O)c3C[C@H]2C[C@H]1O]

Within the present invention the terms are used having the meaning as follows.

As used herein, the term "prostanoid" means prostaglandins and prostacyclins. Preferred prostanoids are beraprost, cicaprost, epoprostenol, iloprost, isocarbycyclin and alprostadil.

The term "beraprost" as used herein has the following general structure:

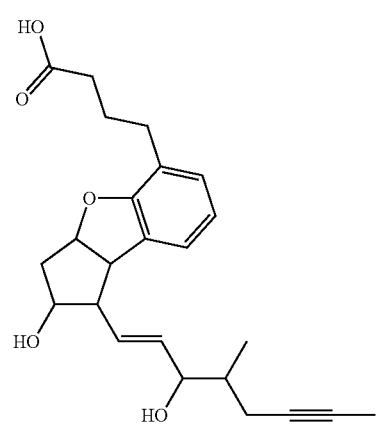 [SMILES: CC#CCC(C)C(O)/C=C/C1C(O)CC2Oc3c(CCCC(=O)O)cccc3C21]

which has six stereocenters. Preferably, the term beraprost has the following stereochemistry:

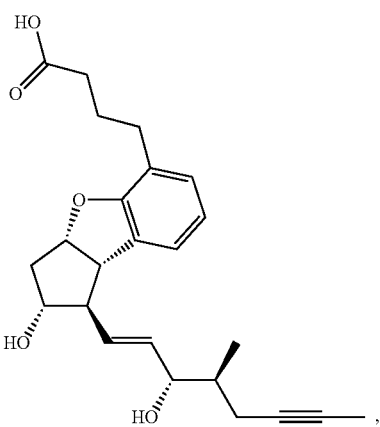 [SMILES: CC#CC[C@H](C)[C@H](O)/C=C/[C@@H]1[C@H]2c3cccc(CCCC(=O)O)c3O[C@H]2C[C@H]1O]

but also other stereochemistries and isomer mixtures are pharmaceutically active and used in the treatment of PAH and are also included by the term beraprost. This refers in particular to the 314d and 315d isomer and to a mixture of the 314d and 315d isomers, the structures of which are shown, e.g. in Journal of Chromatography A, Volume 633, Issues 1-2, 24 Feb. 1993, Pages 97-103.

The term "cicaprost" as used herein has the following structure:

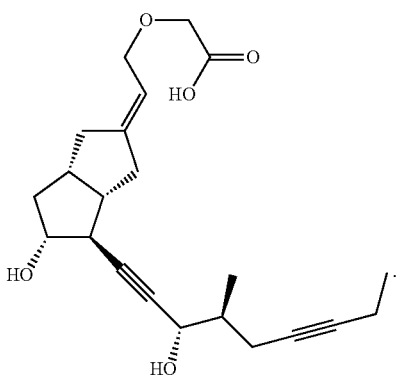 [SMILES: CCC#CC[C@H](C)[C@H](O)C#C[C@@H]1[C@H]2C/C(=C/COCC(=O)O)C[C@H]2C[C@H]1O]

The term "epoprostenol" as used herein has the following structure:

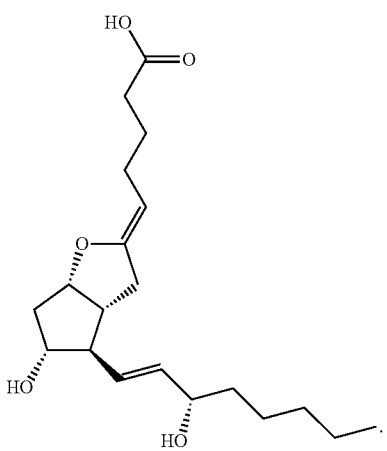 [SMILES: CCCCC[C@H](O)/C=C/[C@@H]1[C@H]2C/C(=C/CCCC(=O)O)O[C@H]2C[C@H]1O]

The term "iloprost" as used herein has the following structure:

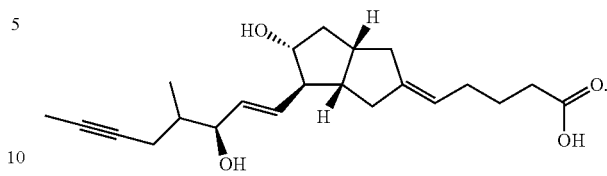

The term "isocarbacyclin" as used herein has the following structure:

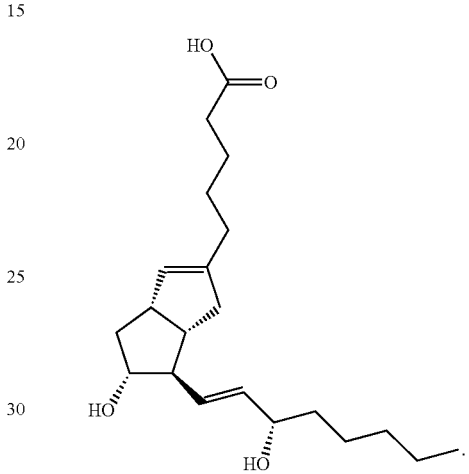

The term "alprostadil" as used herein has the following structure:

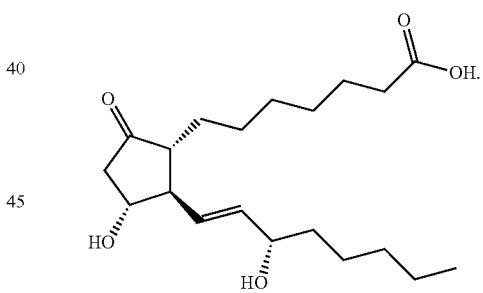

The terms "drug" and "biologically active moiety" mean any substance which can affect any physical or biochemical properties of a biological organism, including but not limited to viruses, bacteria, fungi, plants, animals, and humans. In particular, as used herein, the terms refer to prostanoids.

As used herein, the terms "moiety" or "in bound form" mean a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—¦" or "-¦X-¦", whereas each "¦" indicates attachment to another moiety. Accordingly, a biologically active moiety comprised in a prodrug is released from said prodrug as a drug, i.e. the carrier-linked prostanoid prodrug of the present invention comprises one or more prostanoid moiety/moieties, which are released from the prodrug as a prostanoid drug or prostanoid in its free form.

"Free form" of a drug such as a prostanoid refers to the drug in its unmodified, pharmacologically active form, such as after being released from a carrier-linked prodrug.

As used herein, the term "prodrug" means a compound that undergoes biotransformation before exhibiting its pharmacological effects. Prodrugs can thus be viewed as biologically active moieties connected to specialized non-toxic protective groups used in a reversible manner to alter or to eliminate undesirable properties in the parent molecule. This also includes the enhancement of desirable properties in the drug and the suppression of undesirable properties.

As used herein, the term "carrier-linked prodrug" means a prodrug that contains a temporary linkage of a biologically active moiety with a reversible carrier group that produces improved physicochemical or pharmacokinetic properties and that can be easily removed in vivo, usually by a hydrolytic cleavage. Such carrier-linked prodrug thus comprises at least a biologically active moiety, which is attached to a carrier group through a reversible prodrug linker. Said reversible prodrug linker is on its one end attached to a biologically active moiety through a reversible linkage and on another end is attached to the carrier through a permanent linkage.

The reversible linkage between the reversible prodrug linker and the biologically active moiety is non-enzymatically hydrolytically degradable, i.e. cleavable, under physiological conditions (aqueous buffer at pH 7.4, 37° C.) with half-lives ranging from, for example, one hour to three months. On the other hand, stable or permanent linkages are typically non-cleavable permanent bonds, meaning that they have a half-life of at least six months under physiological conditions (aqueous buffer at pH 7.4, 37° C.).

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may for example also comprise functional groups or other moieties. Preferably, a polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. Preferably, a polymer has a molecular weight of at most 200 kDa, e.g. a molecular weight of at most 160 kDa, a molecular weight of at most 120 kDa, a molecular weight of at most 100 kDa.

As used herein, the term "polymeric" means a reagent or a moiety comprising one or more polymer(s).

The person skilled in the art understands that polymers do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "PEG-based" in relation to a moiety or reagent means that said moiety or reagent comprises at least 20% (w/w) ethylene glycol units ($-CH_2CH_2O-$), preferably, at least 50% (w/w) ethylene glycol units, more preferably at least 80% (w/w) ethylene glycol units, wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties, which other moieties are especially selected from the following substituents and linkages:

$C_{1-50}$ alkyl, $C_{2-50}$ alkenyl, $C_{2-50}$ alkynyl, $C_{3-10}$ cycloalkyl, 3- to 7-membered heterocyclyl, 8- to 11-membered heterobicyclyl, phenyl; naphthyl; indenyl; indanyl; and tetralinyl; and linkages selected from the group comprising

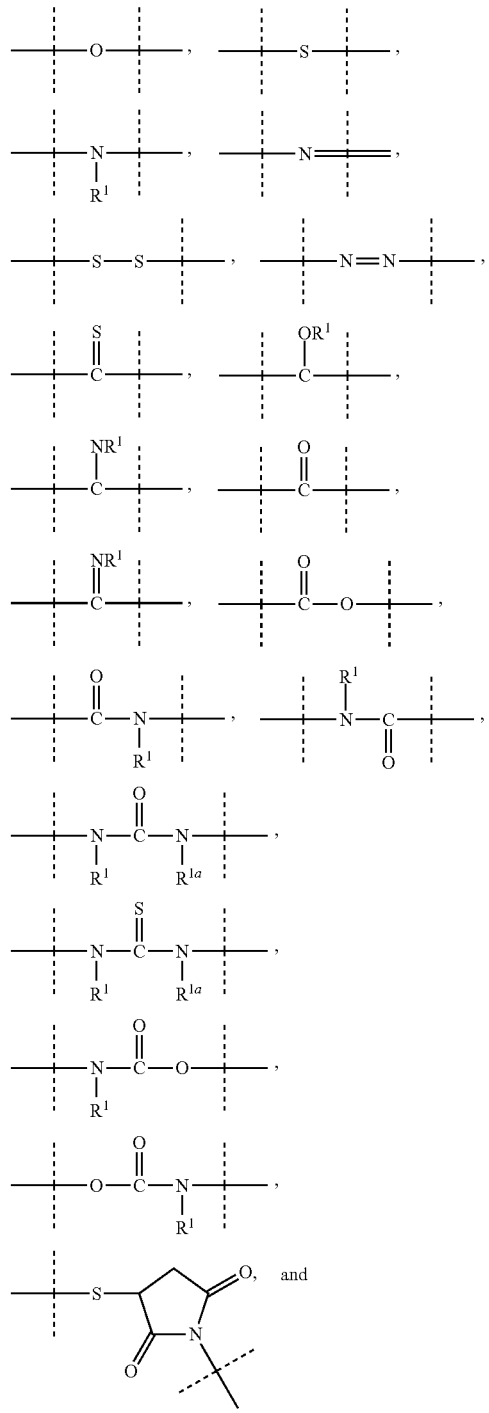

-continued

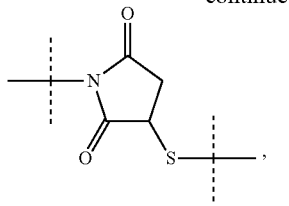

wherein
dashed lines indicate attachment points to the remainder of the moiety or reagent, and
$R^1$ and $R^{1a}$ are independently of each other selected from H and $C_{1-6}$ alkyl.

In a preferred embodiment the remaining weight percentage is at least partly propylene glycol (1,2-propane diol). In a further preferred embodiment, the propylene glycol may be arranged blockwise, alternating or may be randomly distributed within the moiety or reagent and preferably all propylene glycol units of said moiety or reagent are present in one block. In a further preferred embodiment ethylene glycol and propylene glycol are blockwise arranged such as to form a poloxamer.

The term "poloxamer" as used herein means nonionic triblock copolymers composed of a central hydrophobic chain of poly(propylene glycol) flanked by two hydrophilic chains of poly(ethylene glycol).

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

The term "terminus" refers to the last carbon atom or heteroatom of a linear or branched chain of carbon atoms and/or heteroatoms, i.e. "terminus" refers to a carbon or heteroatom which is connected to exactly one other carbon or heteroatom.

"Terminal/terminally" or "terminally connected" means that moieties are connected to the terminus or termini of another moiety.

"Pharmaceutical composition" or "composition" means a composition containing one or more drugs or prodrugs, and optionally one or more excipients, as well as any product which results, directly or indirectly, from combination, complexation or aggregation of any two or more of the excipients and/or the drug or prodrug, or from dissociation of one or more of the excipients and/or drug and/or prodrug, or from other types of reactions or interactions of one or more of the excipients and/or drug and/or prodrug. Accordingly, a pharmaceutical composition of the present invention encompasses any composition obtainable by admixing a carrier-linked prostanoid prodrug of the present invention and a pharmaceutically acceptable excipient.

The term "excipient" refers to a diluent, adjuvant, or vehicle with which the carrier-linked prostanoid prodrug is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These compositions can take the form of solutions, suspensions, emulsions, tablets, pills, capsules, powders, sustained-release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of prostanoid(s) in the form of at least one carrier-linked prostanoid prodrug of the present invention, preferably in purified form, together with a suitable amount of excipient so as to provide the form for proper administration to the patient. The formulation should suit the mode of administration.

The term "pharmaceutically acceptable" means approved by a regulatory agency such as the EMEA (Europe) and/or the FDA (US) and/or any other national regulatory agency for use in animals, preferably in humans.

"Dry composition" means that the pharmaceutical composition comprising carrier-linked prostanoid prodrug according to the present invention is provided in a dry form in a container. Suitable methods for drying are spray-drying and lyophilization (freeze-drying). Such dry composition of carrier-linked prostanoid prodrug has a residual water content of a maximum of 10%, preferably less than 5% and more preferably less than 2% (determined according to Karl Fischer). The preferred method of drying is lyophilization.

"Lyophilized composition" means that the pharmaceutical composition comprising carrier-linked prostanoid prodrug was first frozen and subsequently subjected to water reduction by means of reduced pressure. This terminology does not exclude additional drying steps which may occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

As used herein, the term "functional group" means a group of atoms which can react with other functional groups. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxy (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

If a functional group reacts with another functional group, the resulting chemical structure is referred to as "linkage". For example, the reaction of an amine functional group with a carboxyl functional group results in an amide linkage.

As used herein, the term "$C_{1-6}$ alkyl" alone or in combination means a straight-chain or branched alkyl group having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. The terms "$C_{1-10}$ alkyl", "$C_{1-25}$ alkyl" and "$C_{1-50}$ alkyl" are used accordingly and refer to a straight-chain or branched alkyl group having 1 to 10, 1 to 25 and 1 to 50 carbon atoms, respectively. One or more hydrogen atom(s) of a $C_{1-6}$ alkyl, $C_{1-10}$ alkyl, $C_{1-25}$ alkyl or $C_{1-50}$ alkyl may be replaced by a substituent as indicated herein.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —$CH=CH_2$, —$CH=CH$—$CH_3$, —$CH_2$—$CH=CH_2$, —$CH=CHCH_2$—$CH_3$ and —$CH=CH$—$CH=CH_2$. When two moieties of a molecule are linked by the $C_{2-6}$ alkenyl group, then an example for such $C_{2-6}$ alkenyl is —$CH=CH$—. The terms "$C_{2-10}$ alkenyl", "$C_{2-25}$ alkenyl" and "$C_{2-50}$ alkenyl" are used accordingly and refer to a straight-chain or branched hydrocarbon moiety comprising at least one carbon-carbon double bond having 2 to 10, 2 to 25 and 2 to 50 carbon atoms, respectively. Each hydrogen atom of a $C_{2-6}$ alkenyl group, $C_{2-10}$ alkenyl group, $C_{2-25}$ alkenyl and $C_{2-50}$ alkenyl group may be replaced by a substituent as indicated herein. Optionally, one or more triple bond(s) may occur.

As used herein, the term "$C_{2-6}$ alkynyl" alone or in combination means straight-chain or branched hydrocarbon residue comprising at least one carbon-carbon triple bond having 2 to 6 carbon atoms. If present at the end of a molecule, examples are —$C\equiv CH$, —$CH_2$—$C\equiv CH$, $CH_2$—$CH_2$—$C\equiv CH$ and $CH_2$—$C\equiv C$—$CH_3$. When two moieties of a molecule are linked by the alkynyl group, then an example is: —$C\equiv C$—. The terms "$C_{2-10}$ alkynyl", "$C_{2-25}$ alkynyl" and "$C_{2-50}$ alkynyl" are used accordingly and refer to a straight-chain or branched hydrocarbon residue comprising at least one carbon-carbon triple bond having 2 to 10, 2 to 25 and 2 to 50 carbon atoms, respectively. Each hydrogen atom of a $C_{2-6}$ alkynyl group, $C_{2-10}$ alkynly group, $C_{2-25}$ alkynly group or a $C_{2-50}$ alkynyl group may be replaced by a substituent as indicated herein. Optionally, one or more double bond(s) may occur.

As used herein, the term "$C_{3-7}$ cycloalkyl" means a cyclic alkyl chain having 3 to 7 carbon atoms, which may be saturated or at least partially unsaturated, e.g. cyclopropyl, cyclobutyl, cyclopentyl, cyclohexyl, cyclohexenyl, cycloheptyl, cyclooctyl. Each hydrogen atom of a cycloalkyl carbon may be replaced by a substituent as indicated herein. The term "$C_{3-7}$ cycloalkyl" also includes bridged bicycles like norbonane (norbonanyl) or norbonene (norbonenyl).

The term "$C_{3-10}$ cycloalkyl" is used accordingly and refers to a cyclic alkyl chain having 3 to 10 carbon atoms, which may be saturated or at least partially unsaturated.

"Halogen" means fluoro, chloro, bromo or iodo. It is generally preferred that halogen is fluoro or chloro.

"3- to 7-membered heterocyclyl" or "3- to 7-membered heterocycle" means a ring with 3, 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —$S(O)$—, —$S(O)_2$—), oxygen and nitrogen (including =$N(O)$—) and wherein the ring is linked to the rest of the molecule via a carbon or nitrogen atom (unsubstituted 3- to 7-membered heterocyclyl). For the sake of completeness it is indicated that in some embodiments of the present invention, 3- to 7-membered heterocyclyl has to fulfill additional requirements. Examples for a 3- to 7-membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfo lane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. Optionally, one or more hydrogen atom(s) of a 3- to 7-membered heterocyclyl may be replaced by a substituent.

"8- to 11-membered heterobicyclyl" or "8- to 11-membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —$S(O)$—, —$S(O)_2$—), oxygen and nitrogen (including =$N(O)$—) and wherein the ring is linked to the rest of the molecule via a carbon or nitrogen atom (unsubstituted 8- to 11-membered heterobicyclyl). Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 8- to 11-membered heterobicycle also includes spiro structures of two rings like 1,4-dioxa-8-azaspiro[4.5]decane or bridged heterocycles like 8-aza-bicyclo[3.2.1]octane.

The term "$C_{10-24}$ fatty acid" as used herein refers to a carboxylic acid with a linear or branched, preferably linear, carbon chain having 10, 11, 12, 13, 14, 15, 16, 17, 18, 19, 20, 21, 22, 23 or 24 carbon atoms, which is either saturated or partially or fully unsaturated.

The term "interrupted" means that within or at the respective end of a moiety or reagent is inserted an atom or a group of atoms as indicated herein. For example, if a moiety X is interrupted by the groups $Y^1$ and $Y^2$, then the interrupted moiety can have one of the following exemplary structures:

(a) $Y^1$—X—$Y^2$;
(b) $Y^1$—$Y^2$—X;
(c) X—$Y^1$—$Y^2$;

(d) $X^{01}$—$Y^1$—$X^{02}$—$Y^2$—$X^{03}$, wherein $X^{01}$, $X^{02}$, $X^{03}$ together are X; and (e) $X^{01}$—$Y^1$—$Y^2$—$X^{02}$, wherein $X^{01}$ and $X^{02}$ together are X.

If X in the example above is a $C_{20}$ alkyl then the sum of carbon atoms of $X^{01}$, $X^{02}$ and $X^{03}$ in case (d) or the sum of carbon atoms of $X^{01}$ and $X^{02}$ in case (e) is 20. Preferably, $Y^1$ and $Y^2$ are not adjacent to each other. In examples (b), (c) and (e) $Y^1$ and $Y^2$ are adjacent to each other. Accordingly, examples (a) and (d) are preferred structures for a moiety X which is interrupted by the groups $Y^1$ and $Y^2$.

The term "interrupted by one or more of the following bivalent groups" as used herein means that a moiety is preferably interrupted by 1 to 20 of said bivalent groups, more preferably by 1 to 15 of said bivalent groups, even more preferably by 1 to 10 of said bivalent groups and most preferably by 1 to 5 of said bivalent groups, wherein the bivalent groups may be the same or different.

The term "substituted" means that one or more —H atom(s) of a molecule or moiety are replaced by a different atom or a group of atoms, which are referred to as "substituent". Suitable substituents are selected from the group consisting of halogen; CN; COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

wherein

R$^9$, R$^{9a}$, R$^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; $C_{3-10}$ cycloalkyl; 4 to 7 membered heterocyclyl; or 8- to 11-membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12b}$)); OC(O)N(R$^{12}$R$^{12a}$); or $C_{1-6}$ alkyl, wherein $C_{1-6}$ alkyl is optionally substituted with one or more halogen, which are the same or different;

R$^{11}$, R$^{11a}$, R$^{12}$, R$^{12a}$, R$^{12b}$ are independently selected from the group consisting of H; or $C_{1-6}$ alkyl, wherein $C_{1-6}$ alkyl is optionally substituted with one or more halogen, which are the same or different.

In one embodiment R$^9$, R$^{9a}$, R$^{9b}$ may be independently of each other H.

In one embodiment R$^{10}$ is $C_{1-6}$ alkyl.

In one embodiment T is phenyl.

Preferably, a maximum of 6 —H atoms of a molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

Generally, the term "dashed line" which is used to indicate the connection of one moiety to another is different from a dashed bond which is used to indicate stereochemistry. The person skilled in the art will be able to distinguish between these two.

The term "water soluble" as in a "water-soluble carrier" is a carrier that is soluble in water at room temperature. Typically, a solution of a water-soluble carrier will transmit at least about 75%, more preferably at least about 95% of light, transmitted by the same solution after filtering. On a weight basis, a water-soluble carrier or parts thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble carrier or parts thereof is about 95% (by weight) soluble in water or completely soluble in water.

In general the term "comprise" or "comprising" also encompasses "consist of" or "consisting of".

The carrier-linked prostanoid prodrug according to the present invention comprises prostanoid biologically active moieties, which prostanoid biologically active moieties are preferably selected from the group comprising beraprost, cicaprost, epoprostenol, iloprost, isocarbacyclin and/or alprostadil in bound form. These prostanoids as such are drugs known to a person skilled in the art either in their pure form or as a pharmaceutically acceptable salt thereof.

As used herein a single carrier-linked prostanoid prodrug dose is given in mg and the concentration of a carrier-linked prostanoid prodrug in a pharmaceutical composition is given in mg/mL. As the prostanoid is administered in the form of a carrier-linked prostanoid prodrug, the concentration is based on quantitative release of free prostanoid drug from the prodrug. By methods well-known in the art, aliquots of a composition are subjected to prostanoid-releasing conditions (aqueous buffer pH 7.4, 37° C., or accelerated conditions at elevated pH), until no significant increase in prostanoid concentration is observed and the total amount of released prostanoid is determined.

In the present invention, the carrier-linked prostanoid prodrug or a pharmaceutically acceptable salt thereof does not contain prostanoid drug in its free form or as a pharmaceutically acceptable salt thereof, but in bound form. Prostanoid is bound via one of its functional groups, e.g. via a hydroxyl or carboxyl, to a moiety L$^0$ of formula (I). This means that the carrier-linked prostanoid prodrug according to the present invention contains prostanoid as a biologically active moiety. Due to the cleavage of the prostanoid moiety from the carrier-linked prostanoid prodrug when administered to a patient in need thereof, prostanoid is released either in its free form or as a pharmaceutically acceptable salt thereof. In other words, the carrier-linked prostanoid prodrug contains one or more moieties $PG^0$, which moiety $PG^0$ is each substituted with a moiety $L^0$, which in turn is covalently bound $X^0$ (provided that at least one of m1/m2 of formula (I) is 1) which covalently bound to the carrier $Z^1$.

Preferably, each moiety $PG^0$ is independently alprostadil, epoprostinil, iloprost, beraprost, isocarbacyclin or cicaprost in bound form. Preferably, all moieties $PG^0$ have the same structure. More preferably, $PG^0$ is beraprost, epoprostinil or iloprost in bound form, even more preferably, $PG^0$ is beraprost or epoprostinil in bound form and most preferably, $PG^0$ is beraprost in bound form.

Preferably, all moieties $L^0$ in formula (I) have the same structure. Even more preferably, $L^0$ of formula (I) is —(C=O)—.

Preferably, each moiety -$L^0$-$PG^0$ is independently selected from formulas (i-a), (i-b), (i-c), (i-d), (i-e), (ii-a), (ii-b), (ii-c), (ii-d), (ii-e), (iii-a), (iii-b), (iii-c), (iii-d), (iii-e), (iv-a), (iv-b), (iv-c), (iv-d), (iv-e), (v-a), (v-b), (v-c), (v-d), (v-e), (vi-a), (vi-b), (vi-c), (vi-d) or (vi-e):

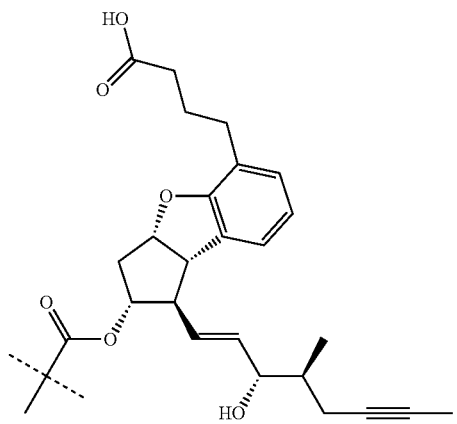

(i-c)

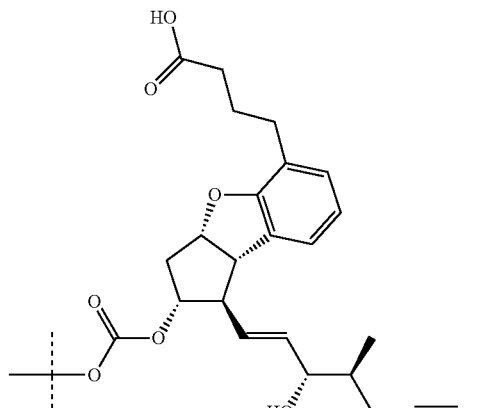

(i-a)

(i-d)

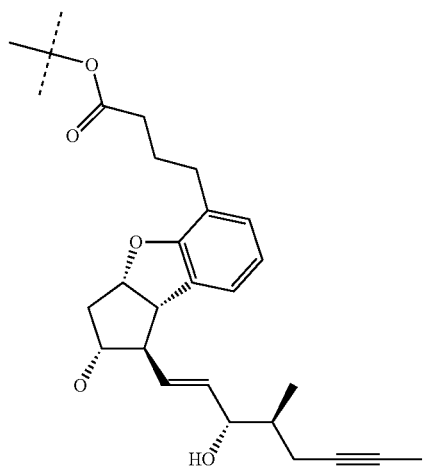

(i-b)

(i-e)

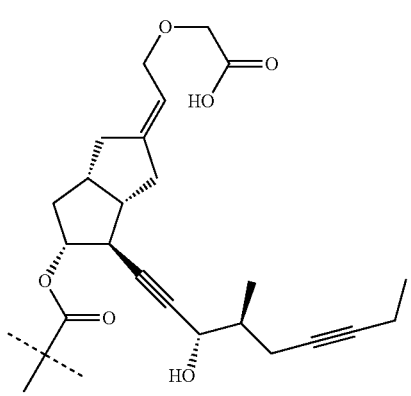
(ii-a)
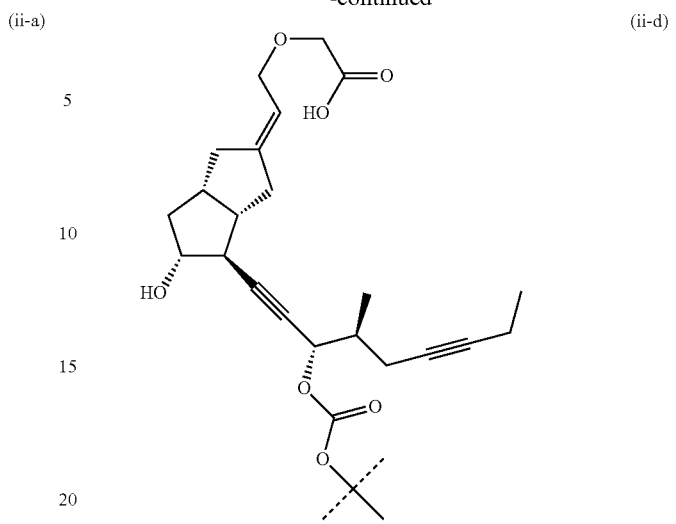
(ii-d)
(ii-b)
(ii-e)
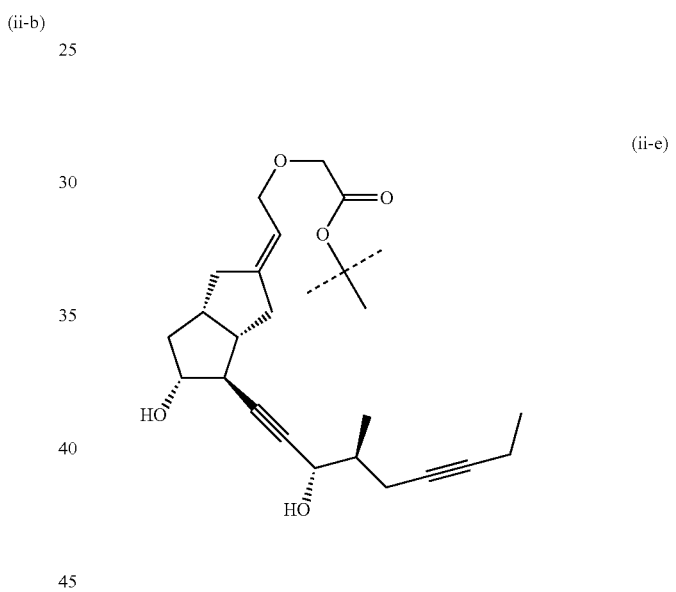
(ii-c)
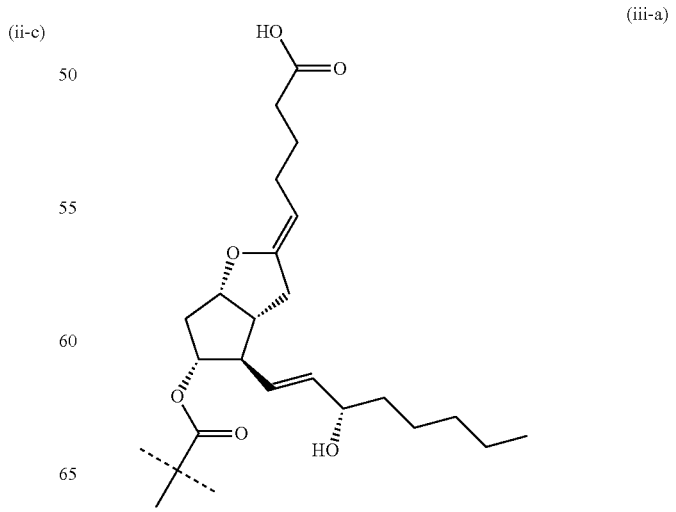
(iii-a)

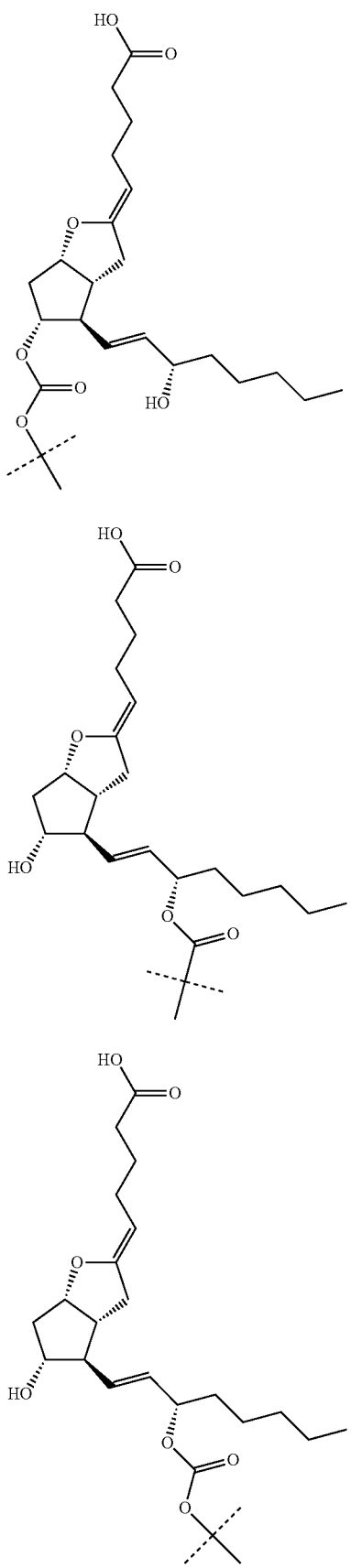
(iii-b)
(iii-c)
(iii-d)
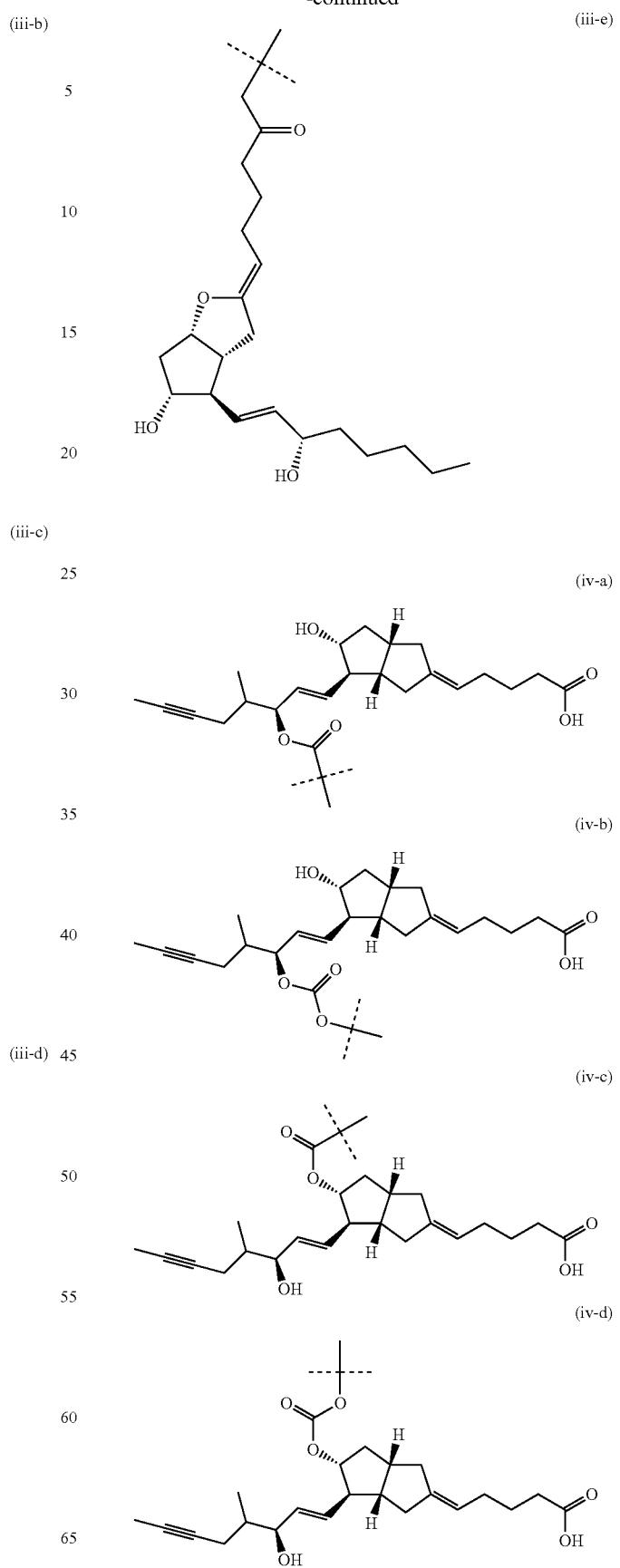
(iii-e)
(iv-a)
(iv-b)
(iv-c)
(iv-d)

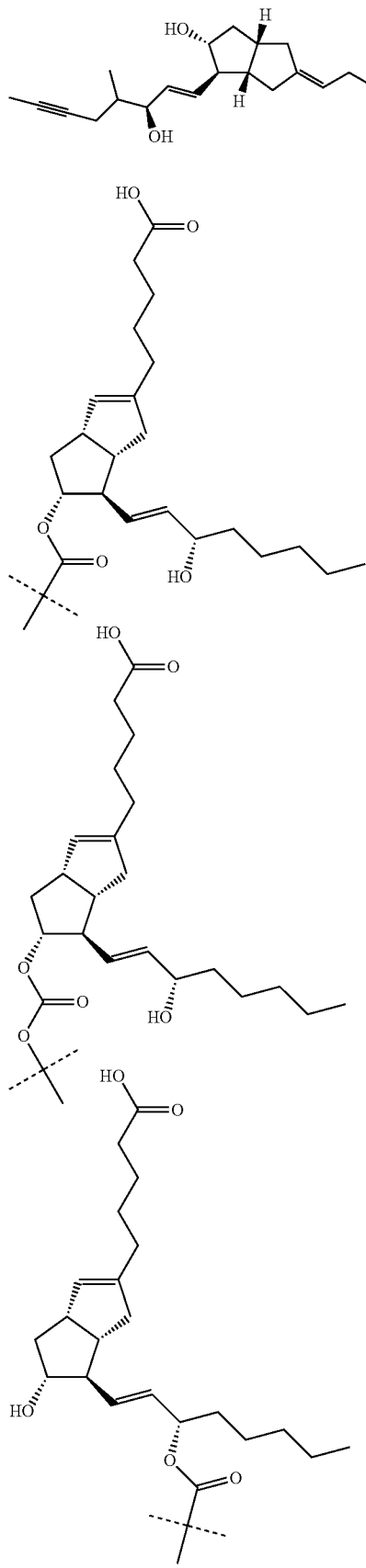
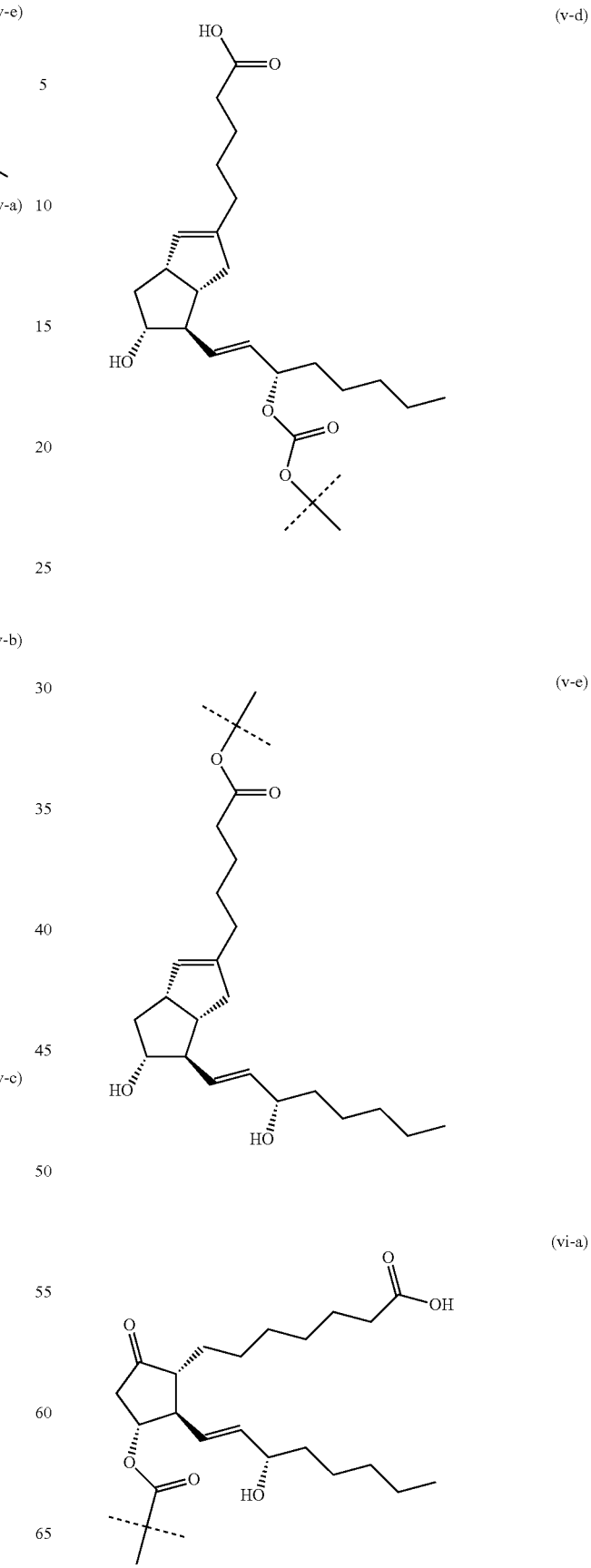

23
-continued (vi-b)
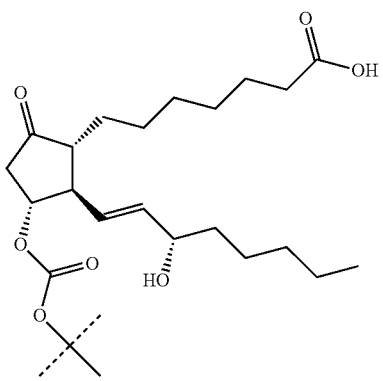

(vi-c)
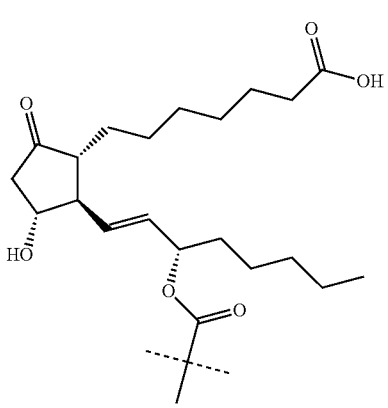

(vi-d)
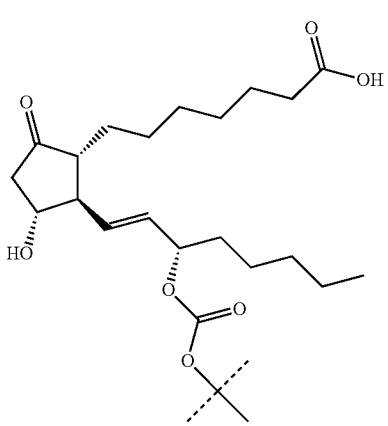

(vi-e)
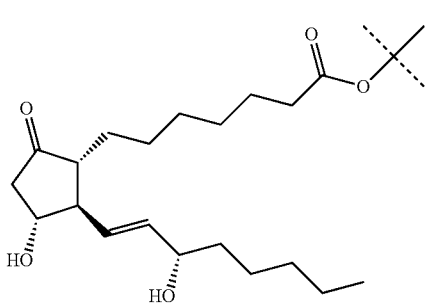

wherein
dashed lines indicate the attachment point.

Preferably, each moiety -L$^0$-PG$^0$ is independently selected from formulas (i-a), (i-c), (ii-a), (ii-c), (iii-a), (iii-c), (iv-a), (iv-c), (v-a), (v-c), (vi-a) or (vi-c). More preferably, each moiety -L$^0$-PG$^0$ is independently selected from formulas (i-a) or (i-c) and most preferably, each moiety -L$^0$-PG$^0$ is of formula (i-c).

In one embodiment y is 2, 4, 6, 8, 10, 12, 14, 16, 20, 24, 32, or 48. Preferably, y is 2, 4, 6, 8, 10 or 16; more preferably, y is 2, 4, 6 or 8 and most preferably, y is 4.

In a preferred embodiment both m1 and m2 are 1.

Preferably, all moieties $X^{0A}$ are the same. Preferably, $X^{0A}$ is phenyl, $C_{3-10}$ cycloalkyl, 3- to 7-membered heterocyclyl, or 8- to 11-membered heterobicyclyl, which is optionally substituted with one or more R$^5$, wherein R$^5$ is selected from halogen, CN, COOH, OH, C(O)H, C(O)NH$_2$, S(O)$_2$NH$_2$, S(O)NH$_2$, S(O)$_2$H, S(O)H, NHS(O)$_2$NH$_2$, SH, NH$_2$, NO$_2$, OC(O)H, NHC(O)H, NHS(O)$_2$H, NHS(O)H, NHC(O)OH, NHC(O)NH$_2$, OC(O)NH$_2$, oxo (=O) where the ring is at least partially saturated, $C_{1-6}$ alkyl, $C_{2-6}$ alkenyl, or $C_{2-6}$ alkynyl.

More preferably, $X^{0A}$ is of structure (Ia):

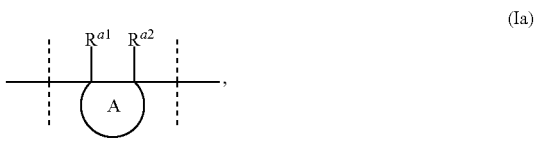
(Ia)

wherein dashed lines indicate attachment points,

R$^{a1}$ is selected from H, $C_{1-6}$ alkyl, $C_{2-6}$ alkenyl or $C_{2-6}$ alkynyl;

R$^{a2}$ is selected from H, $C_{1-6}$ alkyl, $C_{2-6}$ alkenyl or $C_{2-6}$ alkynyl;

A is selected from phenyl; naphthyl; indenyl; indanyl; tetralinyl; $C_{3-10}$ cycloalkyl; 3- to 7-membered heterocyclyl; and 8- to 11-membered heterobicyclyl, wherein A is optionally substituted.

Preferably, at least one of R$^{a1}$ and R$^{a2}$ of formula (Ia) is H; most preferably, both R$^{a1}$ and R$^{a2}$ are H.

Preferably, A is selected from $C_{3-10}$ cycloalkyl; 3- to 7-membered heterocyclyl; and 8- to 11-membered heterobicyclyl; most preferably, A is $C_{3-10}$ cycloalkyl.

Even more preferably, $X^{0A}$ is of structure (Iaa):

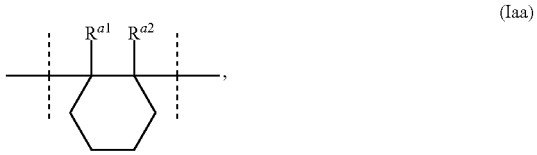
(Iaa)

wherein
dashed lines indicate attachment points,
R$^{a1}$ is selected from H, $C_{1-6}$ alkyl, $C_{2-6}$ alkenyl or $C_{2-6}$ alkynyl;
R$^{a2}$ is selected from H, $C_{1-6}$ alkyl, $C_{2-6}$ alkenyl or $C_{2-6}$ alkynyl;

More preferably, at least one of $R^{a1}$ and $R^{a2}$ of formula (Ia) or (Iaa) is H, even more preferably, both $R^{1a}$ and $R^{a2}$ are H.

Even more preferably, $X^{OA}$ is of structure (Iab):

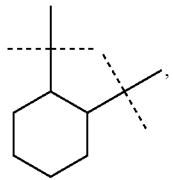

(Iab)

wherein
dashed lines indicate attachment points.

Most preferably, $X^{OA}$ is of structure (Iac):

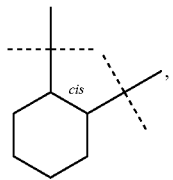

(Iac)

wherein
dashed lines indicate attachment points.

Preferably, all moieties $X^{OB}$ of formula (I) are the same.

Preferably, $X^{OB}$ is a linear or branched $C_{1-50}$ alkyl, $C_{2-50}$ alkenyl or $C_{2-50}$ alkinyl which is optionally one or more times interrupted by phenyl, naphthyl, azulenyl, indenyl, indanyl, $C_{3-7}$ cycloalkyl, 3- to 7-membered heterocyclyl, or 8- to 11-membered heterobicyclyl; and/or which is optionally interrupted by one or more of the following bivalent groups

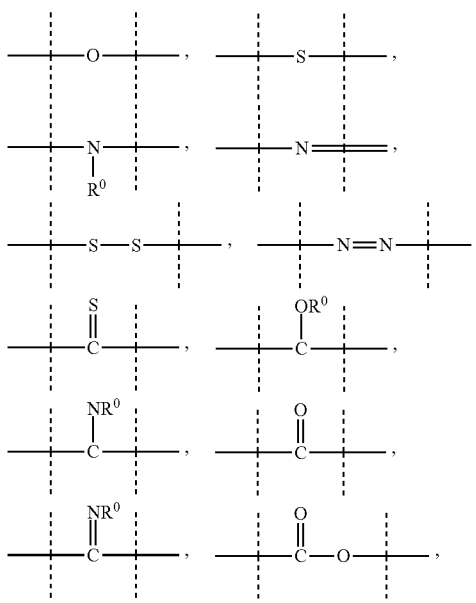

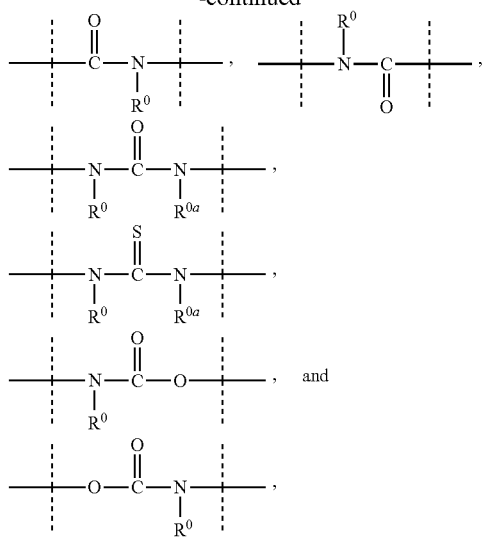

wherein
dashed lines indicate attachment points, and
$R^0$ and $R^{0a}$ are independently of each other selected from H and $C_{1-6}$ alkyl;
which $X^{OB}$ is optionally substituted with one or more $R^1$, which are the same or different, and wherein
$R^1$ is halogen, $C_{1-6}$ alkyl, CN, C(O)H, C(O)OH, OH, C(O)H, C(O)NH$_2$, S(O)$_2$NH$_2$, S(O)NH$_2$, S(O)$_2$H, S(O)H, NHS(O)$_2$NH$_2$, SH, NH$_2$, NO$_2$, OC(O)H, NHC(O)H, NHSO$_2$H, NHS(O)H, NHC(O)NH$_2$, NHC(O)OH, OC(O)NH$_2$, phenyl, naphthyl, azulenyl, indenyl, indanyl, $C_{3-7}$ cycloalkyl, 3- to 7-membered heterocyclyl, or 8- to 11-membered heterobicyclyl.

Preferably, $X^{OB}$ is substituted with 0, 1, 2, 3, or 4 moieties $R^0$, more preferably, $X^{OB}$ is substituted with 0, 1 or 2 moieties $R^0$, most preferably, $X^{OB}$ is substituted with 0 or 1 moiety $R^1$ and most preferably, $X^{OB}$ is unsubstituted, i.e. is substituted with 0 moieties $R^1$.

More preferably, $X^{OB}$ is a linear or branched $C_{1-50}$ alkyl, $C_{2-50}$ alkenyl or $C_{2-50}$ alkinyl which is optionally one or more times interrupted by one or more of the following bivalent groups

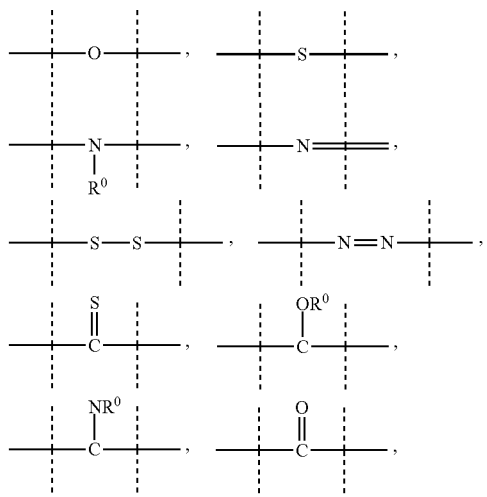

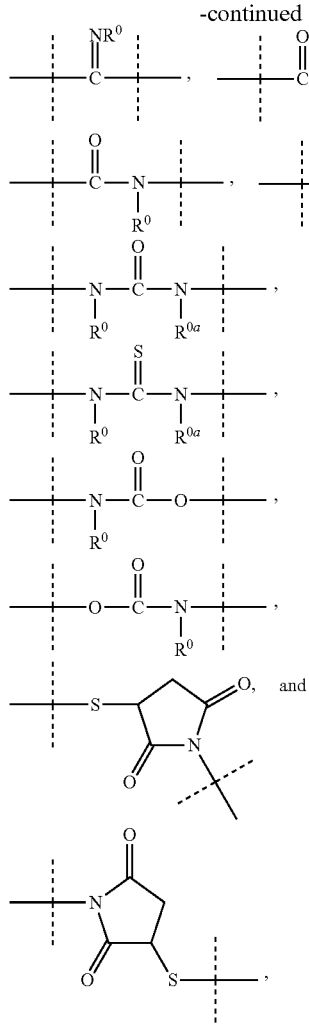

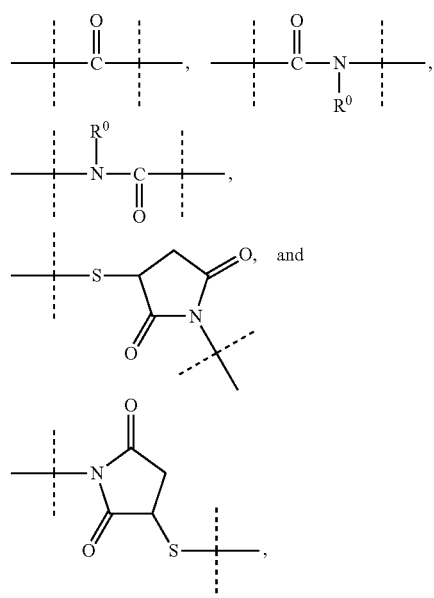

wherein dashed lines indicate the attachment point.

Even more preferably, $X^{OB}$ is of formula (Iba):

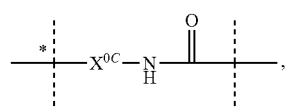

wherein the dashed line marked with the asterisk indicates attachment to $Z^1$ and the unmarked dashed line indicates attachment to $X^{OA}$; and $X^{OC}$ is a linear or branched $C_{1-25}$ alkyl, $C_{2-25}$ alkenyl or $C_{2-25}$ alkinyl which is optionally one or more times interrupted by one or more of the following bivalent groups

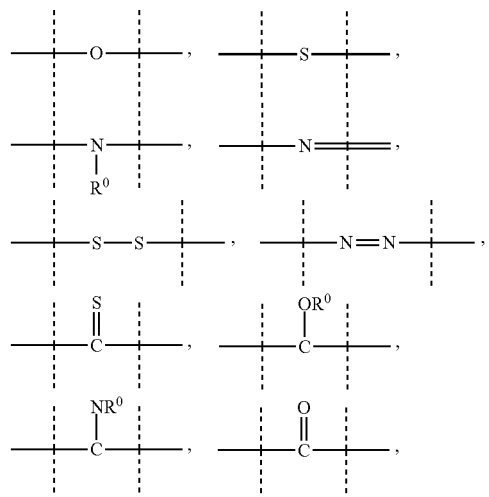

wherein dashed lines indicate attachment points, and $R^0$ and $R^{0a}$ are independently of each other selected from H and $C_{1-6}$ alkyl;

and which $X^{OB}$ is optionally substituted with one or more $R^1$, which are the same or different; wherein $R^1$ is halogen, $C_{1-6}$ alkyl, CN, C(O)H, C(O)OH, OH, C(O)H, C(O)NH$_2$, S(O)$_2$NH$_2$, S(O)NH$_2$, S(O)$_2$H, S(O)H, NHS(O)$_2$NH$_2$, SH, NH$_2$, NO$_2$, OC(O)H, NHC(O)H, NHSO$_2$H, NHS(O)H, NHC(O)NH$_2$, NHC(O)OH, OC(O)NH$_2$, phenyl, naphthyl, azulenyl, indenyl, indanyl, $C_{3-7}$ cycloalkyl, 3- to 7-membered heterocyclyl, or 8- to 11-membered heterobicyclyl.

Preferably, $X^{OB}$ is interrupted by 1, 2, 3, 4, 5, 6, 7, or 8 of the above listed bivalent groups, more preferably, $X^{OB}$ is interrupted by 2, 3, 4, 5, or 6 of the above listed bivalent groups and most preferably, $X^{OB}$ is interrupted by 3 or 4 of the above listed bivalent groups and most preferably, $X^{OB}$ is interrupted by 3 of the above listed bivalent groups.

Even more preferably, $X^{OB}$ is a linear or branched $C_{1-50}$ alkyl, $C_{2-50}$ alkenyl or $C_{2-50}$ alkinyl which is optionally one or more times interrupted by one or more of the following bivalent groups -continued

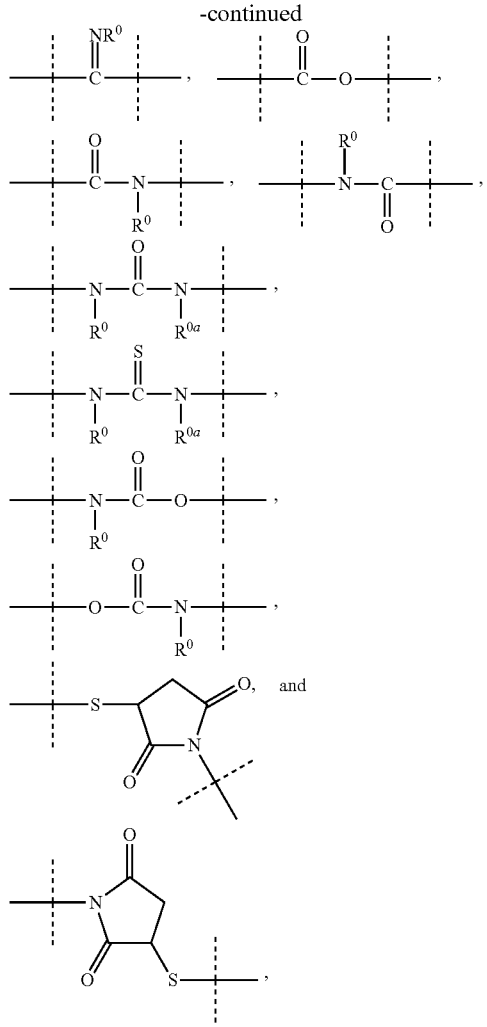

wherein
dashed lines indicate attachment points, and
$R^0$ and $R^{0a}$ are independently of each other selected from H and $C_{1-6}$ alkyl.

Preferably, $R^0$ and $R^{0a}$ are both H.

Even more preferably, $X^{0C}$ is a linear or branched $C_{1-25}$ alkyl, $C_{2-25}$ alkenyl or $C_{2-25}$ alkinyl which is optionally one or more times interrupted by one or more of the following bivalent groups

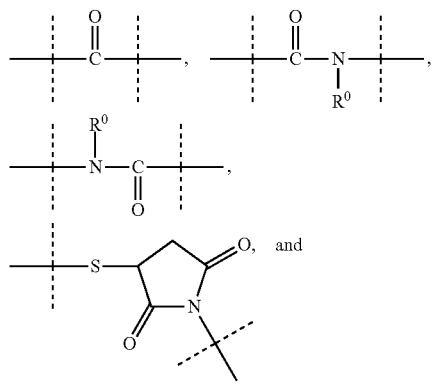

-continued

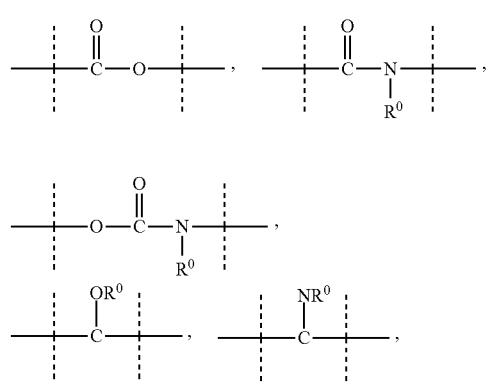

wherein
dashed lines indicate the attachment point.
Even more preferably, $X^{OB}$ is of formula (Ica) or (Icb):

(Ica)

[structure with $X^1$, N, S-(CH$_2$)$_{y1}$-NH, C=O]

(Icb)

[structure with $X^1$-N(H)-(CH$_2$)$_{y1}$-N(H)-C=O]

wherein
the dashed line marked with the asterisk indicates attachment to $Z^1$ and the unmarked dashed line indicates attachment to $X^{OA}$;
y1 is 1, 2, 3, 4, 5, 6, 7, 8, 9, or 10; and
$X^1$ is $C_{1-10}$ alkyl, $C_{2-10}$ alkenyl, or $C_{2-10}$ alkynyl, which is optionally interrupted by one or more of the following bivalent groups:

[bivalent groups: —O—, —S—, —N(R$^0$)—, —S—S—, —C(O)—O—, —C(O)—N(R$^0$)—, —O—C(O)—N(R$^0$)—, —C(OR$^0$)—, —C(NR$^0$)—]

-continued

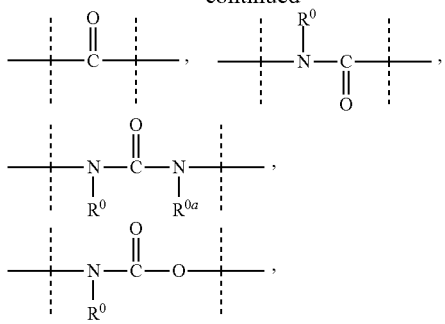

wherein dashed lines indicate attachment points; and $R^0$ and $R^{0a}$ are independently of each other selected from H and $C_{1-6}$ alkyl.

Preferably, y1 of formula (Ica) and (Icb) is 4, 5, 6, 7 or 8, more preferably y1 is 5, 6, or 7 and most preferably y1 is 6.

Even more preferably, $X^{OB}$ is of formula (Ibc):

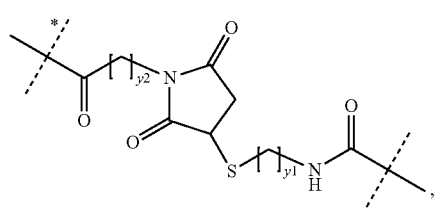

(Ibc)

wherein the dashed line marked with the asterisk indicates attachment to $Z^1$ and the unmarked dashed line indicates attachment to $X^{OA}$;

y1 is 1, 2, 3, 4, 5, 6, 7, 8, 9, or 10; and y2 is 1, 2, 3, 4, or 5.

Preferably, y1 of formula (Ibc) is 4, 5, 6, 7 or 8, more preferably y1 is 5, 6, or 7 and most preferably y1 is 6.

Preferably, y2 of formula (Ibc) is 2 or 3, most preferably y2 is 2.

Most preferably, $X^{OB}$ is of formula (Ibd):

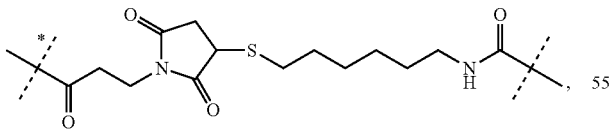

(Ibd)

wherein the dashed line marked with the asterisk indicates attachment to $Z^1$ and the unmarked dashed line indicates attachment to $X^{OA}$.

Preferably, the carrier $Z^1$ is covalently attached to a moiety $X^0$ via an amide linkage.

Preferably, the moiety —$X^0$-$L^0$-$PG^0$ of formula (I) has the structure of formula (IIa) or (IIb):

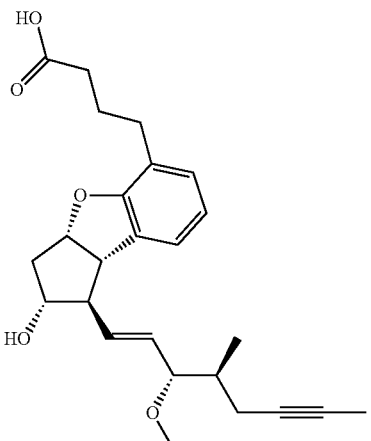

(IIa)

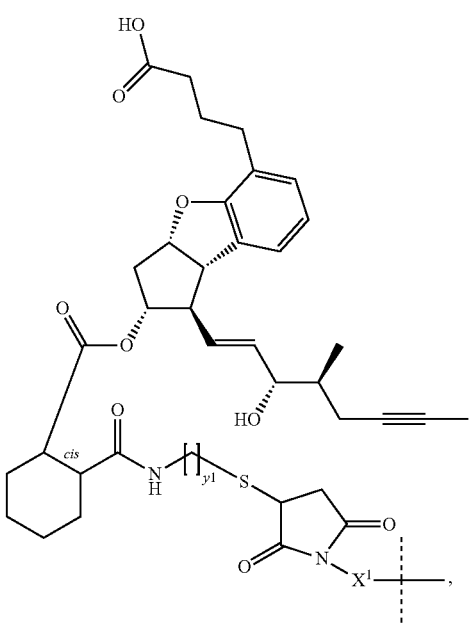

(IIb)

wherein dashed lines indicate the attachment point to $Z^1$;

$X^1$ is $C_{1-10}$ alkyl, $C_{2-10}$ alkenyl, or $C_{2-10}$ alkynyl, which is optionally interrupted by one or more of the following bivalent groups:

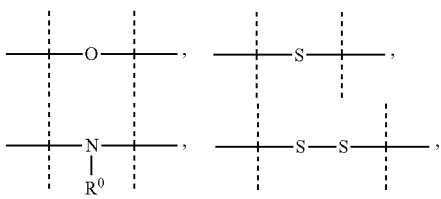

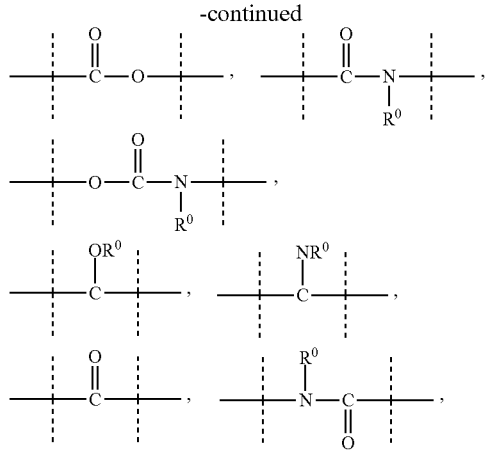
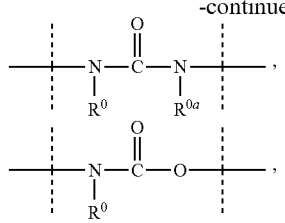
wherein
dashed lines indicate attachment points; and
$R^0$ and $R^{0a}$ are independently of each other selected from H and $C_{1-6}$ alkyl.
Preferably, y1 of formula (IIa) and (IIb) is 4, 5, 6, 7 or 8, more preferably y1 is 5, 6, or 7 and most preferably y1 is 6.
More preferably, the moiety —$X^0$-$L^0$-$PG^0$ of formula (I) has the structure of formula (IIaa) or (IIba):
(IIaa)
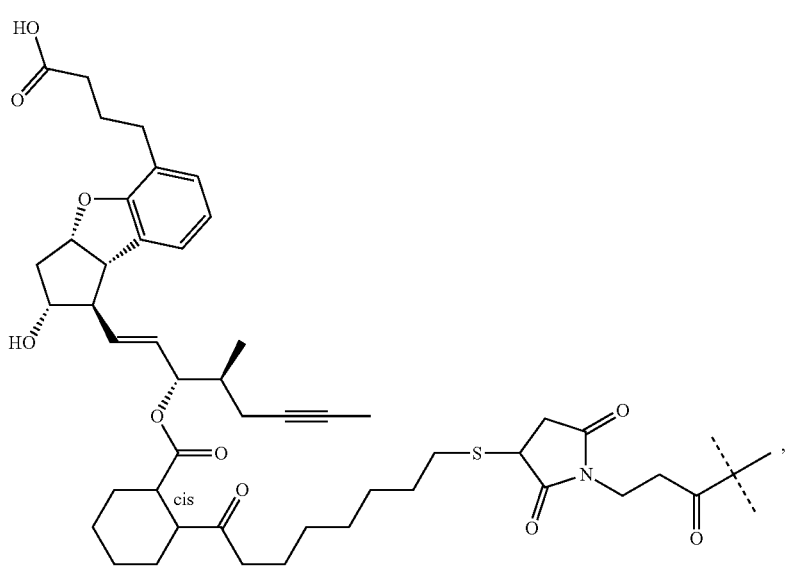
(IIba)
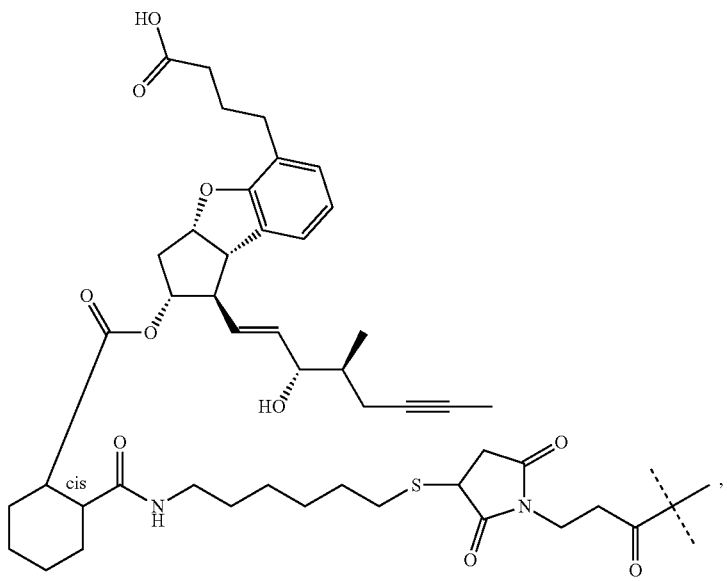

wherein
dashed lines indicate the attachment point to $Z^1$.

Most preferably, the moiety —$X^0$-$L^0$-$PG^0$ of formula (I) has the structure of formula (IIbaa) or (IIbab):

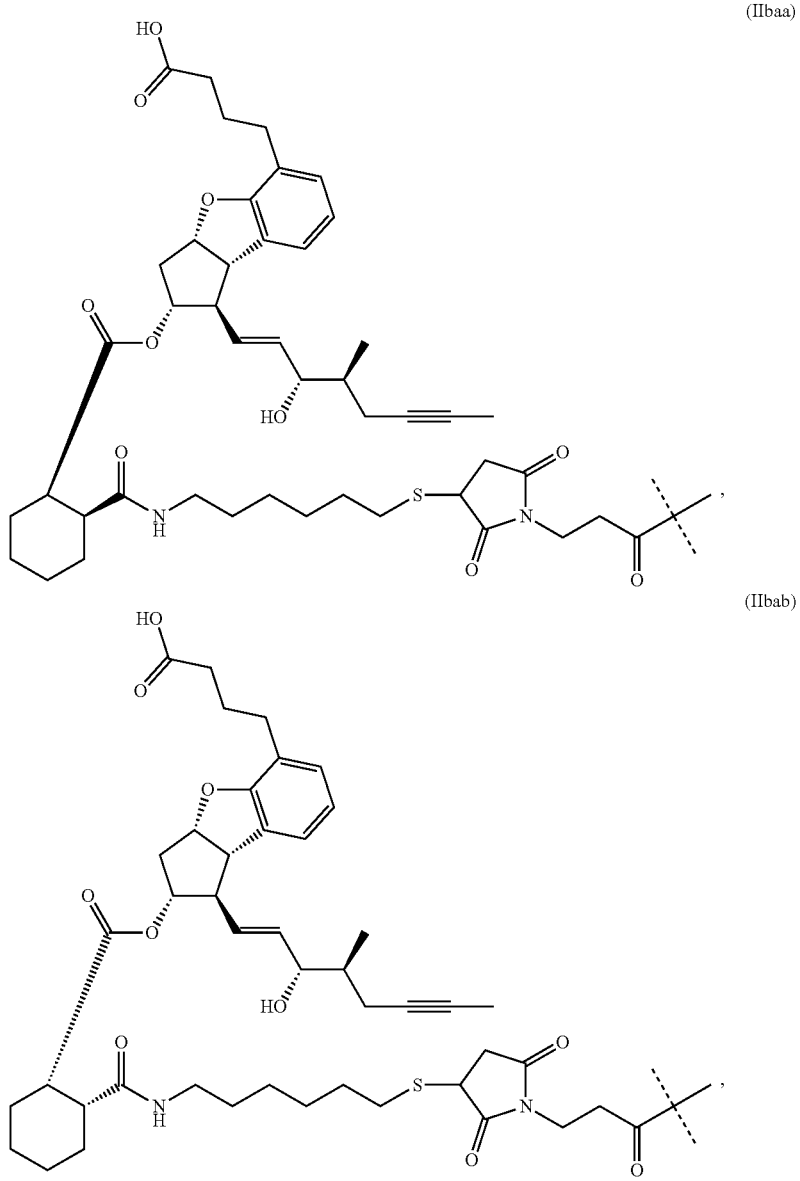

wherein
dashed lines indicate the attachment point to $Z^1$.

In one embodiment the carrier $Z^1$ of formula (I) comprises a covalently bound $C_{10-24}$ fatty acid.

In another embodiment $Z^1$ of formula (I) comprises a covalently bound polymer, preferably a pharmaceutically acceptable polymer.

Preferably, $Z^1$ has a molecular weight of 0.5 to 160 kDa, more preferably of 1 to 120 kDa, even more preferably of 5 to 100 kDa, even more preferably of 10 to 80 kDa, even more preferably of 10 to 70 kDa and most preferably of 20 to 60 kDa.

$Z^1$ preferably comprises a polymer selected from 2-methacryloyl-oxyethyl phosphoyl cholins, hydrogels, PEG-based hydrogels, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazo lines), poly(hydroxymethacrylates), poly(hydroxypropylmethacrylamides), poly(hydroxypropyl methacrylates), poly(hydroxypropyloxazolines), poly(imino carbonates), poly(lactic acids), poly(lactic-co-glycolic acids), poly(methacrylamides), poly(methacrylates), poly(methyloxazolines) poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof.

Preferably, $Z^1$ comprises a poly(oxazoline)-, hyaluronic acid- or a PEG-based polymer. Most preferably, $Z^1$ comprises a PEG-based polymer.

In one embodiment $Z^1$ is a hydrogel (as one option for a polymer) which are known in the art. Suitable hydrogels are described in WO-A 2006/003014, WO-A 2011/012715 and unpublished International patent application PCT/EP2013/070962. If the carrier $Z^1$ is a hydrogel it is preferred that it is a PEG-based hydrogel as disclosed in WO-A 2011/012715 which is incorporated by reference herewith.

Preferably, the carrier $Z^1$ is a water-soluble carrier.

In one embodiment the carrier $Z^1$ has the structure of formula (A-i) or (A-ii):

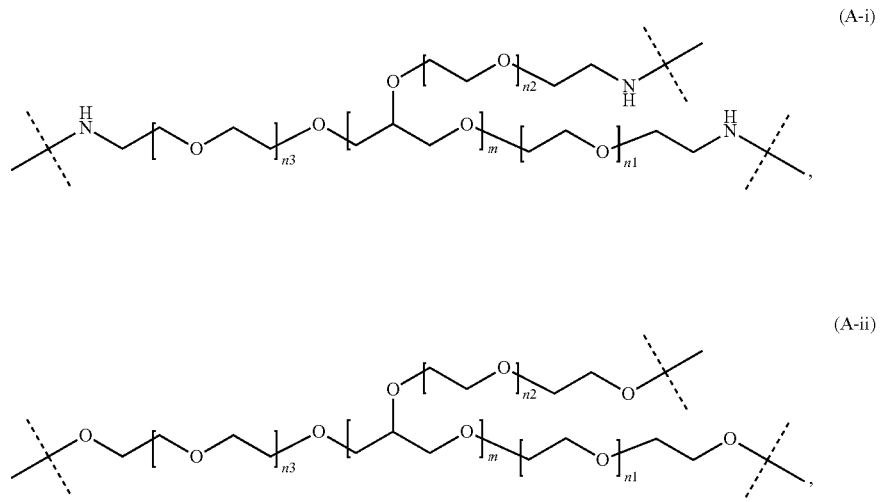

wherein
dashed lines indicate attachment points, i.e. to $X^0$ of formula (I);
each of n1, n2 and n3 are independently an integer ranging of from 5 to 500; and
m is an integer ranging from 2 to 32.

Preferably, m in formula (A-i) and (A-ii) is an integer ranging from 2 to 14 and more preferably m is 6.

Preferably, each of n1, n2, and n3 in formula (A-i) and (A-ii) independently range from 10 to 250, more preferably from 50 to 150. Preferably, n1, n2, and n3 are the same.

It is understood that the term "dashed lines indicate attachment points, i.e. to $X^0$ of formula (I)" includes attachment to $X^{0B}$; to $X^{0A}$; if m1=0; to $L^0$, if both m1 and m2 are 0; and to $X^1$ if the prodrug is of formula (Ica), (Icb), (IIa), and (IIb).

In an alternative embodiment $Z^1$ has the structure of formula (A-iii):

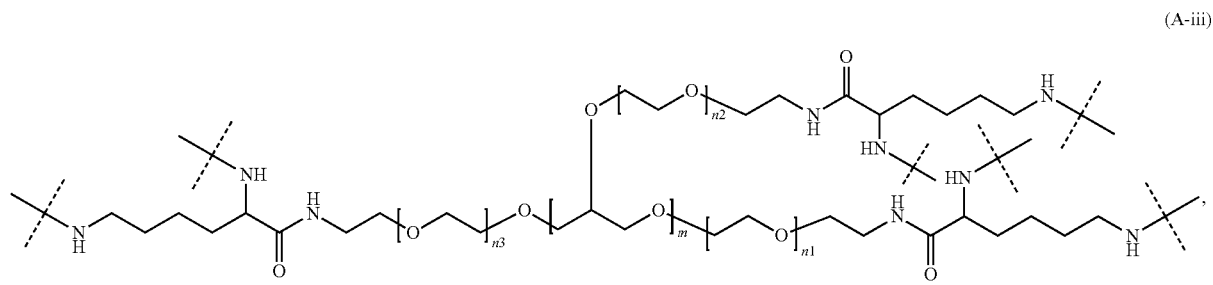

wherein
dashed lines indicate attachment points, i.e. to $X^0$ of formula (I);
each of n1, n2 and n3 are independently an integer ranging of from 5 to 500; and
m is an integer ranging from 2 to 32.

Preferably, m in formula (A-iii) is an integer ranging of from 2 to 6 and more preferably m is 2.

Preferably, each of n1, n2, and n3 in formula (A-iii) independently range from 10 to 250, more preferably from 50 to 150. Preferably, n1, n2, and n3 are the same.

In another preferred embodiment $Z^1$ is a carrier as disclosed in WO2013/024048A1, which is herewith incorporated by reference in its entirety. Accordingly, in a preferred embodiment $Z^1$ has the structure of formula (B-i):

$$\text{Hyp}^1{}_{mx}\text{-POL}^x\text{-Hyp}^2 \qquad (B\text{-}i),$$

wherein
$POL^x$ is a polymeric moiety having a molecular weight ranging from 0.5 kDa to 160 kDa,
$Hyp^1$ and $Hyp^2$ are independently a hyperbranched moiety, and
mx is 0 or 1.

The polymeric moiety $POL^x$ of formula (B-i) has a molecular weight of from 0.5 kDa to 160 kDa, preferably of from 2 kDa to 80 kDa and more preferably of from 5 kDa to 40 kDa.

$POL^x$ of formula (B-i) may be selected from the group of polymers consisting of, for example, polypeptides, 2-methacryloyl-oxyethyl phosphoyl cholins, water-soluble hydrogels, water-soluble PEG-based hydrogels, water-soluble hyaluronic acid-based hydrogels, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(imino carbonates), poly(lactic acids), poly(lactic-co-glycolic acids), poly(methacrylamides), poly(methacrylates), poly(methyloxazolines), poly(organophosphazenes), poly(ortho esters), poly(oxazolines), polypropylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

The polymeric moiety $POL^x$ of formula (B-i) may comprise a linear or branched polymer. Preferably, $POL^x$ of formula (B-i) comprises, in particular consists of a linear polymer.

In one preferred embodiment, $POL^x$ of formula (B-i) comprises, in particular consists of a PEG-based polymer or a poly(oxazoline)-based polymer, more preferably a linear PEG-based polymer. Even more preferably, $POL^x$ of formula (B-i) consists of a PEG-based linear polymer.

If mx in formula (B-i) is 0, it is preferred that $POL^x$ of formula (B-i) comprises, preferably consists of a structure of the formula $X1\text{-}(OCH_2CH_2)_p\text{—}O\text{—}(CH_2)_n\text{—}X2\text{-}$, wherein n is selected from 2, 3, or 4; p is an integer in the range of from 5 to 2000, preferably p is an integer in the range of from 10 to 1000, more preferably p is an integer in the range of from 100 to 1000; and X2 is a functional group covalently linking $POL^x$ and $Hyp^2$ of formula (B-i); and X1 is selected from H, $CH_3$ and $C_2H_5$.

If mx in formula (B-i) is 1, it is preferred that $POL^x$ of formula (B-i) comprises, preferably consists of a structure of the formula $X3\text{-}(CH_2)_{n1}\text{—}(OCH_2CH_2)_p\text{—}O\text{—}(CH_2)_{n2}\text{—}X2\text{-}$, wherein n1 and n2 are independently selected from 2, 3, and 4; p is an integer in the range of from 5 to 2000, preferably p is an integer in the range of from 10 to 1000, more preferably p is an integer in the range of from 100 to 1000; and X2 and X3 are functional groups covalently linking $POL^x$ to $Hyp^1$ and $Hyp^2$ of formula (B-i), respectively.

In a preferred embodiment mx in formula (B-i) is 0.

In another preferred embodiment, $POL^x$ of formula (B-i) is a polypeptide (or protein), in particular a non-immunogenic polypeptide as described below.

Preferably, the polymeric moiety $POL^x$ of formula (B-i) is a polypeptide which comprises at least about 100 amino acid residues, in particular which consists of at least about 100 amino acid residues. In a preferred embodiment, amino acids selected from alanine, serine and/or proline residues are present, in particular are mainly present, and which polypeptide moiety preferably has a random coil conformation at physiological conditions. It is understood that such a polypeptide moiety $POL^x$ of formula (B-i) may transiently or temporarily not form a random coil, for example when present in a lyophilisate or dried composition.

A polypeptide moiety $POL^x$ of formula (B-i) may have a random coil conformation with an amino acid sequence consisting of maximally about 1000 amino acid residues, preferably of maximally about 900 amino acid residues, more preferably of maximally about 800 amino acid residues, even more preferably of maximally about 700 amino acid residues, particularly preferably of maximally about 600 amino acid residues. Thus, the amino acid sequence forming random coil conformation may consist of maximally about 500 amino acid residues or of maximally about 450 amino acid residues.

It is also envisaged herein that the amino acid sequence forming random coil conformation may consist of maximally about 1200 and up to about 1500 amino acid residues. Accordingly, the amino acid sequence forming random coil conformation may consist of about 100 to about 1500 amino acid residues.

In particular embodiments said amino acid sequence forming random coil conformation consists of about 100 to 1000 amino acid residues as characterized herein, i.e. comprising alanine, serine and/or proline as main or unique residues as defined below.

In a preferred embodiment, a polypeptide moiety $POL^x$ of formula (B-i) consists mainly of one, two or three of the amino acid residues alanine, serine and proline, whereby proline residues represent preferably about 4% to about 40% of the polypeptide moiety $POL^x$ of formula (B-i). The alanine and serine residues comprise the remaining at least 60% to 96% of the polypeptide moiety $POL^x$ of formula (B-i). However, as will be detailed herein below said polypeptide moiety $POL^x$ of formula (B-i) may also comprise further amino acids differing from alanine, serine, and proline, i.e. as minor constituents.

The term "minor constituent" as used herein means that maximally 10% (i.e. maximally 10 of 100 amino acids) may be different from alanine, serine and proline, preferably maximally 8% (i.e. maximally 8 of 100 amino acids) may be different than alanine, serine and proline, more preferably maximally 6% (i.e. maximally 6 of 100 amino acids) may be different from alanine, serine and proline, even more preferably maximally 5% (i.e. maximally 5 of 100 amino acids) may be different from alanine, serine and proline, particularly preferably maximally 4% (i.e. maximally 4 of 100 amino acids) may be different from alanine, serine and proline, more particularly preferably maximally 3% (i.e. maximally 3 of 100 amino acids) may be different from alanine, serine and proline, even more particularly preferably maximally 2% (i.e. maximally 2 of 100 amino acids) may be different from alanine, serine and proline and most preferably maximally 1% (i.e. maximally 1 of 100 of the amino acids) may be different from alanine, serine and proline. Said amino acids different from alanine, serine and proline may be selected from the group consisting of different from alanine, serine and proline may be selected from the group of natural or proteinogenic amino-acids comprising Arg, Asn, Asp, Cys, Gln, Glu, Gly, His, Ile, Leu, Lys, Met, Phe, Thr, Trp, Tyr, Val, selenocystein, selenomethionin, and hydroxyproline. Minor constituents may also be selected from non-naturally occurring amino acids.

The term "at least about 100/150/200/250/300/300/350 (etc) amino acid residues" is not limited to the concise number of amino acid residues but also comprises amino acid stretches that comprise an additional 10% to 20% or comprise 10% to 20% less residues. For example "at least about 100 amino acid residues" may also encompass 80 to 100 and about 100 to 120 amino acid residues without deferring from the gist of the present invention.

In one embodiment, the polypeptide moiety POL$^x$ of formula (B-i) comprises a plurality of polymer cassettes wherein said polymer cassettes consist of one, two or three of the amino acids selected from Ala, Ser, and Pro and wherein no more than 6 consecutive amino acid residues are identical and wherein said proline residues constitute more than 4% and less than 40% of the amino acids of said polypeptide moiety POL$^x$ of formula (B-i).

A polypeptide moiety POL$^x$ of formula (B-i) may comprise a plurality, in particular 2, 3, 4, 5 or more of identical polymer cassettes or a plurality of non-identical polymer cassettes. Non-limiting examples of polymer cassettes consisting of Ala, Ser and Pro residues are provided herein below; see SEQ ID NO:9, SEQ ID NO:10, SEQ ID NO:11, SEQ ID NO:12, SEQ ID NO:13 and SEQ ID NO:14 or peptide fragments or multimers of these sequences. A polymer cassette may consist of at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each polymer cassette comprises (an) Ala, Ser, and Pro residue(s).

In one embodiment, the polymer cassette according to the present invention does not comprise more than 100 amino acid residues. Preferably, a polymer cassette as defined herein comprises more than about 4%, preferably more than about 5%, even more preferably more than about 6%, particularly preferably more than about 8%, more particularly preferably more than about 10%, even more particularly preferably more than about 15% and most preferably more than about 20% proline residues. Such polymer cassette as defined herein preferably comprises less than about 40% or less than about 35% proline residues.

In one preferred embodiment the polypeptide moiety POL$^x$ of formula (B-i) comprises, in particular consists of formula (b-a):

$$Ser_x[Ala_ySer_z]_n \qquad (b-a),$$

which formula further comprises proline residues as defined herein and wherein x is independently selected from integer 0 to 6, each y is independently selected from integer ranging of from 1 to 6, each z is independently selected from integer ranging of from 1 to 6.

n is any integer so that a polypeptide moiety POL$^x$ of formula (B-i) consists of at least about 100 amino acid residues, and in particular of at least about 100 to about 3000 amino acid residues, preferably to about 2000 and more preferably to about 1000 amino acid residues.

In another preferred embodiment, a polypeptide moiety POL$^x$ of formula (B-i) comprises no more than 5 identical consecutive amino acid residues, more preferably no more than 4 identical consecutive amino acid residues and most preferably no more than 3 identical consecutive amino acid residues.

As already indicated herein above, a polypeptide moiety POL$^x$ of formula (B-i) comprises in one embodiment proline residues, wherein said proline residues constitute more than about 4%, preferably more than about 5%, even more preferably more than about 6%, particularly preferably more than about 8%, more particularly preferably more than about 10%, even more particularly preferably more than about 15% and most preferably more than about 20% of the amino acids of POL$^x$ of formula (B-i).

In another preferred embodiment, a polypeptide moiety POL$^x$ of formula (B-i) comprises more than about 4% but less than about 50%, preferably more than about 10% but less than about 50% and most preferably more than about 20% but less than about 50% alanine residues of the amino acids constituting the polypeptide moiety POL$^x$ of formula (B-i).

In a further preferred embodiment, a polypeptide moiety POL$^x$ of formula (B-i) comprises more than about 4% and less than about 50%, preferably more than about 10% but less than about 50% and most preferably more than about 20% but less than about 50% serine residues of the amino acids constituting the polypeptide moiety POL$^x$ of formula (B-i).

Preferably, a polypeptide moiety POL$^x$ of formula (B-i) comprises about 35% proline residues, about 50% alanine residues and about 15% serine residues of the amino acids constituting the polypeptide moiety POL$^x$ of formula (B-i). Alternatively, a polypeptide moiety POL$^x$ of formula (B-i) may comprise about 35% proline residues, about 15% alanine residues and about 50% serine residues of the amino acids constituting the polypeptide moiety POL$^x$ of formula (B-i).

Preferably, a polypeptide moiety POL$^x$ of formula (B-i) comprises one or more of the following alanine-serine polymer cassettes:

AAAASSASSASSSSSAAASA   SEQ ID NO: 1

AASAAASSAAASAAAASASS   SEQ ID NO: 2

```
                                    SEQ ID NO: 3
ASASASASASASSAASAASA

SEQ ID NO: 4
SAASSSASSSSAASSASAAA

SEQ ID NO: 5
SSSSAASAASAAAAASSSAS

SEQ ID NO: 6
SSASSSAASSSASSSSASAA

SEQ ID NO: 7
SASASASASASAASSASSAS

SEQ ID NO: 8
ASSAAASAAAASSAASASSS
```

The multimers of these alanine-serine polymer cassettes may form random coil conformation in case the resulting amino acid sequence further comprises proline residues as defined herein above.

In a preferred embodiment, a polypeptide moiety POL$^x$ of formula (B-i) comprises one or more of the following polymer cassettes:

```
                                    SEQ ID NO: 9
ASPAAPAPASPAAPAPSAPA

SEQ ID NO: 10
AAPASPAPAAPSAPAPAAPS

SEQ ID No: 11
APSSPSPSAPSSPSPASPSS

SEQ ID NO: 15
SAPSPSPSAPSSPSPASPS
```

SEQ ID NO:15 corresponds to the herein provided SEQ ID NO:11 in a circularly permuted form, wherein the last serine was removed and another serine was appended as starting amino acid. As a consequence, multimers of this modified sequence possess essentially the same internal repeating unit as multimers of the non-modified sequence, except for the very first and the very last residue. Accordingly, SEQ ID NO:15 may be considered as an example of a further polymer cassette for a polypeptide moiety POL$^x$ of formula (B-i). It is clear for the person skilled in the art that also other polymer cassettes and (shorter) peptide fragments or circularly permuted versions of the herein provided amino acid polymers may be used as polymer cassettes for a polypeptide moiety POL$^x$ of formula (B-i).

Yet, even further and illustrative amino acid polymers forming random coil conformation may comprise amino acid sequences that may be selected from the group consisting of the following sequences:

```
                                    SEQ ID NO: 12
SSPSAPSPSSPASPSPSSPA

SEQ ID NO: 13
AASPAAPSAPPAAASPAAPSAPPA

SEQ ID NO: 14
ASAAAPAAASAAASAPSAAA
```

Therefore, preferred polymer cassettes for a polypeptide moiety POL$^x$ of formula (B-i) are selected from the following sequences:

```
                                    (SEQ ID NO: 9)
ASPAAPAPASPAAPAPSAPA, (SEQ ID NO: 10)
AAPASPAPAAPSAPAPAAPS, (SEQ ID NO: 11)
APSSPSPSAPSSPSPASPSS, (SEQ ID NO: 12)
SSPSAPSPSSPASPSPSSPA, (SEQ ID NO: 13)
AASPAAPSAPPAAASPAAPSAPPA,
and (SEQ ID NO: 14)
ASAAAPAAASAAASAPSAAA;
``` or circular permuted versions or (a) multimer(s) of these sequences as a whole or parts of these sequences.

Again, also (a) peptide fragment(s) or (a) multimer(s) or circularly permuted versions of these sequences and the sequences provided herein above may be employed in context of the present invention as polymer cassettes for a polypeptide moiety POL$^x$ of formula (B-i). The person skilled in the art is readily in a position to generate further amino acid polymer cassettes that form random coil conformation under physiological conditions and are constituted of mainly alanine, serine, and proline as defined herein. Such other and further examples of random coil conformation forming amino acid polymer cassettes to be used for a polypeptide moiety POL$^x$ of formula (B-i) may, inter alia, comprise combinations and/or peptide fragments or circularly permuted versions of the specific polymer cassettes shown above.

Accordingly, the exemplified polymer cassettes may also provide for individual peptide fragments which may be newly combined to form further polymer cassettes.

In accordance with the above, a polypeptide moiety POL$^x$ of formula (B-i) may comprise a multimer of sequences consisting of either one of the amino acid sequences with SEQ ID NO:9, 10, 11, 12, 13 or 14 as disclosed herein above or may comprise a multimer of sequences consisting of more than one of amino acid sequences SEQ ID NOs:9, 10, 11, 12, 13 and 14. Furthermore, it is envisaged that also peptide fragments or circularly permuted versions of these exemplified sequences may be used to build up further polymer cassettes of a polypeptide moiety POL$^x$ of formula (B-i).

In another embodiment, a polypeptide moiety POL$^x$ of formula (B-i) may comprise a multimer of sequences consisting of a (circular) permutation of the amino acid sequence selected from the group consisting of SEQ ID NO:9, 10, 11, 12, 13, 14, 15 or (a) multimers(s) of these (circular) permutated sequences.

In yet another embodiment, a polypeptide moiety POL$^x$ of formula (B-i) may comprise a multimer consisting of a peptide fragment/part of the amino acid sequence selected from the group consisting of SEQ ID NOs: 9, 10, 12, 13, 14, 15 or (a) multimers(s) of these exemplified polymer cassettes.

Peptide fragments of these sequences to be employed for the generation of a polypeptide moiety POL$^x$ of formula (B-i) may consist of at least 3, preferably of at least 4, more preferably of at least 5, even more preferably of at least 6, still more preferably of at least 8, particularly preferably of at least 10, more particularly preferably of at least 12, even more particularly preferably of at least 14, preferably of at least 6, still more preferably of at least 8, particularly preferably of at least 10, more particularly preferably of at least 12, even more particularly preferably of at least 14, even more particularly preferably of at least 16, and most preferably of at least 18 consecutive amino acids of the amino acid sequence selected from the group consisting of said SEQ ID NOs: 9, 10, 11, 12, 13 and 14.

For example, individual peptide fragments of the inventive polymer cassettes may be combined to further individual polymer cassettes as long as the above-identified rules for the overall distribution and amount of alanine, serine and proline are respected. Again, these polymer cassettes may also comprise further amino acid residues, however only as minimal or minor constituents, i.e. maximally 10%, preferably maximally 2% of the individual polymer cassette. $POL^x$ of formula (B-i) moieties comprising polymer cassettes consist, in one embodiment of the present invention, of at least about 100 amino acid residues. Individual polymer cassettes may be combined in order to form longer random coil forming amino acid polymers, whereby a maximal length of a polypeptide moiety $POL^x$ of formula (B-i) is about 3000 amino acids.

Preferably, $POL^x$ of formula (B-i) is covalently linked to $Hyp^1$ and $Hyp^2$ of formula (B-i), in particular by a permanent linkage, more preferably by a permanent amide linkage.

In the carrier-linked treprostinil prodrugs of the present invention functional groups of $Hyp^1$ and $Hyp^2$ of formula (B-i) are connected to the remainder of the prodrug of formula (I).

The hyperbranched moieties $Hyp^1$ and $Hyp^2$ of formula (B-i) are each independently selected from the group comprising, in particular consisting of, in bound form glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, dilysine, trilysine, tetralysine, pentalysine, hexalysine, heptalysine, octalysine, nonalysine, decalysine, undecalysine, dodecalysine, tridecalysine, tridecalysine, tetradecalysine, pentadecalysine, hexadecalysine, heptadecalysine, octadecalysine, nonadecalysine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid, di(glutamic acid), tri(glutamic acid), tetra(glutamic acid), penta(glutamic acid), hexa(glutamic acid), hepta(glutamic acid), octa(glutamic acid), nona(glutamic acid), deca(glutamic acid), undeca(glutamic acid), dodeca(glutamic acid), trideca(glutamic acid), tetradeca(glutamic acid), pentadeca(glutamic acid), hexadeca(glutamic acid), heptadeca(glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and low-molecular weight PEI.

In a preferred embodiment, the hyperbranched moieties $Hyp^1$ and $Hyp^2$ of formula (B-i) are each independently selected from the group comprising, in particular consisting of, in bound form dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid, di(glutamic acid), tri(glutamic acid), tetra(glutamic acid), penta(glutamic acid), hexa(glutamic acid), hepta(glutamic acid), octa(glutamic acid), nona(glutamic acid), deca(glutamic acid), undeca(glutamic acid), dodeca(glutamic acid), trideca(glutamic acid), tetradeca(glutamic acid), pentadeca(glutamic acid), hexadeca(glutamic acid), heptadeca(glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and low-molecular weight PEI.

More preferably, the hyperbranched moieties $Hyp^1$ and $Hyp^2$ of formula (B-i) are independently selected from the group comprising, more preferably consisting of, in bound form, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, and heptadecalysine, even more preferably $Hyp^1$ and $Hyp^2$ are independently comprising, preferably consisting of, in bound form, trilysine, heptalysine or pentadecalysine.

More preferably, $Hyp^1$ and $Hyp^2$ of formula (B-i) are independently selected from any one of the following structures:

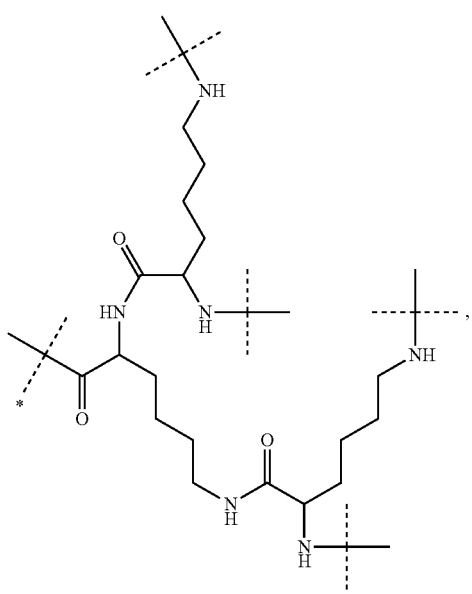
(b-i)
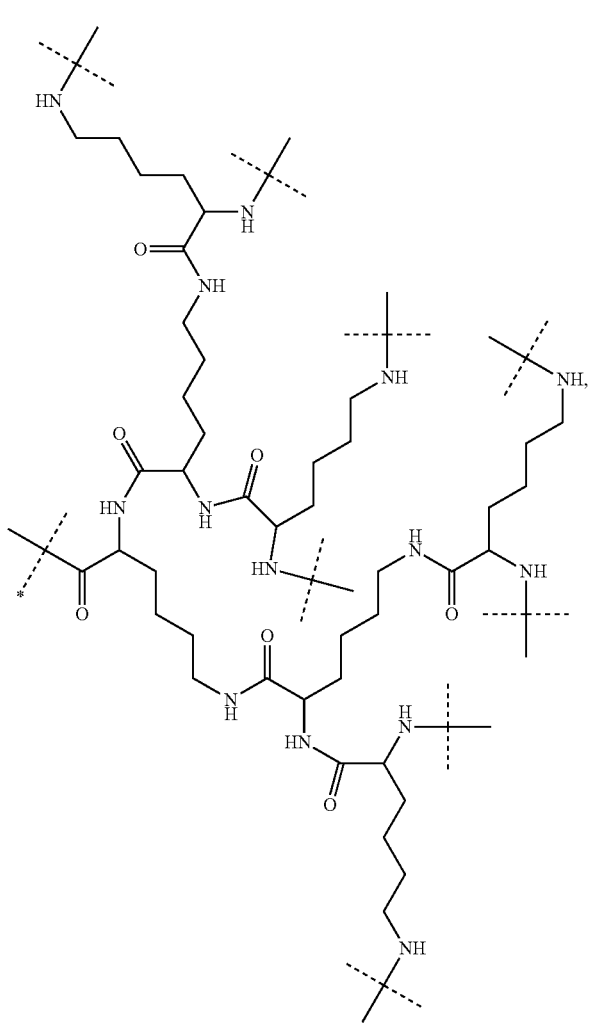
(b-ii)

(b-iii)
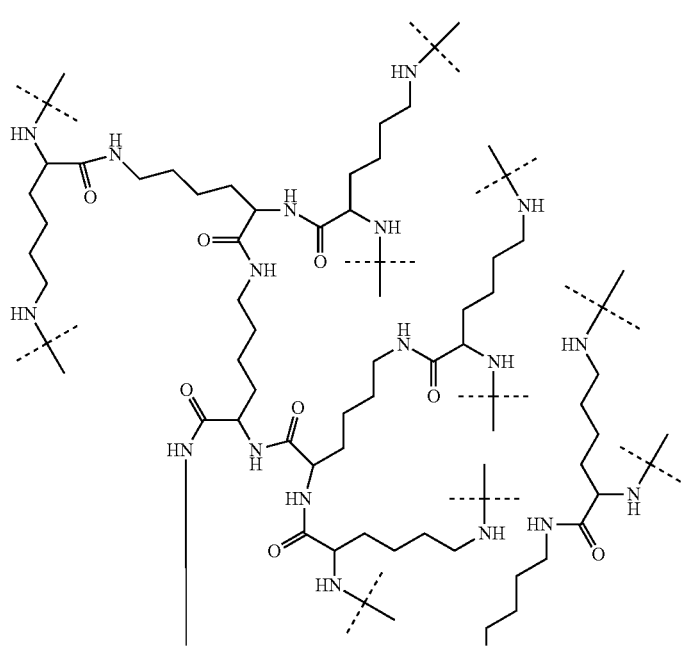
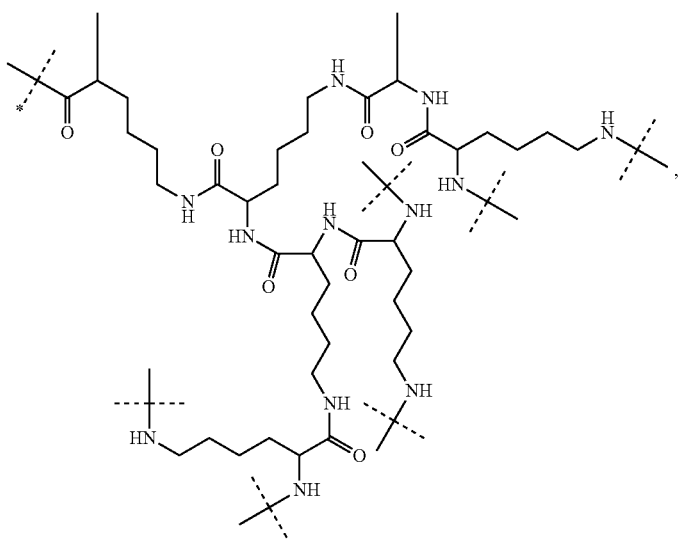
(b-iv)
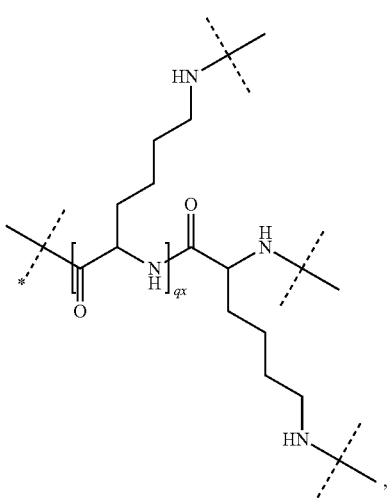

wherein dashed lines marked with an asterisk indicate attachment to POL$^x$ of formula (B-i), unmarked dashed lines indicate attachment to the rest of formula (I), and qx is an integer of from 0 to 15, preferably 3 to 7, and even more preferably 6.

Preferably, Hyp$^1$ and Hyp$^2$ of formula (B-i) are each a heptalysinyl group, in particular Hyp$^1$ and Hyp$^2$ of formula (B-i) each have the structure of formula (b-ii) above.

Preferably, Hyp$^1$ and Hyp$^2$ of formula (B-i) have the same structure.

Functional groups of Hyp$^1$ and Hyp$^2$ of formula (B-i) serve as attachment points for direct linkage of Hyp$^1$ and Hyp$^2$ of formula (B-i) to the rest of the prodrug of formula (I). Remaining functional groups may, independently of each other, be capped with suitable capping reagents or may optionally be connected to at least one targeting moiety, in particular through permanent linkages Therefore, in the water-soluble carrier-linked prodrugs of the present invention the hyperlinked moieties Hyp$^1$ and Hyp$^2$ of formula (B-i) are connected to POL$^x$ of formula (B-i) and functional groups of Hyp$^1$ and Hyp$^2$ of formula (B-i) are connected to the rest of the prodrug of formula (I), to permanent linkages, targeting moieties and/or capping groups.

In a preferred embodiment, all functional groups of the hyperbranched moieties Hyp$^1$ and Hyp$^2$ of formula (B-i) are connected to the rest of the prodrug of formula (I).

Preferably, the hyperbranched moieties Hyp$^1$ and Hyp$^2$ of formula (B-i) have independently a molecular weight in the range of from 0.1 kDa to 4 kDa, more preferably 0.4 kDa to 2 kDa. Preferably, the hyperbranched moieties Hyp$^1$ and Hyp$^2$ of formula (B-i) have each independently of each other at least 3 branchings and have at most 63 branchings. It is preferred that the hyperbranched moieties Hyp$^1$ and Hyp$^2$ of formula (B-i) have each independently of each other at least 7 branchings and at most 31 branchings.

Preferably, the hyperbranched moieties Hyp$^1$ and Hyp$^2$ of formula (B-i) are each independently a hyperbranched polypeptide. Preferably, such hyperbranched polypeptide comprises lysine in bound form. Preferably, each hyperbranched moiety Hyp$^1$ and Hyp$^2$ of formula (B-i) independently have a molecular weight in the range of from 0.1 kDa to 4 kDa, in particular 0.4 kDa to 2 kDa.

Preferably, mx is 0 and POL-Hyp$^2$- of formula (B-i) is selected from the following structures:

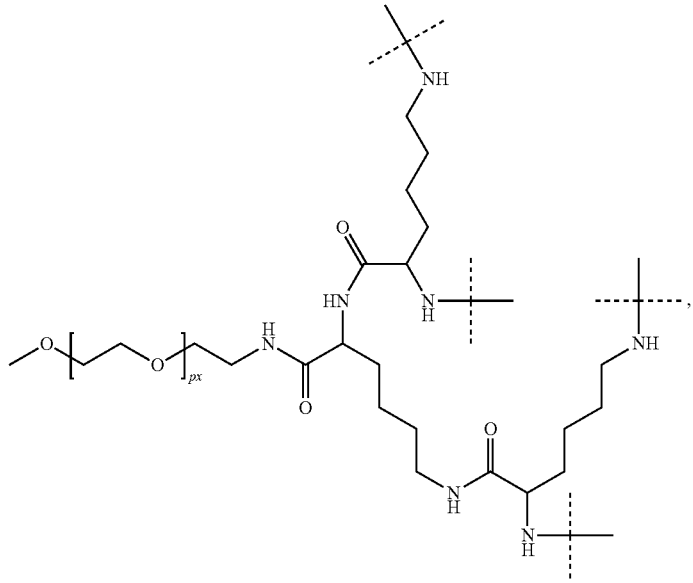

(b-v)

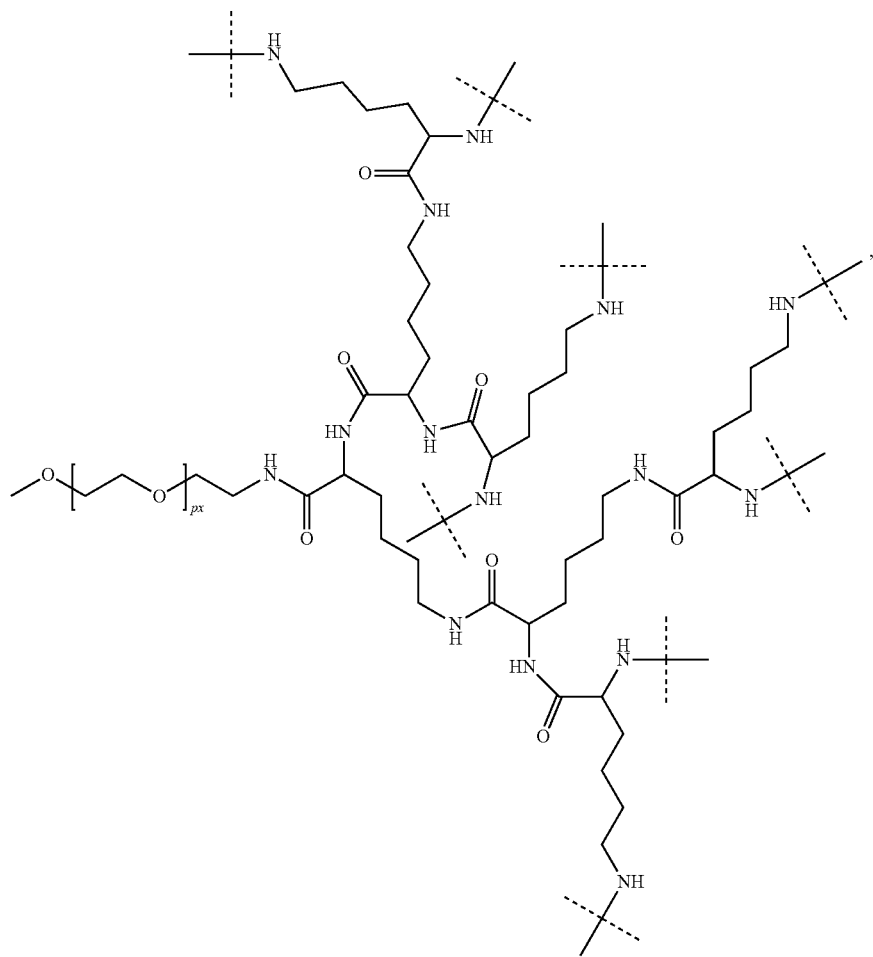
(b-vi)
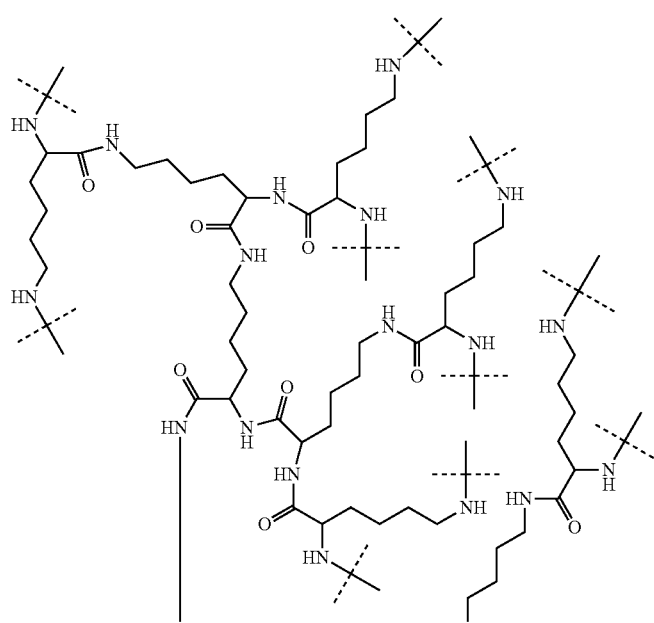
(b-vii)

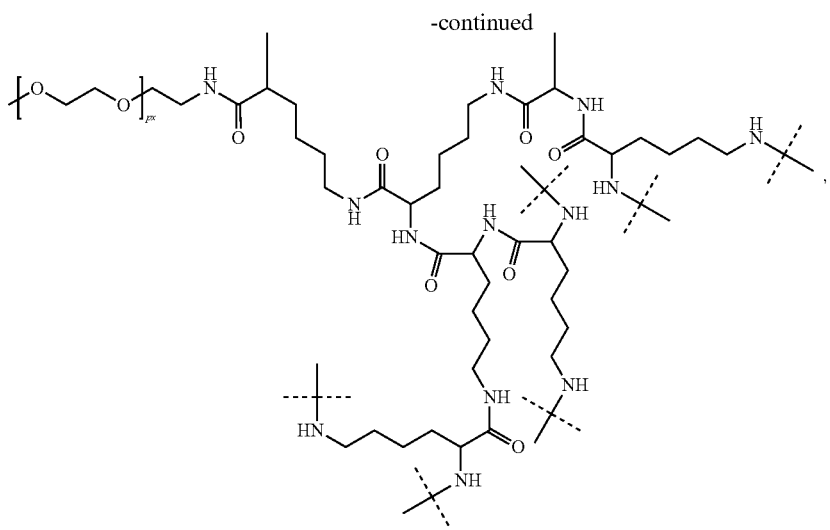

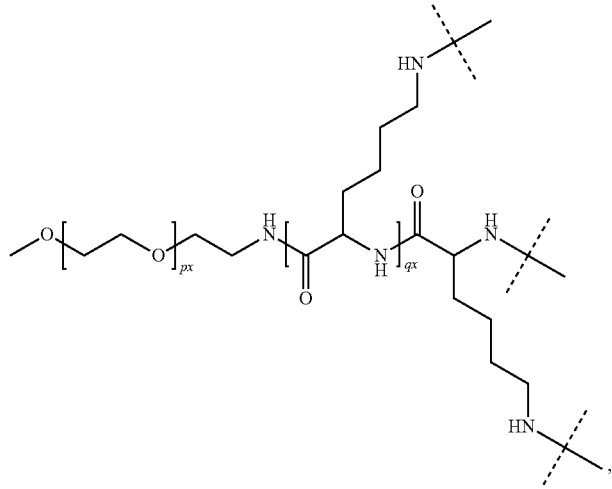

(b-viii)

wherein
dashed lines indicate attachment to the rest of the prodrug of formula (I),
px is an integer of from 5 to 2000, preferably 10 to 1000, in particular 100 to 1000, and
qx is an integer of from 0 to 15, preferably 3 to 7, more preferably, qx is 6.

In another preferred embodiment $Z^1$ is a carrier as disclosed in WO2103/024047A1, which is herewith incorporated by reference in its entirety. Accordingly, in a preferred embodiment $Z^1$ has the structure of formula (C-i):

(C-i), wherein
B is a branching core,
each A is independently a poly(ethylene glycol)-based polymeric chain,
each $Hyp^y$ is independently a branched moiety, and
n is an integer of from 3 to 32;

In a preferred embodiment, the branching core B of formula (C-i) comprises, preferably consists of a moiety selected from:
a polyalcohol comprising at least 2 hydroxyl groups (preferably further comprising a functional group, which is preferably an additional amino group or a carboxylic acid group, more preferably an additional carboxylic acid group),
preferably B is selected from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans, erythritol, threitol, arabitol, xylitol, ribitol, dulcitol, iditol; more preferably from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans.
or a polyamine comprising at least 2 amine groups (preferably further comprising a functional group, which is preferably an additional hydroxyl group or a carboxylic acid group, more preferably a carboxylic acid group),
preferably selected from ornithine, diornithine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, diaminobutyric acid, di(diaminobutyric acid), tri(diaminobutyric acid), tetra(diaminobutyric acid), penta(diaminobutyric acid), hexa(diaminobutyric acid), hepta(diaminobutyric acid), octa(diaminobutyric acid), nona(diaminobutyric acid), deca(diaminobutyric acid), undeca(diaminobutyric acid), dodeca(diaminobutyric acid), trideca(diaminobutyric acid), tetradeca(diaminobutyric acid), pentadeca(diaminobutyric acid), hexadeca(diaminobutyric acid), heptadeca(diaminobutyric acid), octadeca (diaminobutyric acid), nonadeca(diaminobutyric acid), lysine, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, oligo lysines, polyethyleneimines, and polyvinylamines;

wherein the polyalcohol or polyamine is in bound form.

In a preferred embodiment, the branching core B of formula (C-i) comprises, preferably consists of pentaerithritol.

Preferably, a poly(ethylene glycol)-based polymeric chain A connected to the branching core B of formula (C-i) consists of a linear PEG chain, of which one terminus is connected to B of formula (C-i) and the other terminus is connected to $Hyp^y$ of formula (C-i). It is understood that a PEG-based chain A of formula (C-i) may optionally be terminated in case of a branched PEG chain and/or may optionally be interrupted in case of a branched or linear PEG chain by alkyl or aryl groups and may optionally be substituted with heteroatoms and/or functional groups.

Each sub-structure A-$Hyp^y$ of formula (C-i) extending from the branching core B of formula (C-i) may be independently of each other the same or different sub-structures A-$Hyp^y$. In a preferred embodiment, the all sub-structures A-$Hyp^y$ of formula (C-i) are the same.

Each A and each $Hyp^y$ of formula (C-i) may be independently selected from the other moieties A and $Hyp^y$. Preferably, all sub-structures A-$Hyp^y$ connected to B of formula (C-i) have an identical structure.

Preferably, the PEG-based polymeric chains A of formula (C-i) are connected to B through permanent linkages.

n of formula (C-i) is an integer from 3 to 32. Preferably, n is an integer from 3 to 16, more preferably n is an integer from 4 to 8 and most preferably n is 4.

In a preferred embodiment n of formula (C-i) is 4 and m is 2.

In one embodiment, a PEG-based polymeric chain A of formula (C-i) is selected from a linear or branched PEG-based polymeric chain. Preferably, A is a linear PEG-based polymeric chain.

Preferably, each A of formula (C-i) is independently selected from the formula

—X3-$(CH_2)_{n1}$—$(OCH_2CH_2)_p$—O—$(CH_2)_{n2}$—X2-, wherein n1 and n2 are independently selected from 1, 2, 3, and 4, preferably from 1, 2, and 3; p is an integer in the range of from 5 to 2000, preferably p is an integer in the range of from 10 to 1000, more preferably p is an integer in the range of from 100 to 1000; and X3 and X2 are independently functional groups covalently linked to B or $Hyp^y$, respectively.

Preferably, a linkage between a moiety A and a moiety $Hyp^y$ of formula (C-i) is a permanent linkage, more preferably a permanent linkage comprising a linkage group comprising, in particular consisting of a group selected from amine groups, amide groups, carbamate groups, thioether groups, ether groups, and most preferably a permanent linkage between a moiety A and a moiety $Hyp^y$ of formula (C-i) is an amide linkage.

In a preferred embodiment, a sub-structure B—$(A)_n$ of formula (C-i) is a multi-arm PEG derivative as, for instance, detailed in the products list of JenKem Technology, USA (accessed by download from http://jenkemusa.net/pegproducts2.aspx on Mar. 8, 2011), such as a 4-arm-PEG derivative, in particular comprising a pentaerythritol core, an 8-arm-PEG derivative comprising a hexaglycerin core, and an 8-arm-PEG derivative comprising a tripentaerythritol core. Most preferred are sub-structures B—$(A)_n$ of formula (C-i) comprising, in particular consisting of, moieties selected from:

a 4-arm PEG Amine comprising a pentaerythritol core:

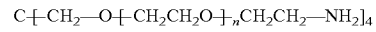
$C\text{---}[CH_2\text{---}O\text{---}[CH_2CH_2O]_n\text{---}CH_2CH_2\text{---}NH_2]_4$ with n ranging from 400 to 2000;
a 4-arm PEG Carboxyl comprising a pentaerythritol core:

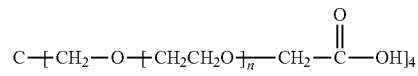

with n ranging from 400 to 2000;
an 8-arm PEG Amine comprising a hexaglycerin core:

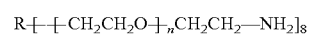
$R\text{---}[\text{---}[CH_2CH_2O]_n\text{---}CH_2CH_2\text{---}NH_2]_8$ with n ranging from 400 to 2000 and
R=hexaglycerin core structure;
an 8-arm PEG Carboxyl comprising a hexaglycerin core:

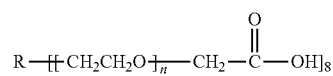

with n ranging from 400 to 2000 and
R=hexaglycerin core structure;
an 8-arm PEG Amine comprising a tripentaerythritol core:

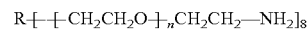
$R\text{---}[\text{---}[CH_2CH_2O]_n\text{---}CH_2CH_2\text{---}NH_2]_8$ with n ranging from 400 to 2000
and R=tripentaerythritol core structure;
and an 8-arm PEG Carboxyl comprising a tripentaerythritol core:

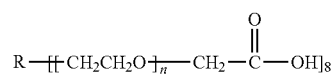

with n ranging from 400 to 2000 and
R=tripentaerythritol core structure;
a 6-arm PEG Amine comprising a sorbitol or dipentaerythritol core:

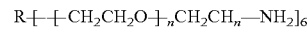
$R\text{---}[\text{---}[CH_2CH_2O]_n\text{---}CH_2CH_n\text{---}NH_2]_6$ with n ranging from 400 to 2000 and R=sorbitol or dipentaerythritol;
an 8-arm PEG Carboxyl comprising a sorbitol or dipentaerythritol core:

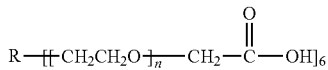

with n ranging from 400 to 2000 and
R=sorbitol or dipentaerythritol;
an 8-arm PEG Amine comprising a sorbitol or dipentaerythritol core:

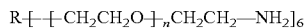

with n ranging from 400 to 2000
and R=sorbitol or dipentaerythritol;
and an 8-arm PEG Carboxyl comprising a sorbitol or dipentaerythritol core:

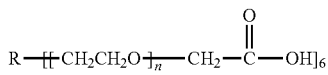

with n ranging from 400 to 2000 and
R=sorbitol or dipentaerythritol;
each in bound form.

Also preferred are sub-structures B—(A)$_n$ of the following formulas:
a 4-arm PEG Amine comprising a pentaerythritol core:

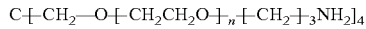

with n ranging from 400 to 2000;
a 4-arm PEG Carboxyl comprising a pentaerythritol core:

with n ranging from 400 to 2000;
an 8-arm PEG Amine comprising a hexaglycerin core:

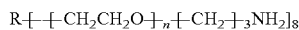

with n ranging from 400 to 2000 and
R=hexaglycerin core structure;
an 8-arm PEG Carboxyl comprising a hexaglycerin core:

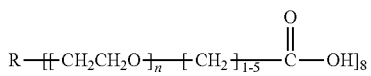

with n ranging from 400 to 2000 and
R=hexaglycerin core structure;
an 8-arm PEG Amine comprising a tripentaerythritol core:

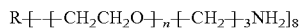

with n ranging from 400 to 2000
and R=tripentaerythritol core structure;
and an 8-arm PEG Carboxyl comprising a tripentaerythritol core:

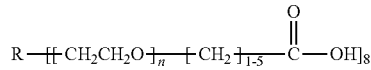

with n ranging from 400 to 2000 and
R=tripentaerythritol core structure;
a 6-arm PEG Amine comprising a sorbitol or dipentaerythritol core:

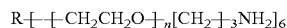

with n ranging from 400 to 2000 and
R=sorbitol or dipentaerythritol;
a 6-arm PEG Carboxyl comprising a sorbitol or dipentaerythritol core:

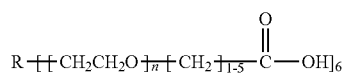

with n ranging from 400 to 2000 and
R=sorbitol or dipentaerythritol;
a 6-arm PEG Amine comprising a sorbitol or dipentaerythritol core:

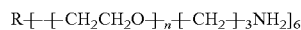

with n ranging from 400 to 2000
and R=sorbitol or dipentaerythritol;
and a 6-arm PEG Carboxyl comprising a sorbitol or dipentaerythritol core:

with n ranging from 400 to 2000 and
R=sorbitol or dipentaerythritol;
each in bound form.

Also preferred are sub-structures B—(A)$_n$ of formula (C-i) comprising, in particular consisting of, moieties selected from:
a 4-arm PEG Amine comprising a pentaerythritol core:

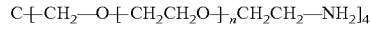

with n ranging from 20 to 500;
a 4-arm PEG Carboxyl comprising a pentaerythritol core:

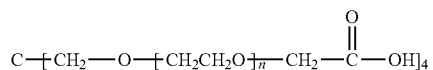

with n ranging from 20 to 500;
an 8-arm PEG Amine comprising a hexaglycerin core:

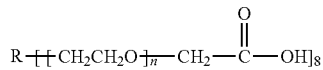

with n ranging from 20 to 500; and
R=hexaglycerin core structure;
an 8-arm PEG Carboxyl comprising a hexaglycerin core:

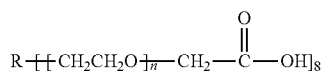

with n ranging from 20 to 500; and
R=hexaglycerin core structure;
an 8-arm PEG Amine comprising a tripentaerythritol core:

R—[—[—CH$_2$CH$_2$O—]$_n$CH$_2$CH$_2$—NH$_2$]$_8$ with n ranging from 20 to 500;
and R=tripentaerythritol core structure;
and an 8-arm PEG Carboxyl comprising a tripentaerythritol core:

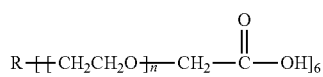

with n ranging from 20 to 500; and
R=tripentaerythritol core structure;
a 6-arm PEG Amine comprising a sorbitol or dipentaerythritol core:

R—[—[—CH$_2$CH$_2$O—]$_n$CH$_2$CH$_2$—NH$_2$]$_6$ with n ranging from 20 to 500; and
R=sorbitol or dipentaerythritol;
an 8-arm PEG Carboxyl comprising a sorbitol or dipentaerythritol core:

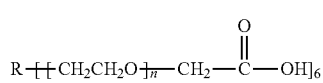

with n ranging from 20 to 500; and
R=sorbitol or dipentaerythritol;
an 8-arm PEG Amine comprising a sorbitol or dipentaerythritol core:

R—[—[—CH$_2$CH$_2$O—]$_n$CH$_2$CH$_2$NH$_2$]$_6$ with n ranging from 20 to 500;
and R=sorbitol or dipentaerythritol;
and an 8-arm PEG Carboxyl comprising a sorbitol or dipentaerythritol core:

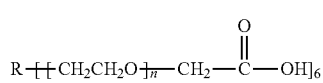

with n ranging from 20 to 500; and
R=sorbitol or dipentaerythritol;
each in bound form.

Also preferred are sub-structures B—(A)$_n$ of the following formulas:
a 4-arm PEG Amine comprising a pentaerythritol core:

C—[CH$_2$—O—[—CH$_2$CH$_2$O—]$_n$—[CH$_2$—]$_3$NH$_2$]$_4$ with n ranging from 20 to 500;
a 4-arm PEG Carboxyl comprising a pentaerythritol core:

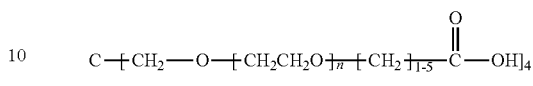

with n ranging from 20 to 500;
an 8-arm PEG Amine comprising a hexaglycerin core:

R—[—[—CH$_2$CH$_2$O—]$_n$—[CH$_2$—]$_3$NH$_2$]$_8$ with n ranging from 20 to 500; and
R=hexaglycerin core structure;
an 8-arm PEG Carboxyl comprising a hexaglycerin core:

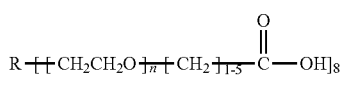

with n ranging from 20 to 500; and
R=hexaglycerin core structure;
an 8-arm PEG Amine comprising a tripentaerythritol core:

R—[—[—CH$_2$CH$_2$O—]$_n$—[CH$_2$—]$_3$NH$_2$]$_8$ with n ranging from 20 to 500;
and R=tripentaerythritol core structure;
and an 8-arm PEG Carboxyl comprising a tripentaerythritol core:

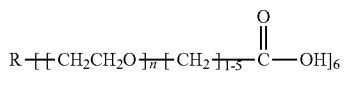

with n ranging from 20 to 500; and
R=tripentaerythritol core structure;
a 6-arm PEG Amine comprising a sorbitol or dipentaerythritol core:

R—[—[—CH$_2$CH$_2$O—]$_n$—[CH$_2$—]$_3$NH$_2$]$_6$ with n ranging from 20 to 500; and
R=sorbitol or dipentaerythritol;
a 6-arm PEG Carboxyl comprising a sorbitol or dipentaerythritol core:

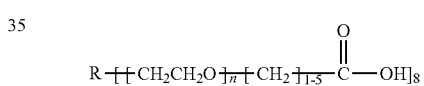

with n ranging from 20 to 500; and
R=sorbitol or dipentaerythritol;
a 6-arm PEG Amine comprising a sorbitol or dipentaerythritol core:
R—[—[—CH$_2$CH$_2$O—]$_n$—[CH$_2$—]$_3$NH$_2$]$_6$
with n ranging from 20 to 500;
and R=sorbitol or dipentaerythritol;
and a 6-arm PEG Carboxyl comprising a sorbitol or dipentaerythritol core:

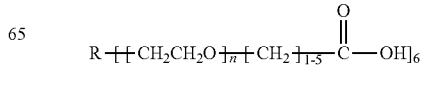

with n ranging from 20 to 500; and
R=sorbitol or dipentaerythritol;
each in bound form.

In a preferred embodiment, the molecular weight of a sub-structure B-(A)$_n$ of formula (C-i) ranges from 1 kDa to 80 kDa, more preferably 1 kDa to 40 kDa and even more preferably 10 kDa to 40 kDa. It is understood that the terminal amine groups or carboxyl groups, respectively, are used for conjugation to a moiety Hyp$^y$ of formula (C-i).

Functional groups of a moiety Hyp$^y$ of formula (C-i) are connected to the rest of the prodrug of formula (I).

In a preferred embodiment, a moiety Hyp$^y$ of formula (C-i) is connected to the remainder of the prodrug of formula (I) through a functional group selected from amide groups, carbamate groups, ester groups, ether groups, amine groups, thioether groups. Preferably, a moiety Hyp$^y$ of formula (C-i) is connected to the rest of the prodrug of formula (I) through amide groups, thioether groups and/or ether groups, even more preferably through amide groups.

Optionally, functional groups of a moiety Hyp$^y$ of formula (C-i) which are not connected to the rest of the prodrug of formula (I) may be capped with suitable capping reagents and/or may optionally be connected to at least one targeting moiety, in particular through permanent linkages. Therefore, a moiety Hyp$^y$ of formula (C-i) may be connected to the rest of the prodrug of formula (I), to capping moieties and/or targeting moieties. Preferably, all functional groups of a moiety Hyp$^y$ of formula (C-i) are connected to the rest of the prodrug of formula (I) and are not connected to capping moieties and/or targeting moieties. Targeting moieties, if present, may be conjugated to a moiety Hyp$^y$ of formula (C-i) either directly or indirectly through spacer moieties.

Examples of suitable capping moieties are linear, branched or cyclic $C_{1-8}$ alkyl groups.

The branched moiety Hyp$^y$ of formula (C-i) comprises, preferably consists of, a moiety in bound form selected from:

- a polyalcohol in bound form comprising at least 2 hydroxyl groups (preferably further comprising a functional group, which is preferably an additional hydroxyl group or a carboxylic acid group, more preferably an additional hydroxyl group),
preferably selected from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyaluronans, erythritol, threitol, arabitol, xylitol, ribitol, dulcitol, iditol; more preferably from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyaluronans;
- or a polyamine in bound form comprising at least 2 amine groups (preferably further comprising a functional group, which is preferably an additional amine group or a carboxylic acid group, more preferably a carboxylic acid group),
preferably selected from ornithine, diornithine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, diaminobutyric acid, di(diaminobutyric acid), tri(diaminobutyric acid), tetra(diaminobutyric acid), penta(diaminobutyric acid), hexa(diaminobutyric acid), hepta(diaminobutyric acid), octa(diaminobutyric acid), nona(diaminobutyric acid), deca(diaminobutyric acid), undeca(diaminobutyric acid), dodeca(diaminobutyric acid), trideca(diaminobutyric acid), tetradeca(diaminobutyric acid), pentadeca(diaminobutyric acid), hexadeca(diaminobutyric acid), heptadeca(diaminobutyric acid), octadeca(diaminobutyric acid), nonadeca(diaminobutyric acid), lysine, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, oligolysines, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid,
- or a polycarboxylate in bound form comprising at least 2 carboxylate groups (preferably further comprising a functional group, which is preferably an additional amino group or a carboxylic acid group, more preferably an additional carboxylic acid group),
preferably selected from di(glutamic acid), tri(glutamic acid), tetra(glutamic acid), penta(glutamic acid), hexa(glutamic acid), hepta(glutamic acid), octa(glutamic acid), nona(glutamic acid), deca(glutamic acid), undeca(glutamic acid), dodeca(glutamic acid), trideca(glutamic acid), tetradeca(glutamic acid), pentadeca(glutamic acid), hexadeca(glutamic acid), heptadeca(glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and polyvinylamines.

In a preferred embodiment, a moiety Hyp$^y$ of formula (C-i) is selected from the group comprising, in particular consisting of, in bound form, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid, di(glutamic acid), tri(glutamic acid), tetra(glutamic acid), penta(glutamic acid), hexa(glutamic acid), hepta(glutamic acid), octa(glutamic acid), nona(glutamic acid), deca(glutamic acid), undeca(glutamic acid), dodeca(glutamic acid), trideca(glutamic acid), tetradeca(glutamic acid), pentadeca(glutamic acid), hexadeca(glutamic acid), heptadeca(glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and low-molecular weight PEI.

More preferably, a moiety $Hyp^y$ of formula (C-i) is selected from the group comprising, more preferably consisting of, in bound form, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, and heptadecalysine, even more preferably a moiety $Hyp^y$ of formula (C-i) comprises, preferably consists of, in bound form, trilysine, heptalysine or pentadecalysine.

In a preferred embodiment, a moiety $Hyp^y$ of formula (C-i) has a molecular weight in the range of from 0.1 kDa to 4 kDa, more preferably 0.2 kDa to 2 kDa.

In a further preferred embodiment, each branched moiety $Hyp^y$ of formula (C-i) has at least 1 branching and has at most 63 branchings. More preferably each branched moiety $Hyp^y$ of formula (C-i) has at least 1 branching and has at most 31 branchings.

In a preferred embodiment, $Z^1$ of formula (C-i) comprises a quaternary carbon, in particular a quaternary carbon of a branching core moiety B, wherein B of formula (C-i) is pentaerythritol in bound form. Preferably, each A of formula (C-i) is independently a PEG-based polymeric chain terminally attached to the quaternary carbon of pentaerythritol via the —CH$_2$—O— moieties of the branching core moiety pentaerythritol by a permanent covalent linkage, and the distal end of the PEG-based polymeric chain is covalently bound to a branched moiety $Hyp^y$ of formula (C-i), each branched moiety $Hyp^y$ of formula (C-i) is conjugated to the rest of the prodrug of formula (I).

In one preferred embodiment, a branched moiety $Hyp^y$ of formula (C-i) comprises, preferably consists of branched polyamines comprising at least 2 amine groups. Preferably, the branched polyamine comprising at least 2 amine groups, comprises one or more lysine residues in bound form. Preferably, each branched moiety $Hyp^y$ of formula (C-i) has a molecular weight in the range of from 0.1 kDa to 4 kDa, particular 0.2 to 2 kDa. In a preferred embodiment, a moiety B—(A-$Hyp^y$)$_n$ of formula (C-i), wherein n=4, consist of the same or different branched moieties $Hyp^y$ and that each moiety $Hyp^y$ can be chosen independently. In a preferred embodiment, all moieties $Hyp_y$ of formula (C-i) are the same.

In a preferred embodiment, a moiety $Hyp^y$ of formula (C-i) comprises, in particular consists of, between 1 and 32 lysines in bound form, preferably of 1, 3, 7 or 15 lysines in bound form, more preferably of 1, 3 or 7 lysines in bound form. Most preferably, $Hyp^y$ of formula (C-i) comprises, in particular consists of heptalysinyl.

Preferably, the moiety B—(A-$Hyp^y$)$_n$ of formula (C-i), wherein n is preferably 4, has a molecular weight in the range of from 1 kDa to 160 kDa, more preferably 1 kDa to 80 kDa and even more preferably 10 kDa to 40 kDa.

Preferred moieties B—(A-$Hyp^y$)$_4$ of formula (C-i) are selected from structures (c-i) to (c-iii):

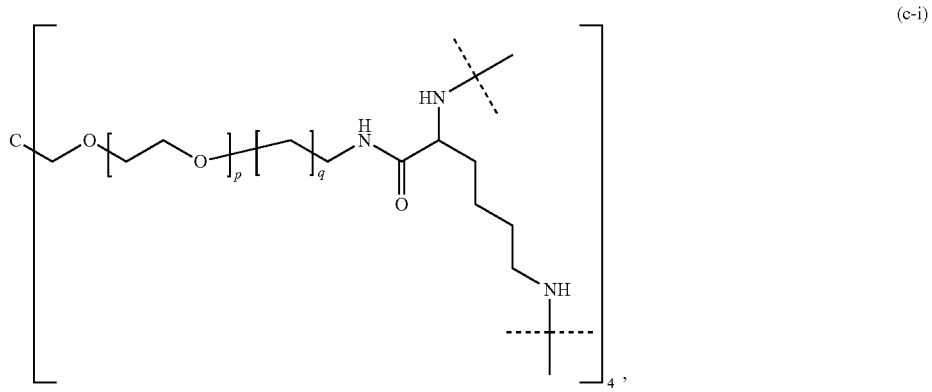

(c-i)

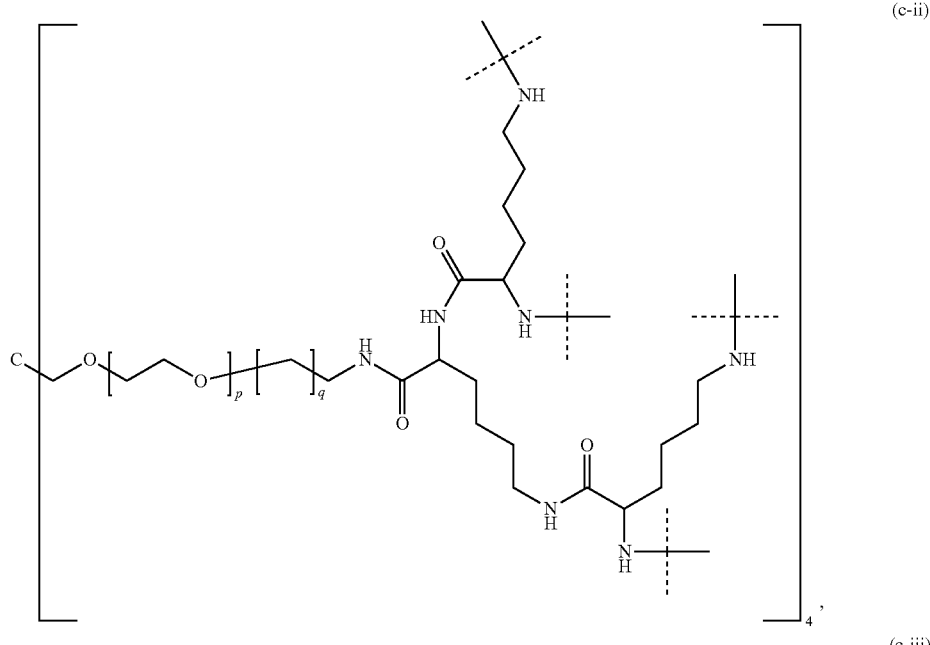
(c-ii)
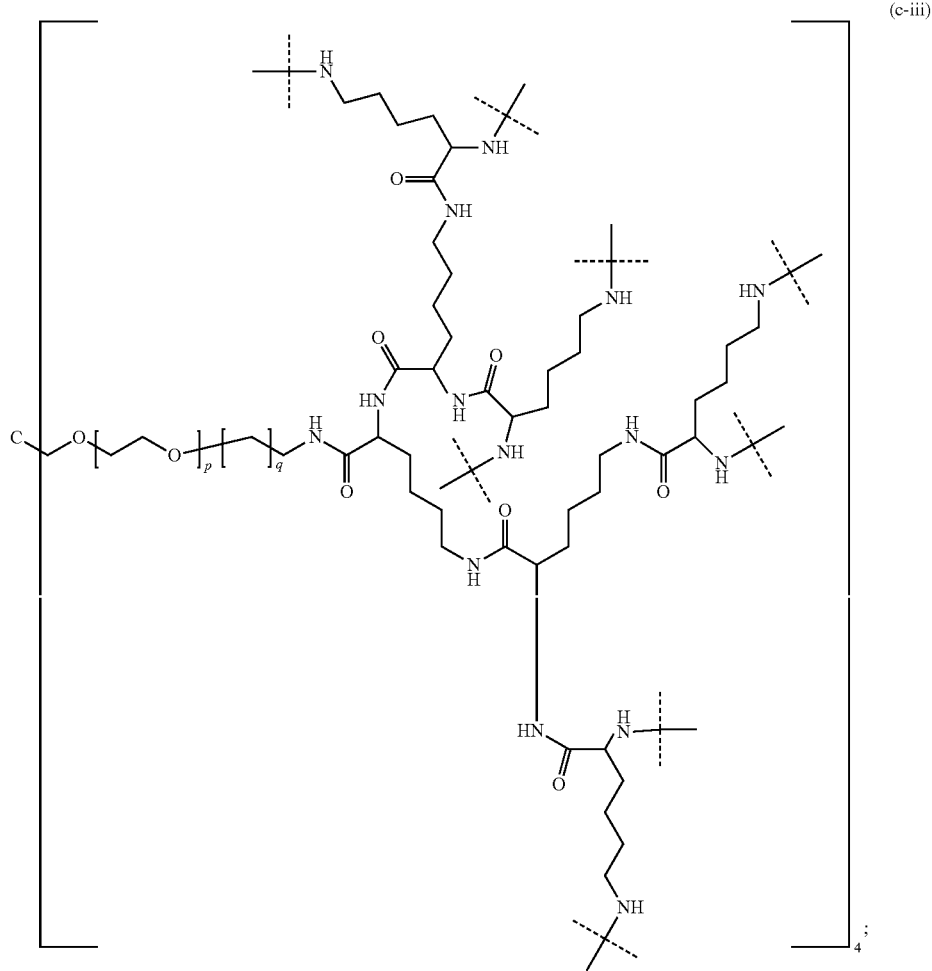
(c-iii)
wherein
dashed lines indicate attachment to the remainder of the prodrug of formula (I),
p is an integer of from 5 to 2000, preferably from 10 to 1000, more preferably from 10 to 500, most preferably from 100 to 1000, q is 1 or 2.

In a preferred embodiment, B of formula (C-i) is pentaerythritol.

In another preferred embodiment $Z^1$ is a carrier as disclosed in WO2013/024049A1, which is herewith incorporated by reference in its entirety. Accordingly, in a preferred embodiment $Z^1$ of formula (I) is a protein carrier which comprises, in particular consists of an amino acid sequence of at least 100 amino acid residues.

Even more preferably, such protein carrier $Z^1$ is in random coil conformation.

In another preferred embodiment, such protein carrier $Z^1$ comprises, in particular consists of alanine, serine and proline residues.

In the preferred embodiment, such protein carrier $Z^1$ of formula (I) comprises, in particular consists of an amino acid sequence of at least 100 amino acid residues, and
wherein the amino acid sequence of at least 100 amino acid residues is in random coil conformation, and,
wherein the amino acid sequence of at least 100 amino acid residues comprises alanine, serine and proline residues.

Preferably, the protein carrier a protein carrier $Z^1$ of formula (I) is composed of an amino acid sequence comprising at least about 100 amino acid residues, at least 100 amino acid residues, consisting of alanine, serine and proline residues which have a random coil conformation at physiological conditions. It is understood that the protein carrier $Z^1$ of formula (I) may transiently or temporarily not form a random coil, for example when present in a lyophilisate or dried composition.

In one embodiment the protein carrier $Z^1$ of formula (I) has a random coil conformation with an amino acid sequence of maximally about 3000 amino acid residues, preferably of maximally about 1500 amino acid residues, more preferably of maximally about 900 amino acid residues, even more preferably of maximally about 700 amino acid residues, particularly preferably of maximally about 600 amino acid residues. Thus, the amino acid sequence forming random coil conformation is maximally about 500 amino acid residues or of maximally about 450 amino acid residues in length.

Accordingly, the protein carrier $Z^1$ of formula (I) in particular the amino acid sequence forming random coil conformation of the protein carrier $Z^1$ of formula (I) is about 100 to about 3000 amino acid residues in length.

In particular embodiments said amino acid sequence forming random coil conformation of about 100 to 1000 amino acid residues is as characterized herein, i.e. comprising alanine, serine and proline as main or unique residues as defined below.

The protein carrier moiety $Z^1$ of formula (I) consists mainly of the three amino acid residues alanine, serine and proline, and wherein all three amino acids are present in a protein carrier moiety $Z^1$ of formula (I), whereby proline residues represent preferably about 4% to about 40% of the protein carrier $Z^1$ of formula (I). The alanine and serine residues preferably comprise the remaining at least 60% to 96% of the protein carrier $Z^1$ of formula (I). However, as will be detailed herein below said protein carrier $Z^1$ of formula (I) may also comprise further amino acids differing from alanine, serine, and proline, i.e. as minor constituents.

The term "minor constituent" as used herein means that maximally 10% (i.e. maximally 10 of 100 amino acids) may be different from alanine, serine and proline, preferably maximally 8% (i.e. maximally 8 of 100 amino acids) may be different than alanine, serine and proline, more preferably maximally 6% (i.e. maximally 6 of 100 amino acids) may be different from alanine, serine and proline, even more preferably maximally 5% (i.e. maximally 5 of 100 amino acids) may be different from alanine, serine and proline, particularly preferably maximally 4% (i.e. maximally 4 of 100 amino acids) may be different from alanine, serine and proline, more particularly preferably maximally 3% (i.e. maximally 3 of 100 amino acids) may be different from alanine, serine and proline, even more particularly preferably maximally 2% (i.e. maximally 2 of 100 amino acids) may be different from alanine, serine and proline and most preferably maximally 1% (i.e. maximally 1 of 100 of the amino acids) that encode the protein carrier $Z^1$ of formula (I) may be different from alanine, serine and proline. Said amino acids different from alanine, serine and proline may be selected from the group of natural or proteinogenic amino-acids consisting of Arg, Asn, Asp, Cys, Gln, Glu, Gly, His, Ile, Leu, Lys, Met, Phe, Thr, Trp, Tyr, and Val. Minor constituents may also be selected from non-naturally occurring amino acids, such as, for example, hydroxyproline or selenomethionine or other modified natural amino acids.

The term "at least about 100/150/200/250/300/300/350 (etc) amino acid residues" is not limited to the concise number of amino acid residues but also comprises amino acid stretches that comprise an additional 10% to 20% or comprise 10% to 20% less residues. For example "at least about 100 amino acid residues" may also comprise 80 to 100 and about 100 to 120 amino acid residues.

In one embodiment, the protein carrier $Z^1$ of formula (I) comprises a plurality of polymer cassettes wherein said polymer cassettes consist of Ala, Ser, and/or Pro, and wherein no more than 6 consecutive amino acid residues of the polymer cassettes, preferably of the protein carrier $Z^1$ of formula (I) are identical and wherein said proline residues constitute more than 4% and less than 40% of the amino acids of said protein carrier $Z^1$ of formula (I).

In one embodiment, the protein carrier moiety $Z^1$ of formula (I) comprises, preferably consists of a plurality of amino acid repeats,
wherein said repeats consist of Ala, Ser, and Pro residues, and wherein no more than 6 consecutive amino acid residues of the carrier moiety $Z^1$ of formula (I) are identical.

In a preferred embodiment, said proline residues constitute more than 4% and less than 40% of the amino acids of the protein carrier moiety $Z^1$ of formula (I).

In a further preferred embodiment, the protein carrier moiety $Z^1$ of formula (I) comprises, in particular consists of an amino acid sequence of about 100 to 3000 amino acid residues forming random coil conformation.

The protein carrier $Z^1$ of formula (I) may comprise a plurality of identical polymer cassettes or a plurality of non-identical polymer cassettes. Non-limiting examples of polymer cassettes consisting of Ala, Ser and/or Pro residues are provided herein below; see SEQ ID NO:9, SEQ ID NO:10, SEQ ID NO:11, SEQ ID NO:12, SEQ ID NO:13 and SEQ ID NO:14 or peptide fragments or multimers of these sequences. A polymer cassette may consist of at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each polymer cassette comprises (an) Ala, Ser, and/or Pro residue(s), preferably (an) Ala, Ser, and Pro residue(s).

In one embodiment, the polymer cassette does not comprise more than 100 amino acid residues. Preferably, a polymer cassette as defined herein comprises more than about 4%, preferably more than about 5%, even more preferably more than about 6%, particularly preferably more than about 8%, more particularly preferably more than about 10%, even more particularly preferably more than about 15% and most preferably more than about 20% proline residues. Such polymer cassette as defined herein preferably comprises less than about 40% or less than about 35% proline residues.

In one embodiment the protein carrier $Z^1$ of formula (I) is of formula (d-i):

$$Ser_x[Ala_y Ser_z]_v \quad (d\text{-}i),$$

which formula further comprises proline residues as defined herein and wherein x is independently selected from integer 0 to 6,
each y is independently selected from integer ranging of from 1 to 6,
each z is independently selected from integer ranging of from 1 to 6.
v is any integer so that the protein carrier $Z^1$ of formula (I) consists of at least about 100 amino acid residues, and in particular of at least about 100 to about 3000 amino acid residues, preferably to about 2000 and more preferably to about 1000 amino acid residues.

In one embodiment, all y of formula (d-i) and z of formula (b) of the v $Ala_y$ $Ser_z$ monomer moieties of formula (d-i) are identical. In another embodiment, the y of formula (d-i) and z of formula (d-i) of the v $Ala_y$ $Ser_z$ monomer moieties of formula (d-i) are different.

In preferred embodiments, the protein carrier $Z^1$ of formula (I) comprises no more than 5 identical consecutive amino acid residues, more preferably no more than 4 identical consecutive amino acid residues and most preferably no more than 3 identical consecutive amino acid residues.

As already indicated herein above, the protein carrier $Z^1$ of formula (I) comprises proline residues, wherein said proline residues constitute more than about 4%, preferably more than about 5%, even more preferably more than about 6%, particularly preferably more than about 8%, more particularly preferably more than about 10%, even more particularly preferably more than about 15% and most preferably more than about 20% of the amino acids constituting the protein carrier $Z^1$ of formula (I) residues may be introduced at any position in formula (d-i). Preferably, the proline residues may be present in one or more of the v $Ala_y$ $Ser_z$ monomers of formula (d-i), and they may be present at the same or at different positions.

In another preferred embodiment, the protein carrier $Z^1$ of formula (I) comprises more than about 4% but less than about 50%, preferably more than about 10% but less than about 50% and most preferably more than about 20% but less than about 50% alanine residues of the amino acids constituting the protein carrier $Z^1$ of formula (I).

In a further preferred embodiment, the protein carrier $Z^1$ of formula (I) comprises more than about 4% and less than about 50%, preferably more than about 10% but less than about 50% and most preferably more than about 20% but less than about 50% serine residues of the amino acids constituting the protein carrier $Z^1$ of formula (I).

Accordingly, the protein carrier $Z^1$ of formula (I) comprises about 35% proline residues, about 50% alanine residues and about 15% serine residues of the amino acids constituting the protein carrier $Z^1$ of formula (I). Alternatively, the protein carrier $Z^1$ of formula (I) may comprise about 35% proline residues, about 15% alanine residues and about 50% serine residues of the amino acids constituting the protein carrier $Z^1$ of formula (I).

Preferably, the protein carrier $Z^1$ of formula (I) comprises one or more of the following alanine-serine polymer cassettes:

AAAASSASSASSSSSAAASA  SEQ ID NO: 1

AASAAASSAAASAAAASASS  SEQ ID NO: 2

ASASASASASASSAASAASA  SEQ ID NO: 3

SAASSSASSSSAASSASAAA  SEQ ID NO: 4

SSSSAASAASAAAAASSSAS  SEQ ID NO: 5

SSASSSAASSSASSSSASAA  SEQ ID NO: 6

SASASASASASAASSASSAS  SEQ ID NO: 7

ASSAAASAAAASSAASASSS  SEQ ID NO: 8 provided that the protein carrier $Z^1$ of formula (I) further comprises proline residues as described herein.

The multimers of these alanine-serine polymer cassettes may form random coil conformation in case the resulting amino acid sequence further comprises proline residues as defined herein above.

In a preferred embodiment, the protein carrier $Z^1$ of formula (I) comprises, preferably consists of one or more of the following polymer cassettes:

ASPAAPAPASPAAPAPSAPA  SEQ ID NO: 9

AAPASPAPAAPSAPAPAAPS  SEQ ID NO: 10

APSSPSPSAPSSPSPASPSS  SEQ ID No: 11

SAPSSPSPSAPSSPSPASPS  SEQ ID NO: 15

SEQ ID NO:15 corresponds to the herein provided SEQ ID NO:11 in a circularly permuted form, wherein the last serine was removed and another serine was appended as starting amino acid. As a consequence, multimers of this modified sequence possess essentially the same internal repeating unit as multimers of the non-modified sequence, except for the very first and the very last residue. Accordingly, SEQ ID NO:15 may be considered as an example of a further polymer cassette for the protein carrier $Z^1$ of formula (I). It is clear for the person skilled in the art that also other polymer cassettes and (shorter) peptide fragments or circularly permuted versions of the herein provided amino acid polymers may be used as polymer cassettes for the protein carrier $Z^1$ of formula (I).

Yet, even further and illustrative amino acid polymers forming random coil conformation may comprise amino acid sequences that may be selected from the group consisting of:

SSPSAPSPSSPASPSPSSPA,  (SEQ ID NO: 12)

AASPAAPSAPPAAASPAAPSAPPA,  (SEQ ID NO: 13)
and

ASAAAPAAASAAASAPSAAA.  (SEQ ID NO: 14)

Therefore, preferred polymer cassettes for $Z^1$ of formula (I) are selected from the following sequences:

ASPAAPAPASPAAPAPSAPA,  (SEQ ID NO: 9)

AAPASPAPAAPSAPAPAAPS,  (SEQ ID NO: 10)

APSSPSPSAPSSPSPASPSS,  (SEQ ID NO: 11)

SSPSAPSPSSPASPSPSSPA,  (SEQ ID NO: 12)

AASPAAPSAPPAAASPAAPSAPPA,  (SEQ ID NO: 13)
and

ASAAAPAAASAAASAPSAAA;  (SEQ ID NO: 14)

or circular permuted versions or (a) multimer(s) of these sequences as a whole or parts of these sequences.

In one embodiment, the protein carrier moiety $Z^1$ of formula (I) comprises at least one amino acid sequence selected from the group consisting of:

ASPAAPAPASPAAPAPSAPA,  (SEQ ID NO: 9)

AAPASPAPAAPSAPAPAAPS,  (SEQ ID NO: 10)

APSSPSPSAPSSPSPASPSS,  (SEQ ID NO: 11)

SSPSAPSPSSPASPSPSSPA,  (SEQ ID NO: 12)

AASPAAPSAPPAAASPAAPSAPPA,  (SEQ ID NO: 13)
and

ASAAAPAAASAAASAPSAAA;  (SEQ ID NO: 14)

and circular permuted versions or (a) multimer(s) of these sequences as a whole or parts of these sequences.

Again, also (a) peptide fragment(s) or (a) multimer(s) or circularly permuted versions of these sequences and the sequences provided herein above may be employed as polymer cassettes for the protein carrier $Z^1$ of formula (I).

Accordingly, the exemplified polymer cassettes may also provide for individual peptide fragments which may be newly combined to form further polymer cassettes.

In accordance with the above, the protein carrier $Z^1$ of formula (I) may comprise a multimer consisting of either one of the amino acid sequences with SEQ ID NO:9, 10, 11, 12, 13 or 14 as disclosed herein above or may comprise a multimer consisting of more than one of amino acid sequences SEQ ID NO:9, 10, 11, 12, 13 and 14. Furthermore, it is envisaged that also peptide fragments or circularly permuted versions of these exemplified sequences may be used to build up further polymer cassettes of the protein carrier $Z^1$ of formula (I).

In another embodiment, the protein carrier $Z^1$ of formula (I) may comprise a multimer comprising, preferably consisting of a (circular) permutation of the amino acid sequence selected from the group consisting of SEQ ID NOs:9, 10, 11, 12, 13, 14, 15 and (a) multimers(s) of these (circular) permutated sequences.

In yet another embodiment, the protein carrier $Z^1$ of formula (I) may comprise, preferably consist of a multimer consisting of a peptide fragment/part of the amino acid sequence selected from the group consisting of SEQ ID NO: 9, 10, 12, 13, 14, 15 and (a) multimers(s) of these exemplified polymer cassettes.

Peptide fragments of these sequences to be employed for the generation of the protein carrier $Z^1$ of formula (I) may consist of at least 3, preferably of at least 4, more preferably of at least 5, even more preferably of at least 6, still more preferably of at least 8, particularly preferably of at least 10, more particularly preferably of at least 12, even more particularly preferably of at least 14, preferably of at least 6, still more preferably of at least 8, particularly preferably of at least 10, more particularly preferably of at least 12, even more particularly preferably of at least 14, even more particularly preferably of at least 16, and most preferably of at least 18 consecutive amino acids of the amino acid sequence selected from the group consisting of said SEQ ID NOs: 9, 10, 11, 12, 13 and 14.

For example, individual peptide fragments of the polymer cassettes may be combined to further individual polymer cassettes as long as the above-identified rules for the overall distribution and amount of alanine, serine and proline are respected. Again, these polymer cassettes may also comprise further amino acid residues, however only as minimal or minor constituents, i.e. maximally 10%, preferably maximally 2% of the individual polymer cassette. Said individual polymer cassettes consist of at least about 100 amino acid residues. Individual polymer cassettes may be combined in order to form longer random coil forming amino acid polymers, whereby a maximal length of the protein carrier $Z^1$ of formula (I), (II), (IIaa), (IIab), (IIac), (IIad), (IIb) or (IIba) is about 3000 amino acids. A preferred minor constituent of the protein carrier $Z^1$, (II), (IIaa), (IIab), (IIac), (IIad), (IIb) or (IIba) is lysine.

In another embodiment the carrier $Z^1$ has the structure of formula (A-iv):

$$B\text{---}(A)_q \quad \text{(A-iv)},$$

wherein
B is branching core,
each A is independently a PEG-based polymeric chain, and
q is an integer of from 3 to 64.

Preferably, q of formula (A-iv) and y of formula (I) have the same value.

Preferably, q is 2, 4, 6, 8, 10, 12, 14, 16, 20, 24, 32, or 48. More preferably, q is 2, 4, 6, 8, 10 or 16; even more preferably, q is 2, 4, 6 or 8 and most preferably, q is 4.

In a preferred embodiment, the branching core B of formula (A-iv) comprises, preferably consists of a moiety selected from:
a polyalcohol comprising at least 2 hydroxyl groups (preferably further comprising a functional group, which is preferably an additional amino group or a carboxylic acid group, more preferably an additional carboxylic acid group), preferably B is selected from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans, erythritol, threitol, arabitol, xylitol, ribitol, dulcitol, iditol; more preferably from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans.

or a polyamine comprising at least 2 amine groups (preferably further comprising a functional group, which is preferably an additional hydroxyl group or a carboxylic acid group, more preferably a carboxylic acid group), preferably selected from ornithine, diornithine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, diaminobutyric acid, di(diaminobutyric acid), tri(diaminobutyric acid), tetra (diaminobutyric acid), penta(diaminobutyric acid), hexa(diaminobutyric acid), hepta(diaminobutyric acid), octa(diaminobutyric acid), nona(diaminobutyric acid), deca(diaminobutyric acid), undeca(diaminobutyric acid), dodeca(diaminobutyric acid), trideca(diaminobutyric acid), tetradeca(diaminobutyric acid), pentadeca(diaminobutyric acid), hexadeca(diaminobutyric acid), heptadeca(diaminobutyric acid), octadeca (diaminobutyric acid), nonadeca(diaminobutyric acid), lysine, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, oligo lysines, polyethyleneimines, and polyvinylamines;

wherein the polyalcohol or polyamine is in bound form.

In a preferred embodiment, the branching core B of formula (A-iv) comprises pentaerithritol.

Preferably, a poly(ethylene glycol)-based polymeric chain A connected to the branching core B of formula (A-iv) consists of a linear PEG chain, of which one terminus is connected to B and the other terminus is connected to $X^0$ of formula (I).

It is understood that a PEG-based chain A of formula (A-iv) may optionally be terminated in case of a branched PEG chain and/or may optionally be interrupted in case of a branched or linear PEG chain by alkyl or aryl groups and may optionally be substituted with heteroatoms and/or functional groups.

Preferably, the carrier $Z^1$ of formula (A-iv) is a multi-arm PEG derivative as, for instance, detailed in the products list of JenKem Technology, USA, such as a 4-arm-PEG derivative, in particular comprising a pentaerythritol core, an 8-arm-PEG derivative comprising a hexaglycerin core, and an 8-arm-PEG derivative comprising a tripentaerythritol core. More preferred are sub-structures B—(A)$_n$ of formula (A-iv) comprising, in particular consisting of, moieties selected from:

a 4-arm PEG Amine comprising a pentaerythritol core:

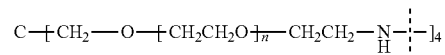

with n ranging from 20 to 500;
an 8-arm PEG Amine comprising a hexaglycerin core:

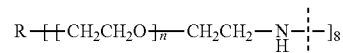

with n ranging from 20 to 500; and
R=hexaglycerin core structure;
an 8-arm PEG Amine comprising a tripentaerythritol core:

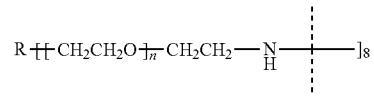

with n ranging from 20 to 500;
and R=tripentaerythritol core structure;
a 6-arm PEG Amine comprising a sorbitol or dipentaerythritol core:

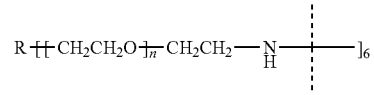

with n ranging from 20 to 500; and
R=sorbitol or dipentaerythritol;
a 6-arm PEG Amine comprising a sorbitol or dipentaerythritol core:

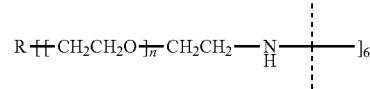

with n ranging from 20 to 500;
and R=sorbitol or dipentaerythritol;
a 4-arm PEG Amine comprising a pentaerythritol core:

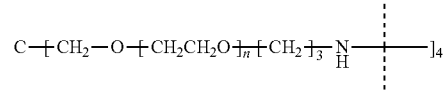

with n ranging from 20 to 500;
an 8-arm PEG Amine comprising a hexaglycerin core:

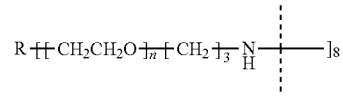

with n ranging from 20 to 500; and

R=hexaglycerin core structure;
an 8-arm PEG Amine comprising a tripentaerythritol core:

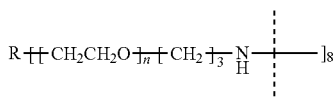

with n ranging from 20 to 500;
and R=tripentaerythritol core structure;
a 6-arm PEG Amine comprising a sorbitol or dipentaerythritol core:

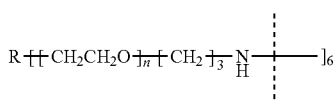

with n ranging from 20 to 500; and
R=comprising a sorbitol or dipentaerythritol core;
a 6-arm PEG Amine comprising a sorbitol or dipentaerythritol core:

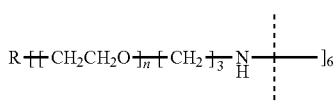

with n ranging from 20 to 500;
and R=comprising a sorbitol or dipentaerythritol core;
wherein dashed lines indicate attachment points to $X^0$ of formula (I).

If the carrier-linked prostanoid prodrug is of formula (I), (Ica) or (Icb), then more preferred sub-structures $B(-A)_n$ of formula (A-iv) comprise moieties selected from:
a 4-arm PEG Carboxyl comprising a pentaerythritol core:

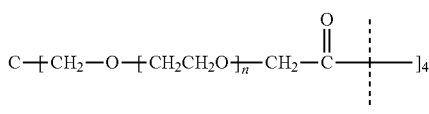

with n ranging from 20 to 500;
an 8-arm PEG Carboxyl comprising a hexaglycerin core:

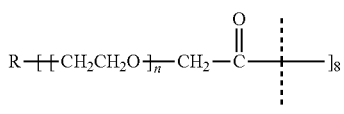

with n ranging from 20 to 500; and
R=hexaglycerin core structure;
an 8-arm PEG Carboxyl comprising a tripentaerythritol core:

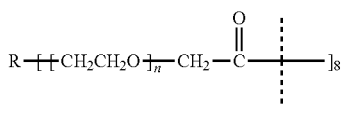

with n ranging from 20 to 500; and

R=tripentaerythritol core structure;
a 6-arm PEG Carboxyl comprising a sorbitol or dipentaerythritol core:

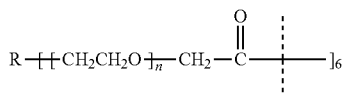

with n ranging from 20 to 500; and
R=sorbitol or dipentaerythritol;
a 6-arm PEG Carboxyl comprising a sorbitol or dipentaerythritol core:

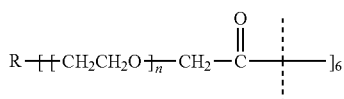

with n ranging from 20 to 500; and
R=sorbitol or dipentaerythritol;
a 4-arm PEG Carboxyl comprising a pentaerythritol core:

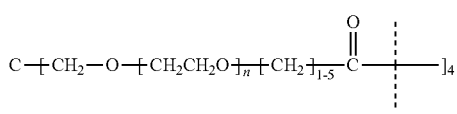

with n ranging from 20 to 500;
an 8-arm PEG Carboxyl comprising a hexaglycerin core:

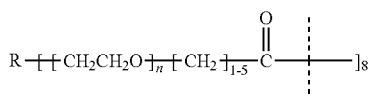

with n ranging from 20 to 500; and
R=hexaglycerin core structure;
and an 8-arm PEG Carboxyl comprising a tripentaerythritol core:

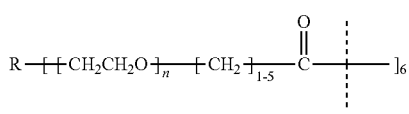

with n ranging from 20 to 500; and
R=tripentaerythritol core structure;
a 6-arm PEG Carboxyl comprising a sorbitol or dipentaerythritol core:

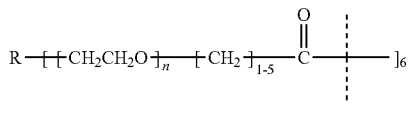

with n ranging from 20 to 500; and
R=comprising a sorbitol or dipentaerythritol core;
and a 6-arm PEG Carboxyl comprising a sorbitol or dipentaerythritol core:

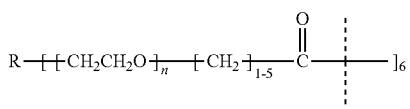

with n ranging from 20 to 500; and

R=comprising a sorbitol or dipentaerythritol core;
wherein dashed lines indicate attachment points to $X^0$ of formula(I).

In a preferred embodiment, the molecular weight of the carrier of formula (A-iv) ranges from 1 kDa to 80 kDa, more preferably 1 kDa to 40 kDa and even more preferably 10 kDa to 40 kDa.

More preferably, the carrier $Z^1$ has the structure of formula (A-iva):

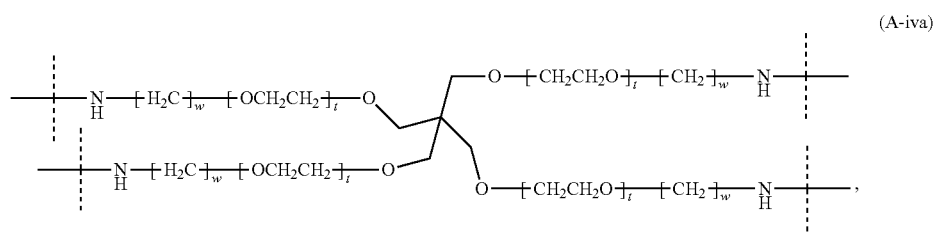

(A-iva)

wherein
dashed lines indicate attachment points to $X^0$;
t is an integer ranging from 80 to 160; and
w is an integer ranging from 2 to 6.

Preferably, w of formula (A-iva) is 2 or 3.

Most preferably, the carrier-linked prostanoid prodrug has the structure of formula (III):

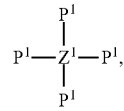

(III)

wherein
$Z^1$ has the structure

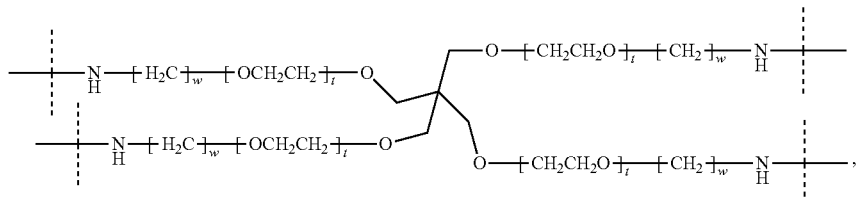

wherein
dashed lines indicate attachment points to $P^1$,
t is an integer ranging from 80 to 160; and
w is 2 or 3;

each moiety $P^1$ has the structure

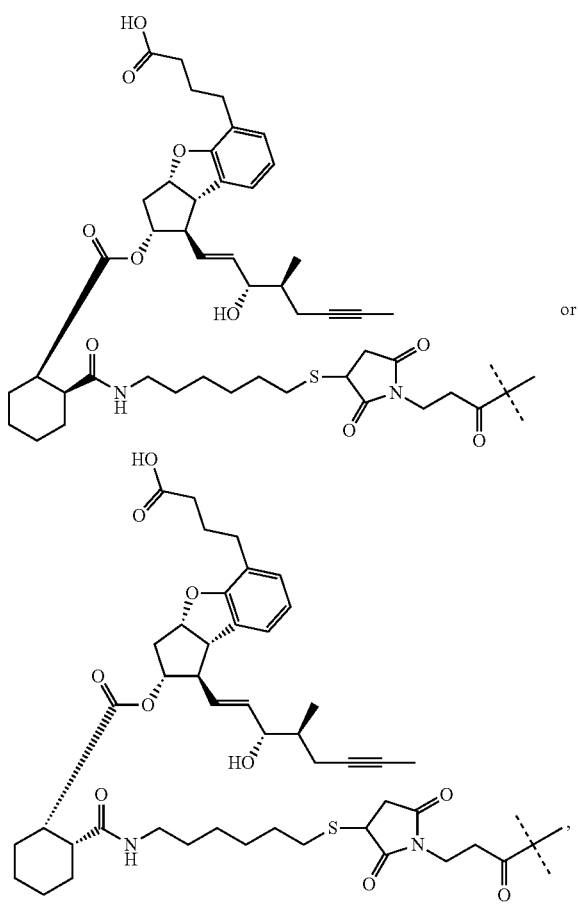

wherein dashed lines indicate the attachment point to $Z^1$.

In another embodiment, the present invention relates to a pharmaceutical composition comprising one or more of the carrier-linked prostanoid prodrug(s) or a pharmaceutically acceptable salt thereof of the present invention, optionally together with one or more pharmaceutically acceptable excipients.

Preferably, the pharmaceutical composition is characterized in that the carrier-linked prostanoid prodrug releases prostanoid in a plasma-independent manner. Preferably, the carrier-linked prostanoid prodrug releases prostanoid in an enzyme-independent manner.

The term "plasma-independent" means that the release kinetics of prostanoid from the carrier-linked prostanoid prodrug measured at 37° C. independently in buffer at pH 7.4 and in 80% buffered plasma at pH 7.4 varies by no more than 50%, preferably by no more than 40%, more preferably by no more than 30%, even more preferably by no more than 20% and most preferably by no more than 10%. It is understood that the release kinetics of prostanoid from the carrier-linked prostanoid prodrug measured in 80% buffered plasma at pH 7.4 and 37° C. may increase or decrease compared to measurements in buffer at pH 7.4 and 37° C. Preferably, the release kinetics of prostanoid from the carrier-linked prostanoid prodrug does not decrease in 80% buffered plasma at pH 7.4 and 37° C. compared to buffer at pH 7.4 and 37° C.

The term "enzyme-independent" means that the release of prostanoid from the carrier-linked prostanoid prodrug does not require the presence of enzymes.

The pharmaceutical composition is further described in the following paragraphs.

The pharmaceutical composition comprising the carrier-linked prostanoid prodrug of the present invention may be provided as a liquid composition or as a dry composition. Suitable methods of drying are, for example, spray-drying and lyophilization (freeze-drying). A preferred method of drying is lyophilization.

In one embodiment of the present invention, the liquid or dry pharmaceutical composition comprising the carrier-linked prostanoid prodrug is provided as a single dose, meaning that the container in which it is supplied contains one pharmaceutical dose.

Alternatively, the liquid or dry pharmaceutical composition comprising the carrier-linked prostanoid prodrug is a multiple dose composition, meaning that the container in which it is supplied contains more than one therapeutic dose, i.e., a multiple dose composition contains at least 2 doses. Such multiple dose composition of carrier-linked prostanoid prodrug can either be used for different patients in need thereof or can be used for one patient, wherein the remaining doses are stored after the application of the first dose until needed.

Preferably, the carrier-linked prostanoid prodrug is sufficiently dosed in the composition to provide a therapeutically effective amount of prostanoid for at least 12 hours in one application. More preferably, one application of the pharmaceutical composition comprising the carrier-linked prostanoid prodrug is sufficient for at least 1 day, such as two days, three days, four days, five days, six days, or seven days, such as two weeks, three weeks or four weeks.

In one embodiment, the present invention relates to a pharmaceutical composition
(i) wherein the carrier-linked prostanoid prodrug of the present invention is sufficiently dosed in the pharmaceutical composition to provide a therapeutically effective amount of prostanoid for at least 12 hours in one application, and/or
(ii) wherein a single dose of the pharmaceutical composition comprises about 2 to about 6, preferably about 4 mg prostanoid.

In a preferred embodiment, the a single dose of a liquid pharmaceutical composition of the present invention has a volume of about 0.1 to about 10 ml, preferably about 0.5 to about 5 ml, even more preferably about 0.5 to about 2 ml, in particular about 1 ml.

"About" according to the present invention is understood as meaning the experimental error range, in particular ±5% or ±10%.

The excipients of the pharmaceutical composition may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The pharmaceutical compositions of carrier-linked prostanoid prodrugs according to the present invention contain one or more excipients, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability (ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum (iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride (iv) Stabilizers: Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used (v) Anti-adsorption agents: Mainly ionic or non-ionic surfactants or other proteins or soluble polymers are used to coat or adsorb competitively to the inner surface of the composition's or composition's container. Suitable surfactants are e.g., alkyl sulfates, such as ammonium lauryl sulfate and sodium lauryl sulfate; alkyl ether sulfates, such as sodium laureth sulfate and sodium myreth sulfate; sulfonates such as dioctyl sodium sulfosuccinates, perfluorooctanesulfonates, perfluorobutanesulfonates, alkyl benzene sulfonates; phosphates, such as alkyl aryl ether phosphates and alkyl ether phosphates; carboxylates, such as fatty acid salts (soaps) or sodium stearate, sodium lauroyl sarcosinate, perfluorononanoate, perfluorooctanoate; octenidine dihydrochloride; quaternary ammonium cations such as cetyl trimethylammonium bromide, cetyl trimethylammonium chloride, cetylpyridinium chloride, polyethoxylated tallow amine, benzalkonium chloride, benzethonium chloride, 5-bromo-5-nitor-1,3-dioxane, dimethyldioctadecylammonium chloride, dioctadecyldimethylammonium bromide; zwitterionics, such as 3-[(3-cholamidopropyl)dimethylammonio]-1-propanesulfonate, cocamidopropyl hydroxysultaine, amino acids, imino acids, cocamidopropyl betaine, lecithin; fatty alcohols, such as cetyl alcohol, stearyl alcohol, cetostearyl alcohol, oleyl alcohol; polyoxyethylene glycol alkyl ethers, such as octaethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers such as Triton X-100; polyoxyethylene glycol alkylphenol ethers such as nonoxynol-9; glycerol alkyl esters such as glyceryl laurate; polyoxyethylene glycol sorbitan alkyl esters such as polysorbates; sorbitan alkyl esters; cocamide MEA and cocamide DEA; dodecyl dimethylamine oxide; block copolymers of polyethylene glycol and polypropylene glycol, such as poloxamers (Pluronic F-68), PEG dodecyl ether (Brij 35), polysorbate 20 and 80; other anti-absorption agents are dextran, polyethylene glycol, PEG-polyhistidine, BSA and HSA and gelatines. Chosen concentration and type of excipient depends on the effect to be avoided but typically a monolayer of surfactant is formed at the interface just above the CMC value (vi) Lyo- and/or cryoprotectants: During freeze- or spray drying, excipients may counteract the destabilizing effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid (viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(ix) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

In another aspect of the present invention the pharmaceutical composition is in a container. Suitable containers for liquid or dry compositions are, for example, syringes, vials, vials with stopper and seal, ampoules, and cartridges. In particular, the liquid or dry composition comprising the carrier-linked prostanoid prodrug according to the present invention is provided in a syringe. If the pharmaceutical composition comprising the carrier-linked prostanoid prodrug is a dry pharmaceutical composition the container preferably is a dual-chamber syringe. In such embodiment, said dry pharmaceutical composition is provided in a first chamber of the dual-chamber syringe and reconstitution solution is provided in the second chamber of the dual-chamber syringe.

Prior to applying a dry composition of carrier-linked prostanoid prodrug to a patient in need thereof, the dry composition is reconstituted. Reconstitution can take place in the container in which the dry composition of carrier-linked prostanoid prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials, such as, for example, benzyl alcohol and cresol. Preferably, the reconstitution solution is sterile water. When a dry composition is reconstituted, it is referred to as a "reconstituted pharmaceutical composition" or "reconstituted composition".

Another aspect of the present invention is a carrier-linked prostanoid prodrug or pharmaceutically acceptable salt thereof or the pharmaceutical composition of the present invention for use as a medicament.

Another aspect of the present invention is a carrier-linked prostanoid prodrug or a pharmaceutically acceptable salt thereof or the pharmaceutical composition of the present invention for use in a method of treating, controlling, delaying or preventing a disease that can be treated, controlled, delayed or prevented by prostanoid.

Preferably, the disease is selected from pulmonary hypertension, ischemic diseases (e.g. peripheral vascular disease including peripheral arterial disease, Raynaud's phenomenon including Raynaud's disease and Raynaud's syndrome, scleroderma including systemic sclerosis, myocardial ischemia, ischemic stroke, renal insufficiency), ischemic ulcers including digital ulcers, heart failure (including congestive heart failure), portopulmonary hypertension, interstitial lung disease, idiopathic pulmonary fibrosis, conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation and other emerging therapeutic areas where prostacyclin treatment appears to have a beneficial role, preferably pulmonary arterial hypertension.

Most preferably, the carrier-linked prostanoid prodrug or a pharmaceutically acceptable salt thereof or the pharmaceutical composition of the present invention is used in a method of treating, controlling, delaying or preventing pulmonary arterial hypertension.

Yet another aspect is the use of a carrier-linked prostanoid prodrug or a pharmaceutically acceptable salt thereof or the pharmaceutical composition of the present invention in the preparation of a medicament for of treating, controlling, delaying or preventing a disease that can be treated, controlled, delayed or prevented by prostanoid, like diseases and preferred disease as mentioned above.

Another aspect of the present invention is a method of treating, controlling, delaying or preventing in a mammalian patient, preferably in a human, in need of the treatment of one or more diseases that can be treated, controlled, delayed or prevented by prostanoid, like diseases and preferred disease as mentioned above, comprising administering to said patient a therapeutically effective amount of a carrier-linked prostanoid prodrug or a pharmaceutically acceptable salt thereof or the pharmaceutical composition of the present invention.

In another aspect the prodrug, pharmaceutically acceptable salt thereof or pharmaceutical composition of the present invention for use as a medicament or in a method of treating, controlling, delaying or preventing is administered by inhalation; topical, enteral, parenteral, intraarticular, intradermal, subcutaneous, intramuscular, intravenous, intraosseous, intraperitoneal, intrathecal, intracapsular, intraorbital, intracardiac, transtracheal, subcuticular, intraarticular, subcapsular, subarachnoid, intraspinal, intraventricular or intrasternal administration. Preferably, the administration is by subcutaneous, intramuscular or intravenious injection or infusion, most preferably, by subcutaneous injection or infusion.

Accordingly, another aspect of the present invention is the use of a prodrug, pharmaceutically acceptable salt thereof or pharmaceutical composition of the present invention in the preparation of a medicament for treating, controlling, delaying or preventing which is administered by inhalation; topical, enteral, parenteral, intraarticular, intradermal, subcutaneous, intramuscular, intravenous, intraosseous, intraperitoneal, intrathecal, intracapsular, intraorbital, intracardiac, transtracheal, subcuticular, intraarticular, subcapsular, subarachnoid, intraspinal, intraventricular or intrasternal administration. Preferably, the administration is by subcutaneous, intramuscular or intravenious injection or infusion, most preferably, by subcutaneous injection or infusion.

Accordingly, another aspect of the present invention is a method of treating, controlling, delaying or preventing in a mammalian patient, preferably in a human, in need of the treatment of one or more diseases that can be treated, controlled, delayed or prevented by prostanoid, like diseases and preferred disease as mentioned above, comprising administering to said patient a therapeutically effective amount of a carrier-linked prostanoid prodrug or a pharmaceutically acceptable salt thereof or the pharmaceutical composition of the present invention, wherein the therapeutically effective amount of a carrier-linked prostanoid prodrug or a pharmaceutically acceptable salt thereof or the pharmaceutical composition of the present invention is administered by inhalation; topical, enteral, parenteral, intraarticular, intradermal, subcutaneous, intramuscular, intravenous, intraosseous, intraperitoneal, intrathecal, intracapsular, intraorbital, intracardiac, transtracheal, subcuticular, intraarticular, subcapsular, subarachnoid, intraspinal, intraventricular or intrasternal administration. Preferably, the administration is by subcutaneous, intramuscular or intravenious injection or infusion, most preferably, by subcutaneous injection or infusion A preferred aspect of the present invention is a method of treating pulmonary hypertension, comprising administering to a subject in need thereof an effective amount of the carrier-linked prostanoid prodrug or a pharmaceutically acceptable salt thereof of the present invention to a subject in need thereof. Preferably, in such carrier-linked prostanoid prodrug of the present invention the moiety PG0 is a beraprost moiety, i.e. is of formula (i-c).

The preferred method of administration of a dry pharmaceutical composition comprising the carrier-linked prostanoid prodrug or pharmaceutically acceptable salt thereof of the present invention is by inhalation.

In another embodiment, a first carrier-linked prostanoid prodrug or the pharmaceutically acceptable salt thereof or the pharmaceutical composition thereof of the present invention is administered via a first method of administration and a second carrier-linked prostanoid prodrug of the present invention is administered via a second method of administration, either simultaneously or consecutively. Said first and second method of administration can be any combination of inhalation; topical, enteral, parenteral, intraarticular, intradermal, subcutaneous, intramuscular, intravenous, intraosseous, intraperitoneal, intrathecal, intracapsular, intraorbital, intracardiac, transtracheal, subcuticular, intraarticular, subcapsular, subarachnoid, intraspinal, intraventricular or intrasternal administration.

In another embodiment, the carrier-linked prostanoid prodrug of the present invention is administered together with one or more additional drug(s). The additional one or more drug(s) is preferably selected from the group comprising cardiovascular agents such as a prostacyclin or prostaglandin; mediators of NO activity; calcium channel blocker; phosphodiesterase inhibitors; diuretics; endothelial antagonists; or antiplatelet agents. It is preferred that the one or more additional drug(s) and the carrier-linked prostanoid prodrug of the present invention are administered in a fixed dose combination.

In another embodiment, the carrier-linked prostanoid prodrug or the pharmaceutically acceptable salt thereof or the pharmaceutical composition of the present invention is administered in combination with an inhaled prostanoid.

In case the carrier-linked prostanoid prodrugs according to the invention contain one or more acidic or basic groups, the invention also comprises their corresponding pharmaceutically acceptable salts, in particular their pharmaceutically utilizable salts. Thus, the carrier-linked prostanoid prodrugs according to the invention which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Carrier-linked prostanoid prodrugs according to the invention which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the carrier-linked prostanoid prodrugs according to the invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

Another aspect of the present invention is a method for the synthesis of a carrier-linked prostanoid prodrug or a pharmaceutically acceptable salt thereof of the present invention. Carrier-linked prostanoid prodrugs or precursors of such prodrugs according to the present invention may be prepared by known methods or in accordance with the reaction sequences described below. The starting materials used in the synthesis of carrier-linked prostanoid prodrugs of the invention or precursors thereof are known or commercially available, or can be prepared by known methods or as described below.

All reactions for the synthesis of the carrier-linked prostanoid prodrugs according to the present invention including precursors are per se well-known to the skilled person and can be carried out under standard conditions according to or analogously to procedures described in the standard literature of organic chemistry. Depending on the circumstances of the individual case, in order to avoid side reactions during the synthesis of a carrier-linked prostanoid prodrug or a precursor thereof, it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the carrier-linked prostanoid prodrugs or precursors thereof can be purified by customary purification procedures, for example by recrystallization or chromatography.

In one embodiment, the carrier-linked prostanoid prodrugs according to the present invention or a pharmaceutically acceptable salt thereof may be prepared by a method comprising the steps of converting the carboxylic acid of the prostanoid P to a prostanoid moiety reagent P—Y, wherein Y is a leaving group, and subsequently reacting the reagent P—Y with a hydroxyl-group containing reversible prodrug linker reagent $X^0$—OH, thus generating a prostanoid moiety-reversible prodrug linker conjugate $PG^0$-$X^0$ by forming a carboxylic ester linkage. Afterwards, $PG^0$-$X^0$ may be bound to a carrier moiety $Z^1$ to obtain the carrier-linked prostanoid prodrug of a biologically active moiety comprising a carboxylic acid group according to the present invention. Alternatively, the carrier moiety $Z^1$ may already be bound to $X^0$—OH. Alternatively, a moiety $PG^0$-$X^0$ can be reacted with the reactive functional groups of $Z^1$. Alternatively, a reagent comprising a moiety $Z^1$—$X^0$ may be prepared for subsequent reaction with a preferentially activated biologically active acid P—Y. It is understood that P is a prostanoid.

A further method for the preparation may comprise the steps of
reacting the prostanoid $PG^0$-OH with a linker HOOC—$X^{0'}$ to form $PG^0$-$L^0$-$X^{0'}$; and
further reacting $PG^0$-$L^0$-$X^{0'}$ with a carrier $X^{0''}_y Z^1$ to form a prodrug of formula (I), wherein $X^{0'}$ and $X^{0''}$ are reacted to give $X^0$.

It is understood that functional groups of prostanoid not involved in the synthesis of the carrier-linked prostanoid prodrugs of the present invention may be protected with suitable protecting groups known to the person skilled in the art.

Suitable leaving groups are known to a person skilled in the art. Preferably, if attached to P, Y is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysulfosuccinimidyl.

A suitable protecting group may be 2,4-dimethoxybenzyloxy group for protecting a carboxylic acid group and trityl for protecting a thiol group.

Materials, Methods and Analytics:
Chemicals and Drug Substances:
Beraprost was obtained from Lung LLC. Cis-cyclohexanedicarboxylic anhydride was purchased from Alfa Aesar GmbH & Co KG, Karlsruhe, Germany. 6-(S-Tritylsulfanyl)-hexaneamine was synthesized according to WO-A 2009/133137. PEGs used in this work were acquired from NOF Europe N. V., Grobbendonk, Belgium. All other chemicals were purchased from Sigma Aldrich GmbH, Taufkirchen, Germany, Roth, Karlsruhe, Germany or Nova Biochem, Darmstadt, Germany. Water and acetonitrile for analytical RP-HPLC were purchased from Biosolve B. V. and TFA from Thermo scientific. Water and acetonitrile for preparative HPLC were purchased from Roth or J. T. Baker, respectively. Wistar rat plasma was obtained from Innovative Research, Product Purification Normal phase purification was performed on a Biotage "Isolera four" purification system Biotage AB, Sweden. Biotage KP-Sil silica cartridges were used as stationary phase: gradients of n-heptane and ethyl acetate were applied. Products were detected and collected at 254 and 280 nm.

For preparative RP-HPLC, a Waters 600 controller and a 2487 Dual Absorbance Detector was used equipped with a Waters XBridge™ BEH300 Prep C18 5 µm, 150×10 mm, flow rate 6 ml/min, or Waters XBridge™ BEH300 Prep C18 10 µm, 150×30 mm, flow rate 40 ml/min. Gradients of eluents A (water containing 0.05 TFA v/v or 0.01% HCl v/v) and B (acetonitrile containing 0.05 TFA v/v or 0.01% HCl v/v) were used.

LC/MS Analytics

Analytical RP-HPLC/ESI-MS was performed on a Waters Acquity UPLC (flow: 0.25 mL/min; solvent A: UP-H$_2$O+ 0.04% TFA, solvent B: UP-Acetonitrile+0.05% TFA) with an Acquity PDA detector and a ZQ 4000 ESI instrument. The following stationary phases were used: Waters ACQUITY UPLC BEH300 C18 RP column (2.1×50 mm, 300 Å, 1.7 µm), Thermo Scientific Hypersil GOLD PFP (2.1×50 mm, 1.9 µm particle size), Phenomenex Kinetex XB C-18 100 A (2.1×100 mm, 1.7 µm particle size). UPLC-MS/MS was performed on an Agilent 1290 UPLC equipped with a Waters Acquity C18 column (2.1×100 mm, 1.7 µm particle size), coupled to an Agilent QQQ 6460 (Software Masshunter).

EXAMPLE 1

Synthesis of Dmob Protected Beraprost 1b

N,O-bis(trimethylsilyl)-acetamide (0.6 mL, 2.45 mmol, 10.7 eq) was added to a THF solution (0.63 mL) of beraprost potassium salt (100 mg, 0.229 mmol, 1 eq) at room temperature. The reaction mixture was stirred at room temperature for 20 h. TLC analysis (silica, eluents n-heptane/ethyl acetate 1:2, v/v)) confirmed full conversion. The reaction mixture was then diluted with ethyl acetate (10 mL), washed twice with a saturated aqueous solution of NaHCO$_3$ (10 mL each) and once with brine (7 mL). The organic phase was dried over Na$_2$SO$_4$ and concentrated under reduced pressure. The resulting crude 1a (approx. 200 mg) was then dissolved in dichloromethane (2.5 mL). 2,4-dimethylbenzylic alcohol (65 mg, 0.389 mmol, 1.7 eq), DMAP (25 mg, 0.206 mmol, 0.9 eq) and EDC.HCl (66 mg, 0.343 mmol, 1.5 eq) were successively added and the slightly turbid mixture was stirred at room temperature for 14 h. The reaction mixture was diluted with ethyl acetate (15 mL) and washed with 0.1 M HO/brine (6:1, v/v, 15 mL), 0.1 M HCl (10 mL) and brine (10 mL). A solution of citric acid in methanol (4:96, w/w, 7 mL) was added to the organic phase and the resulting mixture was stirred at r.t. for 12 min. TLC analysis (silica, eluents n-heptane/ethyl acetate 1:2 (v/v)) confirmed full deprotection of the hydroxyl groups. The solution was washed with a 5% aqueous NaCl solution (10 and 7 mL), dried over Na$_2$SO$_4$ and concentrated under reduced pressure. The crude product was purified by automated flash chromatography.

Yield: 105 mg (0.191 mmol, 84%).

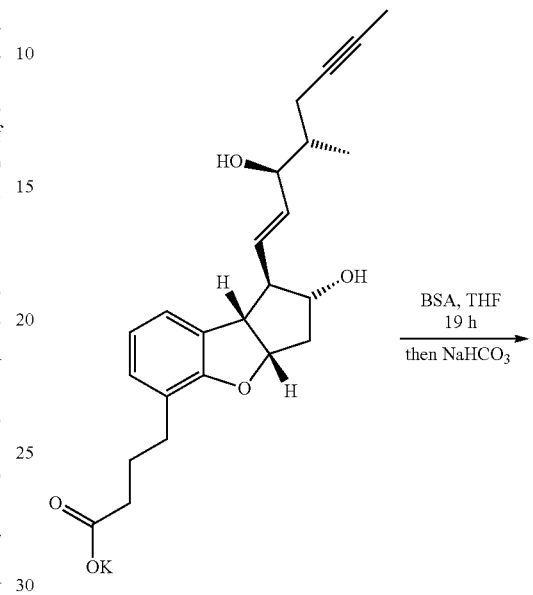

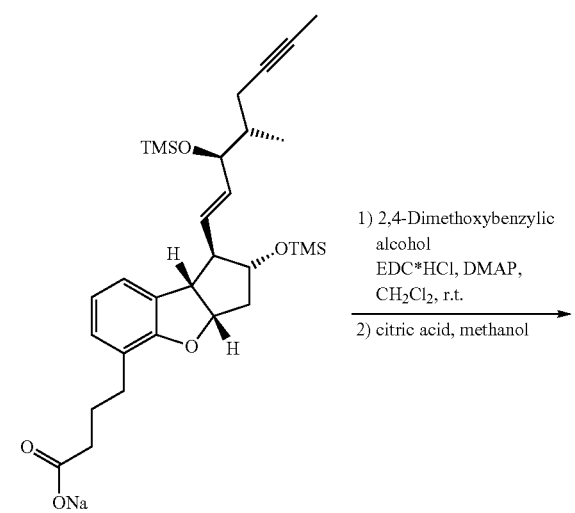

91
-continued

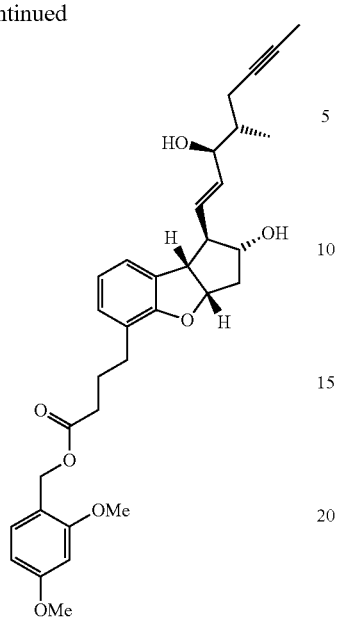

1b

EXAMPLE 2

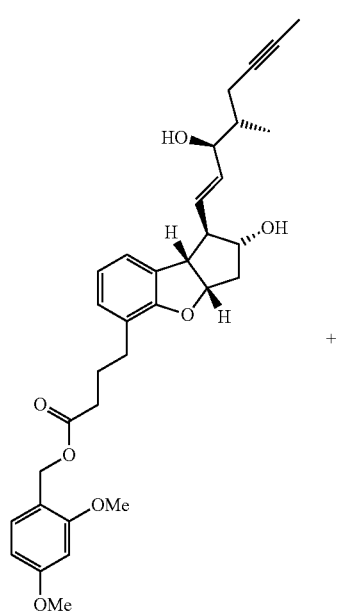

1b

92
-continued

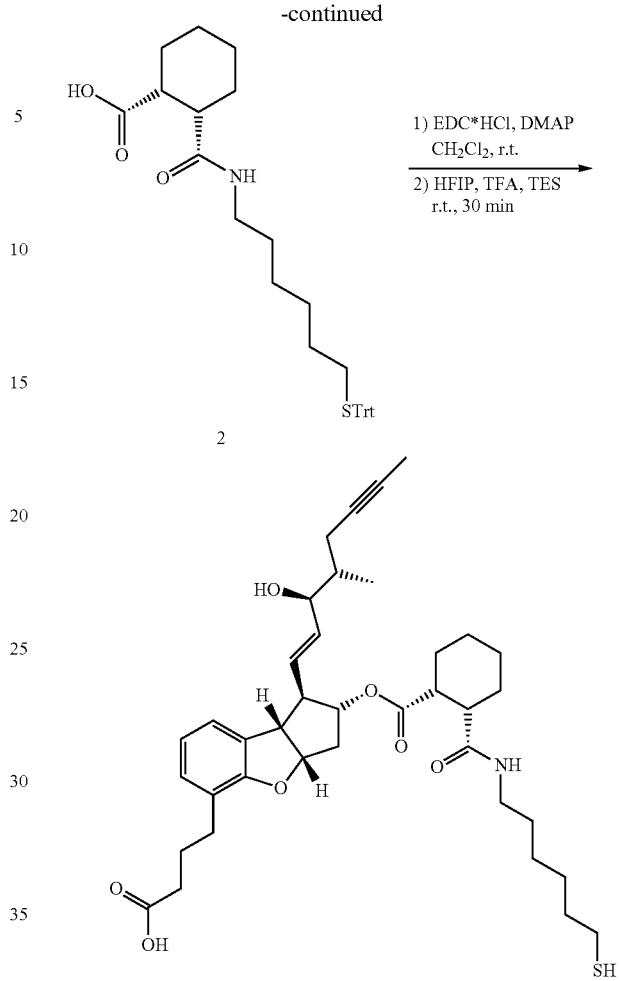

Synthesis of Beraprost Linker Thiol 3

Carboxylic acid (1R,2S) –2 (30.4 mg, 57.41 µmol, 1.5 eq.; see WO2013/024052A1), EDC.HCl (25.7 mg, 133.96 µmol, 3.5 eq) and DMAP (16.4 mg, 133.96 µmol, 3.5 eq) were added to dmob-beraprost 1b (21 mg, 38.27 µmol, 1.0 eq) and dissolved in $CH_2Cl_2$ (0.3 mL). The reaction mixture was stirred at r.t. for 20 h. After addition of ethyl acetate (10 mL), the solution was washed with 0.1 M HCl (3×5 mL). The aqueous phase was then extracted back with ethyl acetate (2×5 mL) and the combined organic phases were washed with brine (1×7 mL). The organic phase was dried over $Na_2SO_4$, filtered and concentrated in vacuo. The crude product was dissolved in HFIP (3 mL), then TFA (75 µL) and TES (75 µL) were sequentially added. During this procedure, the color of the reaction mixture changed from deep red to green to colorless. The reaction mixture was then stirred at r.t. for 40 min and reaction monitoring by UPLC revealed the formation of the product. Additional HFIP (7 mL) was added, and the reaction mixture was extracted with heptanes (6×20 mL). The HFIP phase was diluted with dichloromethane (20 mL) and washed with water (3×20 mL). The organic phase was dried over $Na_2SO_4$, filtered and concentrated to dryness. The crude material was dissolved in 2 mL of 7:3 $MeCN/H_2O$ and purified by preparative RP HPLC. The fractions containing 3 were pooled and lyophilized. The lyophilized HPLC solutions afforded thiol 3 as an amorphous colorless solid.

Yield: 2.7 mg (4.04 μmol, 11%).

EXAMPLE 3

Synthesis of Beraprost Linker Thiols 5 and 6

Carboxylic acid (1S,2R) –4 (23.2 mg, 43.74 μmol, 1.5 eq; isolated from enantiomer separation as detailed in see WO2013/024052A1), EDC.HCl (19.6 mg, 102.06 μmol, 3.5 eq) and DMAP (12.5 mg, 102.06 μmol, 3.5 eq) were added to dmob-beraprost 1b (16 mg, 29.16 μmol, 1.0 eq) and dissolved in $CH_2Cl_2$ (0.225 mL). The reaction mixture was stirred at r.t. for 15 h. After addition of ethyl acetate (10 mL), the solution was washed with 0.1 M HCl (3×5 mL). The aqueous phase was then extracted back with ethyl acetate (2×5 mL) and the combined organic phases were washed with brine (1×7 mL). The organic phase was dried over $Na_2SO_4$, filtered and concentrated in vacuo. The crude mixture was dissolved in HFIP (2.5 mL), then formic acid (125 μL) and TES (62.5 μL) were sequentially added. During this procedure, the color of the reaction mixture changed from deep red to green to colorless. The reaction mixture was then stirred at r.t. for 80 min and reaction monitoring by UPLC revealed the formation of the products. The HFIP solution was diluted with dichloromethane (15 mL) and washed with water (3×15 mL). The organic phase was dried over $Na_2SO_4$, filtered and concentrated to dryness. The crude material was dissolved in 2 mL of 7:3 $MeCN/H_2O$ and purified by preparative RP HPLC. The product containing fractions were pooled and lyophilized. The lyophilized HPLC solutions afforded thiols 5 and 6 as amorphous colorless solids.

Yield: 7.0 mg (10.48 μmol, 36%) for 5.

3.8 mg (5.69 μmol, 20%) for 6.

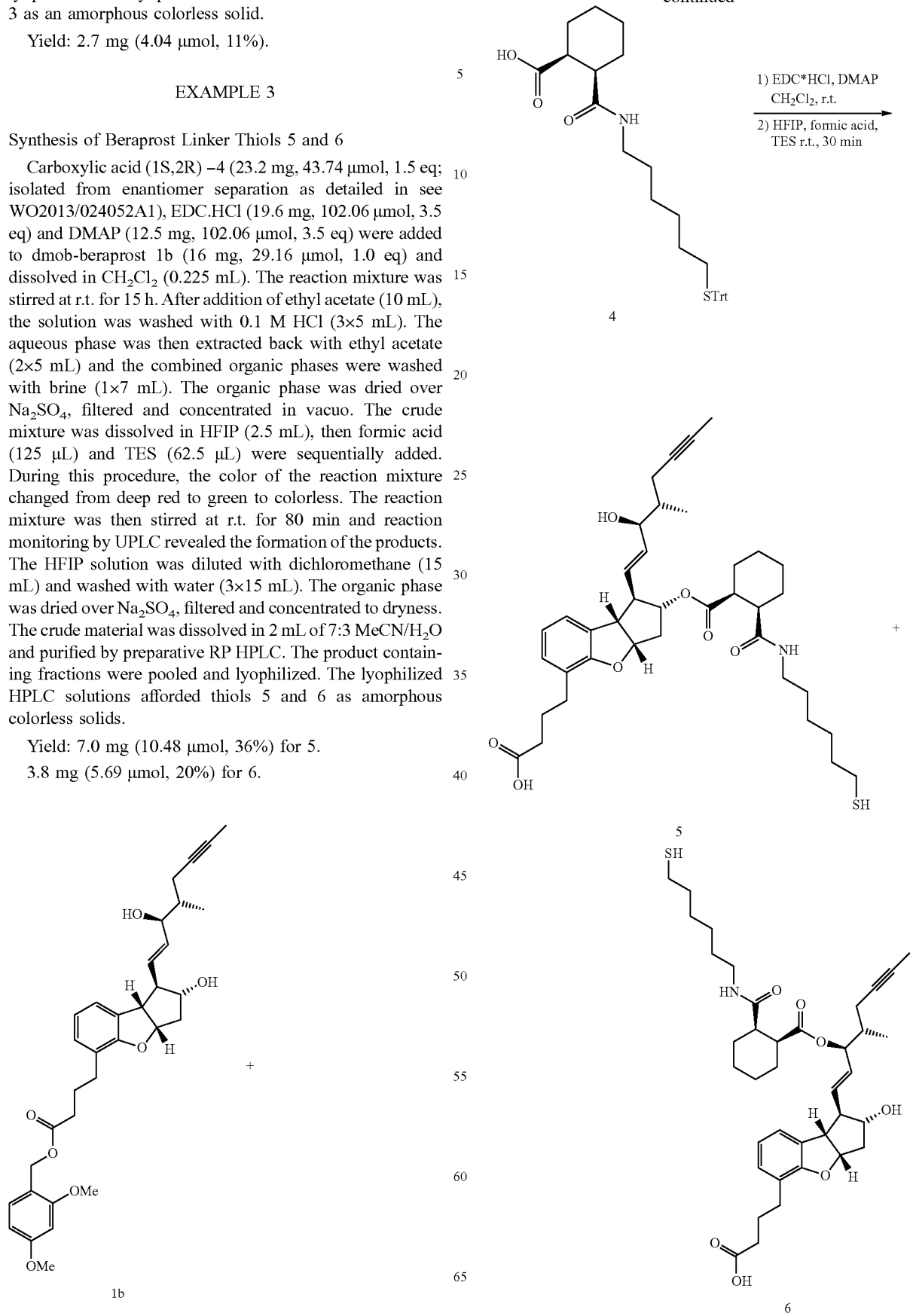

EXAMPLE 4

PEGylation Reaction of Beraprost Linker Thiol 3, 5 and 6 with 5 kDa PEG Maleimide 7

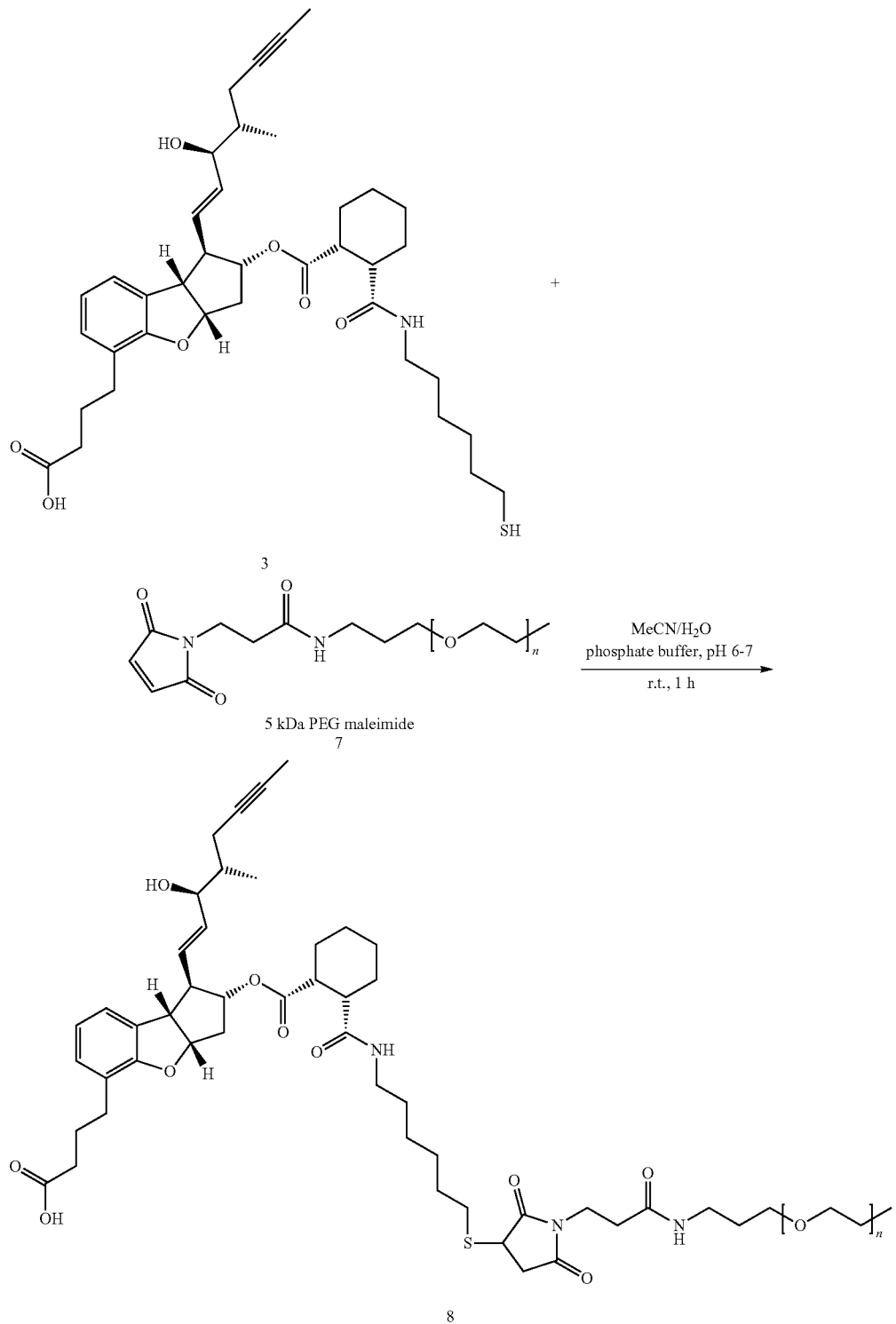

Preparation of Stock Solutions:

Thiol stock solutions from beraprost linker thiols 3, 5, 6 were prepared by dissolving the lyophilized compounds (2.3 mg, 3.44 μmol, 1.5 eq) in 9:1 MeCN/H$_2$O (0.7 mL). A PEG stock solution was prepared by dissolving the PEG 5 kDa maleimide 7 (12.3 mg, 2.29 μmol, 1.0 eq, Sunbright ME 050MA, NOF Corporation) in 1:1 MeCN/H$_2$O (1 mL).

Reaction Procedure:

For each linker thiol, thiol stock solution was added at r.t. to the PEG stock solution under stirring. The reaction was started by addition of phosphate buffer pH 7.5, resulting in a pH of ca. 6.5 as indicated by pH-paper. The clear solution was stirred 1 h at r.t. The reaction was quenched by addition of 1 mL H₂O containing 0.01% conc. HCl (v/v).

The diluted reaction mixture was purified by preparative RP HPLC. The pure product fractions were pooled and lyophilized to afford the corresponding PEG conjugate as amorphous colorless solids.

Yields: 8.4 mg (8), 11.5 mg (9), 11 mg (10).

EXAMPLE 5

Determination of the Release Kinetics of Beraprost from Conjugates 8, 9, 10 In Vitro at pH 7.40, 37° C.

TransCon PEG Beraprost conjugates 8, 9 and 10 (each ca. 3-4 mg) were dissolved in 1 mL hydrolysis buffer (60 mM phosphate, 3 mM EDTA, +0.01% Tween-20, pH 7.40) and filtered through a 0.22 μm sterile filter. 100 μL of the clear solution were diluted with 900 μL hydrolysis buffer and spiked with 1 μL of a pentafluorophenol (PFP) solution (20 mg/mL) in water (internal standard (IS) to make up for injection inaccuracies), the pH value of 7.40 was checked by means of a pH electrode and samples were incubated at 37° C. At given time points, the solution was mixed vigorously, centrifuged and samples (20 μL) were drawn and analyzed by UPLC.

Then, to determine the 100% value of the beraprost release, a total hydrolysis of an aliquot of the incubated solutions was performed. 50 μL of each incubated solution and 25 μL of 0.5 M NaOH were vigorously mixed for 30 min at r.t., then 25 μL of acetic acid were added and the resulting solution was briefly mixed. After analysis by UPLC, the beraprost/IS area ratio was calculated. After each time point analysis, the beraprost/IS ratio was calculated and the percentage of released beraprost was therefore calculated by comparison to the same ratio after total hydrolysis.

The percentage of released beraprost was then plotted versus the incubation time. Prism® software (version 5.02) was used to perform a non linear regression analysis and calculate the beraprost release at pH 7.40 and 37° C. as indicated in the following equation:

$$y = y_0 + (\text{plateau} - y_0) \cdot (1 - e^{-kx})$$

y=% released beraprost; y₀=origin of curve; plateau=100; k=rate constant for the release of beraprost from TransCon PEG Beraprost, x=incubation time.

The measured release half-lifes were 1.7 d (8), 3.1 d (9) and 5.3 d (10).

EXAMPLE 6

Determination of the Release Kinetics of Beraprost from Conjugates 8, 9, 10 in Rat Plasma
Incubation of TransCon PEG Beraprost 314d in Rat Plasma 1.2 mL rat plasma (Li heparin plasma from Wistar rats) were mixed with 150 μL incubation buffer (1000 mM HEPES, 3 mM EDTA, pH 7.4) and 150 μL of the synthesized TransCon PEG Beraprost conjugates (c=~0.1-0.25 mg/mL in hydrolysis buffer). A pH of 7.4 of the mixtures was confirmed by means of a pH electrode and monitored in separate reaction tubes over the time course of the incubation. The mixtures were incubated at 37° C. in an Eppendorf thermomixer.

At given time points 100 μL samples were withdrawn and immediately frozen in liquid nitrogen. Subsequently, samples were stored in a freezer at −80° C. until further processing. Three 100 μL aliquots were withdrawn of each preparation before incubation for the determination of the t₀ value the quantification of the total beraprost content after basic hydrolysis (duplicates).

Relative Quantification of Released Beraprost in Plasma Samples

All plasma and buffer samples (100 μL) were thawed on ice at 0-5° C. As internal standard, a stock solution of treprostinil (c=2.97 μg/mL in methanol/water, 20 μL) was added to each plasma sample. After vortexing and short centrifugation (1-2 sec) all samples were transferred into Ostro well plates and precipitated by rapid addition of three volume equivalents ice-cold acetonitrile containing 1 vol. % of formic acid. The samples were mixed by aspirating up and down three times with a manual pipette. For filtration the Ostro plate was subsequently placed on a positive pressure processor and the gas flow (Ar) was set at 18-20 psi for ~2 minutes. The filtrates were collected into 2 mL 96-deep-well plates. Subsequently, the wells were rinsed two times with 100 μL ice-cold acetonitrile containing 1 vol. % of formic acid (gas flow: 18-20 psi, 2×2 min). All eluates (650-900 μL) were transferred into eppendorf tubes and filled up with 300-550 μL of dilution solvent (10 mM ammonium formate, pH 4.0/acetonitrile 7:3 [v/v]) to a final volume of ~1200 μL. Finally, the sample solutions were mixed well by vortexing and 150 μL sample aliquots were prepared in UPLC vials for UPLC-MS/MS analysis.

The samples for total hydrolysis were additionally spiked with 0.5 M LiOH solution (50 μL) prior to precipitation. These vials were carefully closed and shaken horizontally at 400 rpm for 60 min at room temperature. 1 M HCl (25 μL) was added before they were precipitated in the same way as described above.

UPLC-MS/MS analysis was performed on an Agilent 6460 QQQ mass spectrometer. In all samples, the measured integral of the beraprost signal was calibrated against the internal standard. For all time points, the ratio of released beraprost to total beraprost (as determined by total hydrolysis) was calculated. From these data, release half-life was calculated to be 2.1±0.14 d for 8, 9.7±0.93 d for 9 and 5.4±0.78 d for 10.

| Abbreviation | Full expression and/or definition |
|---|---|
| Ac | Acetyl |
| AU | Absorption unit |
| BSA | N,O-Bis(trimethylsilyl)acetamide |
| d | Day |
| Da | Dalton |
| DMAP | 4-Dimethylaminopyridine |
| Dmob | 2,4-Dimethoxybenzyl |
| EDC | N-(3-Dimethylaminopropyl)-N'-ethyloxycarbodiimide |
| EDTA | Ethylenediaminetetraacetic acid |
| eq | Equivalent |
| ESI | Electron spray ionization |
| h | Hour |
| HFIP | 1,1,1,3,3,3-Hexafluoroisopropanol |
| HPLC | High performance liquid chromatography |
| HV | High vacuum |
| IS | Internal standard |
| M | Molar |
| MCA | Monochloroacetic acid |
| min | Minute |
| MRM | Multiple reaction monitoring |
| MS | Mass spectrometry |
| PAH | Pulmonary arterial hypertension |
| PEG | Polyethylene glycol |
| PFP | Pentafluorophenol |
| QC | Quality control |
| QQQ | Triple quadrupol |
| RP | Reverse phase |
| $R_t$ | Retention time |

| Abbreviation | Full expression and/or definition |
|---|---|
| rt | Room temperature |
| sc | Subcutaneous |
| sd | Standard deviation |
| t | Time |
| t/2 | Half life |
| TCA | Trichloroacetic acid |
| TCP | TransCon PEG |
| TES | Triethylsilane |
| TFA | Trifluoroacetic acid |
| THF | Tetrahydrofuran |
| TLC | Thin layer chromatography |
| TMS | Trimethylsilane |
| TransCon | Transiently conjugated |
| TransCon PEG Beraprost | Transiently conjugated beraprost covalently attached to a polyethylene glycol moiety |
| Trt | Trityl |
| UPLC | Ultra performance liquid chromatography |
| UV | Ultra violet |
| v | Volume |
| w | Weight |

The invention claimed is:

1. A carrier-linked prostanoid prodrug of formula (I) or a pharmaceutically acceptable salt thereof, where formula (I) is:

$$Z^1-(X^0-L^0-PG^0)_y \quad (I);$$

wherein:
  each $PG^0$ is independently beraprost, cicaprost, epoprostenol, iloprost, isocarbacyclin, or alprostadil, which is attached to $L^0$ through a hydroxyl or carboxyl group of $PG^0$;
  each $L^0$ is independently —(C=O)— or —O—(C=O)—, if $PG^0$ is attached to $L^0$ through a hydroxyl group; and —O—, if $PG^0$ is attached to $L^0$ through a carboxyl group;
  y is an integer ranging of from 1 to 64;
  each $X^0$ is independently $(X^{OB})_{m1}$—$(X^{OA})_{m2}$;
  m1 and m2 are both 1;
  each $X^{OA}$ is independently $T^0$;
  each $X^{OB}$ is independently a linear or branched $C_{1-50}$ alkyl, $C_{2-50}$ alkenyl, or $C_{2-50}$ alkynyl which is optionally one or more times interrupted by at least one group selected from the group consisting of:
    $R^1$;
    phenyl, naphthyl, azulenyl, indenyl, indanyl, $C_{3-7}$ cycloalkyl, 3-membered to 7-membered heterocyclyl, and 8-membered to 11-membered heterobicyclyl; and
    the following bivalent groups:

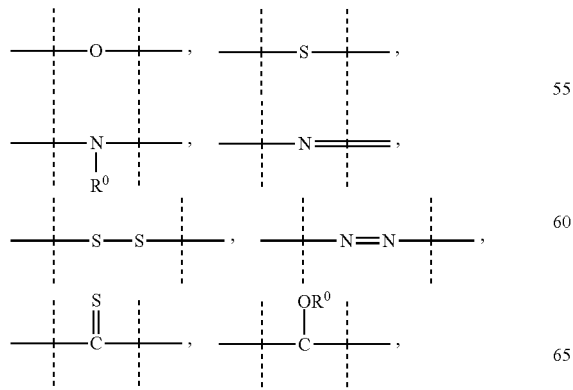

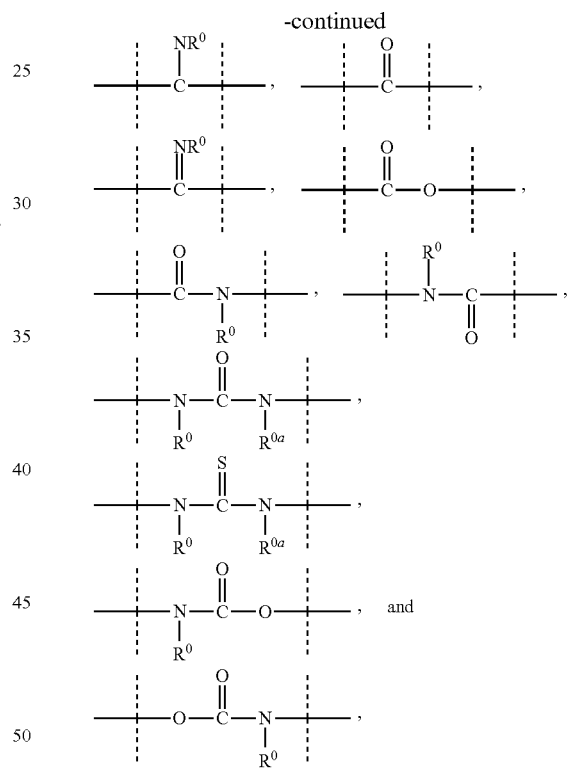

wherein:
  dashed lines indicate attachment points; and
  $R^0$ and $R^{0a}$ are independently of each other selected from the group consisting of H and $C_{1-6}$ alkyl;
wherein:
  $R^1$ is halogen, $C_{1-6}$alkyl, CN, $C(O)R^2$, $C(O)OR^2$, oxo (=O), $OR^2$, $C(O)R^2$, $C(O)N(R^2R^{2a})$, $S(O)_2N(R^2R^{2a})$, $S(O)N(R^2R^{2a})$, $S(O)_2R^2$, $S(O)R^2$, $N(R^2)S(O)_2N(R^2R^{2b})$, $SR^2$, $N(R^2R^{2a})$, $NO_2$, $OC(O)R^2$, $N(R^2)C(O)R^2$, $N(R^2)SO_2R^{2a}$, $N(R^2)S(O)R^{2a}$, $N(R^2)C(O)N(R^{2a}R^{2b})$, $N(R^2)C(O)OR^{2a}$, $OC(O)N(R^2R^{2a})$, or $T^0$;
  $R^2$, $R^{2a}$, and $R^{2b}$ are independently H, $T^0$, $C_{1-6}$ alkyl, $C_{2-6}$ alkenyl, or $C_{2-6}$ alkynyl, wherein said $C_{1-6}$ alkyl, $C_{2-6}$ alkenyl, and $C_{2-6}$ alkynyl are optionally substituted with one or more $R^3$, which are the same or different;

$R^3$ is halogen, CN, $C(O)R^4$, $C(O)OR^4$, $OR^4$, $C(O)R^4$, $C(O)N(R^4R^{4a})$, $S(O)_2N(R^4R^{4a})$, $S(O)N(R^4R^{4a})$, $S(O)_2R^4$, $S(O)R^4$, $N(R^4)S(O)N(R^{4a}R^{4b})$, $SR^4$, $N(R^4R^{4a})$, $NO_2$, $OC(O)R^4$, $N(R^4)C(O)R^{4a}$, $N(R^4)SO_2R^{4a}$, $N(R^4)S(O)R^{4a}$, $N(R^4)C(O)N(R^{4a}R^{4b})$, $N(R^4)C(O)OR^{4a}$, or $OC(O)N(R^4R^{4a})$;

$R^4$, $R^{4a}$, and $R^{4b}$ are independently H, $C_{1-6}$ alkyl, $C_{2-6}$ alkenyl, or $C_{2-6}$ alkynyl; wherein said $C_{1-6}$ alkyl, $C_{2-6}$ alkenyl, and $C_{2-6}$ alkynyl are optionally substituted with one or more halogen, which are the same or different;

$T^0$ is phenyl, naphthyl, azulenyl, indenyl, indanyl, $C_{3-10}$ cycloalkyl, 3-membered to 7-membered heterocyclyl, or 8-membered to 11-membered heterobicyclyl, wherein $T^0$ is optionally substituted with one or more $R^5$, which are the same or different;

$R^5$ is halogen, CN, $COOR^6$, $OR^6$, $C(O)R^6$, $C(O)N(R^6R^{6a})$, $S(O)_2N(R^6R^{6a})$, $S(O)N(R^6R^{6a})$, $S(O)_2R^6$, $S(O)R^6$, $N(R^6)S(O)_2N(R^6R^{6b})$, $SR^6$, $N(R^6R^{6a})$, $NO_2$, $OC(O)R^6$, $N(R^6)C(O)R^6$, $N(R^6)S(O)_2R^{6a}$, $N(R^6)S(O)R^6$, $N(R^6)C(O)OR^{6a}$, $N(R^6)C(O)N(R^6R^{6b})$, $OC(O)N(R^6R^{6a})$, oxo (=O) where the ring is at least partially saturated, $C_{1-6}$ alkyl, $C_{2-6}$ alkenyl, or $C_{2-6}$ alkynyl, wherein said $C_{1-6}$ alkyl, $C_{2-6}$ alkenyl, and $C_{2-6}$ alkynyl are optionally substituted with one or more $R^7$, which are the same or different;

$R^6$, $R^{6a}$, and $R^{6b}$ are independently H, $C_{1-4}$ alkyl, $C_{2-6}$ alkenyl, and $C_{2-6}$ alkynyl, wherein said $C_{1-6}$ alkyl, $C_{2-6}$ alkenyl, and $C_{2-6}$ alkynyl are optionally substituted with one or more $R^8$, which are the same or different;

$R^7$ and $R^8$ are independently halogen, CN, $C(O)R^9$, $C(O)OR^9$, $OR^9$, $C(O)R^9$, $C(O)N(R^9R^{9a})$, $S(O)_2N(R^9R^{9a})$, $S(O)N(R^{9a})$, $S(O)_2R^9$, $S(O)R^9$, $N(R^9)S(O)_2N(R^9R^{9b})$, $SR^9$, $N(R^9R^{9a})$, $NO_2$, $OC(O)R^9$, $N(R^9)C(O)R^9$, $N(R^9)SO_2R^9$, $N(R^9)S(O)R^{9a}$, $N(R^9)C(O)N(R^{9a}R^{9b})$, $N(R^9)C(O)OR^{9a}$, or $OC(O)N(R^9R^{9a})$;

$R^9$, $R^{9a}$, and $R^{9b}$ are independently H, $C_{1-6}$ alkyl, $C_{2-6}$ alkenyl, and $C_{2-6}$ alkynyl, wherein said $C_{1-6}$ alkyl, $C_{2-6}$ alkenyl, and $C_{2-6}$ alkynyl are optionally substituted with one or more halogen, which are the same or different;

$Z^1$ is a carrier comprising:
  a covalently bound polymer; or
  a covalently bound $C_{10-24}$ fatty acid;
wherein the carrier is covalently attached to a moiety $X^0$.

2. The carrier-linked prostanoid prodrug of claim 1; where $Z^1$ is a carrier comprising a covalently bound polymer.

3. The carrier-linked prostanoid prodrug of claim 1; wherein $Z^1$ is a carrier comprising a covalently bound $C_{10-24}$ fatty acid.

4. The carrier-linked prostanoid prodrug of claim 1; wherein each moiety $-L^0-PG^0$ is independently a formula selected from the group consisting of (i-a), (i-b), (i-c), (i-d), (i-e), (ii-a), (ii-b), (ii-c), (ii-d), (ii-e), (iii-a), (iii-b), (iii-c), (iii-d), (iii-e), (iv-a), (iv-b), (iv-c), (iv-d), (iv-e), (v-a), (v-b), (v-c), (v-d), (v-e), (vi-a), (vi-b), (vi-c), (vi-d), and (vi-e):

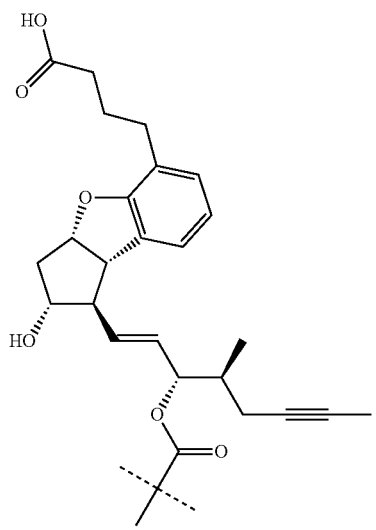

(i-a)

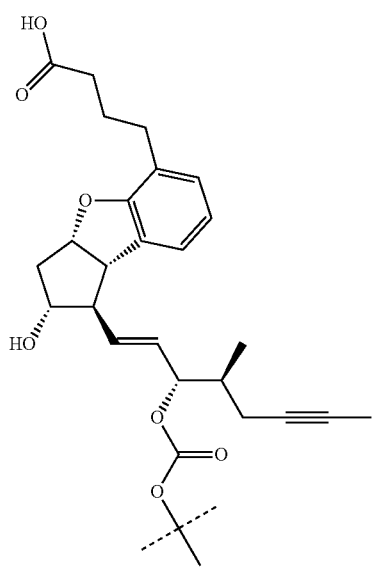

(i-b)

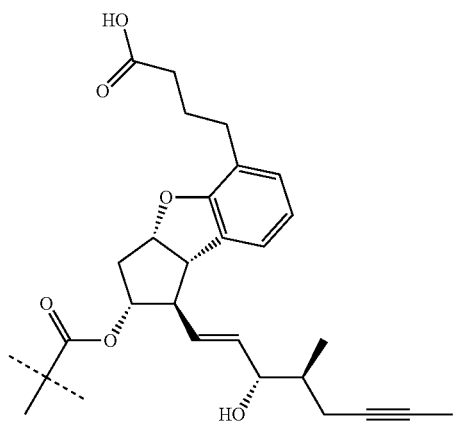

(i-c)

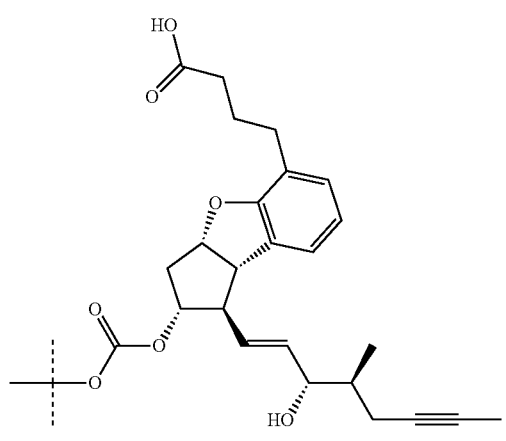
(i-d)
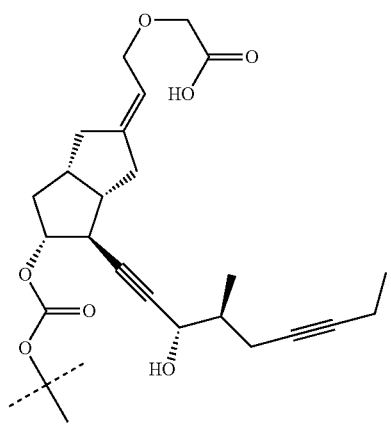
(ii-b)
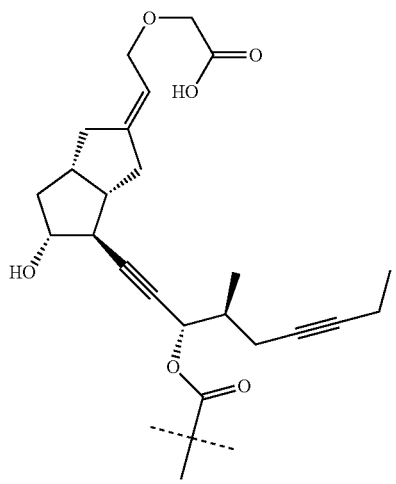
(i-e)
(ii-c)
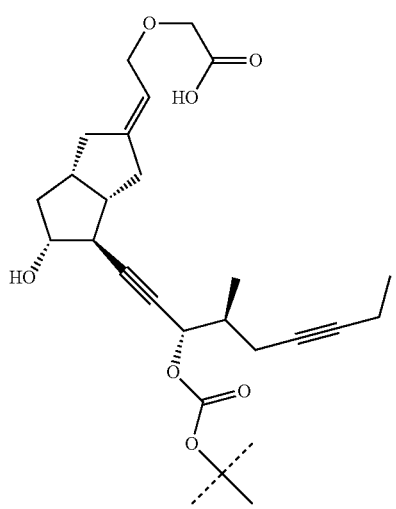
(ii-a)
(ii-d)

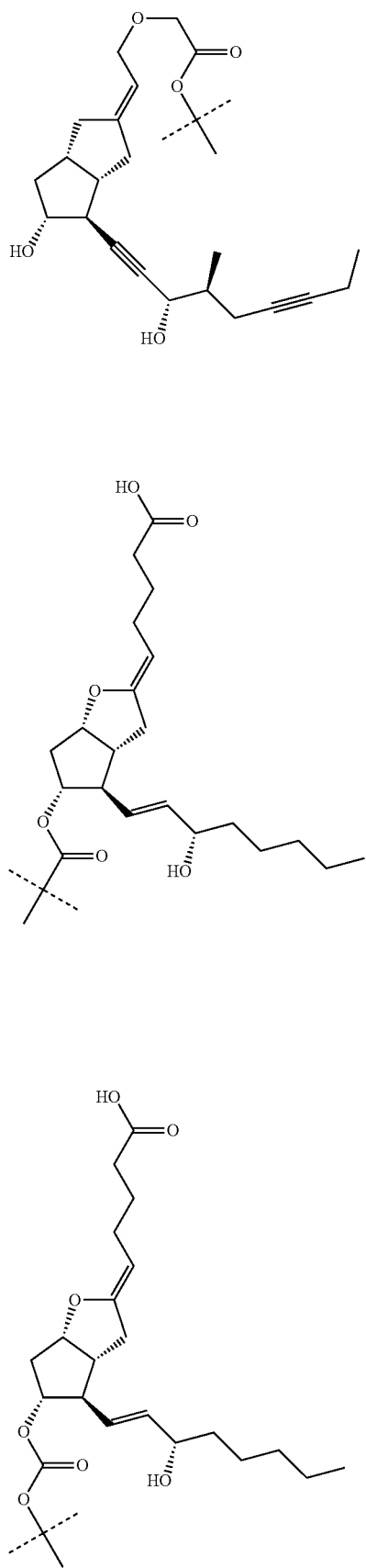
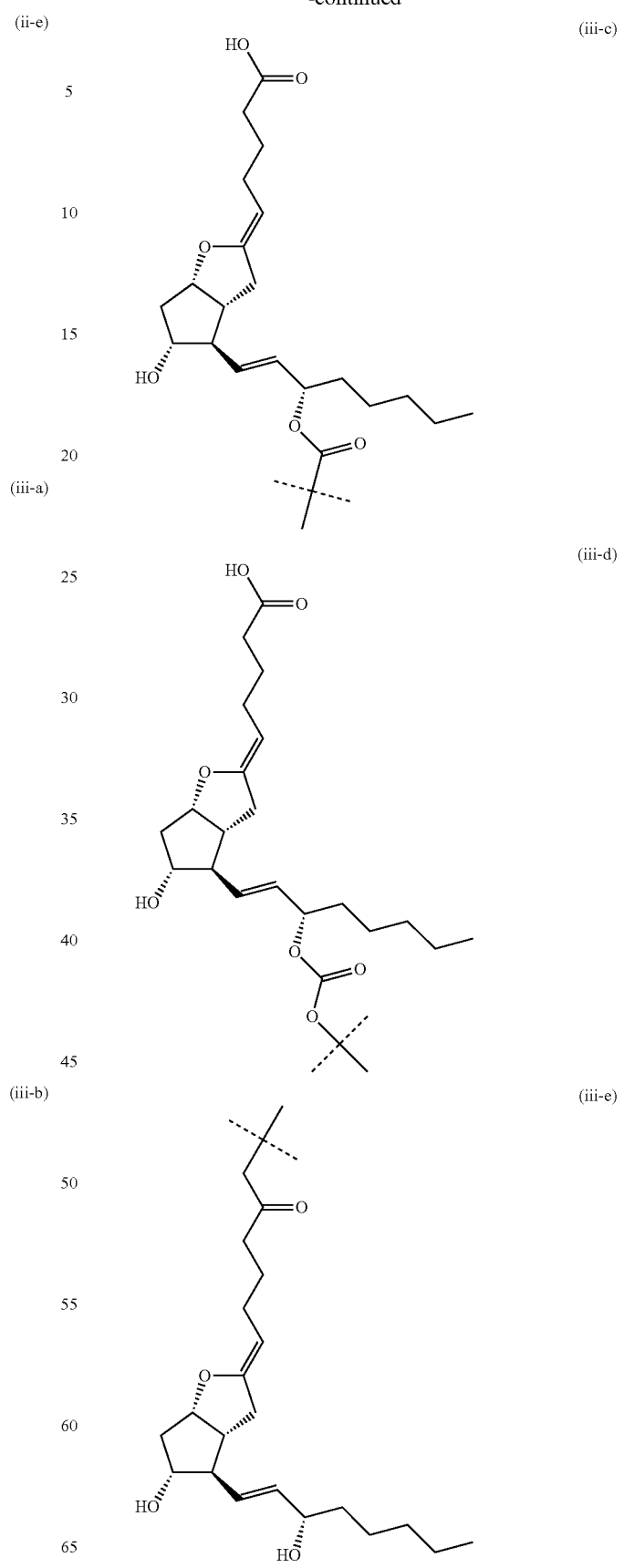

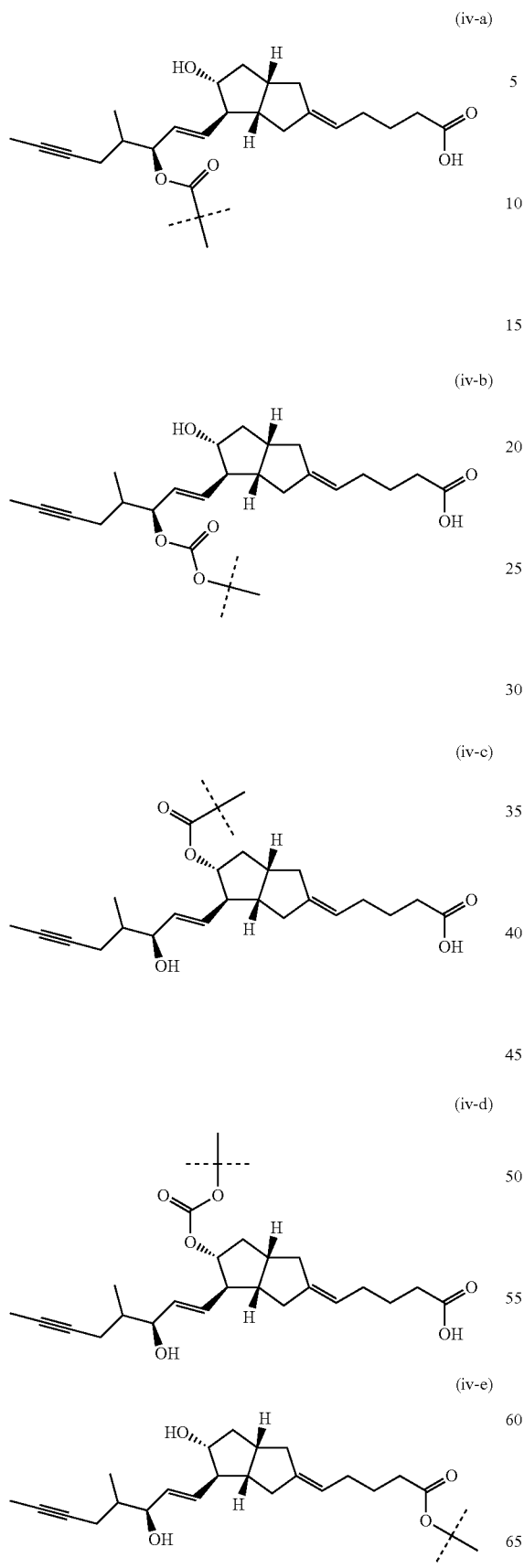
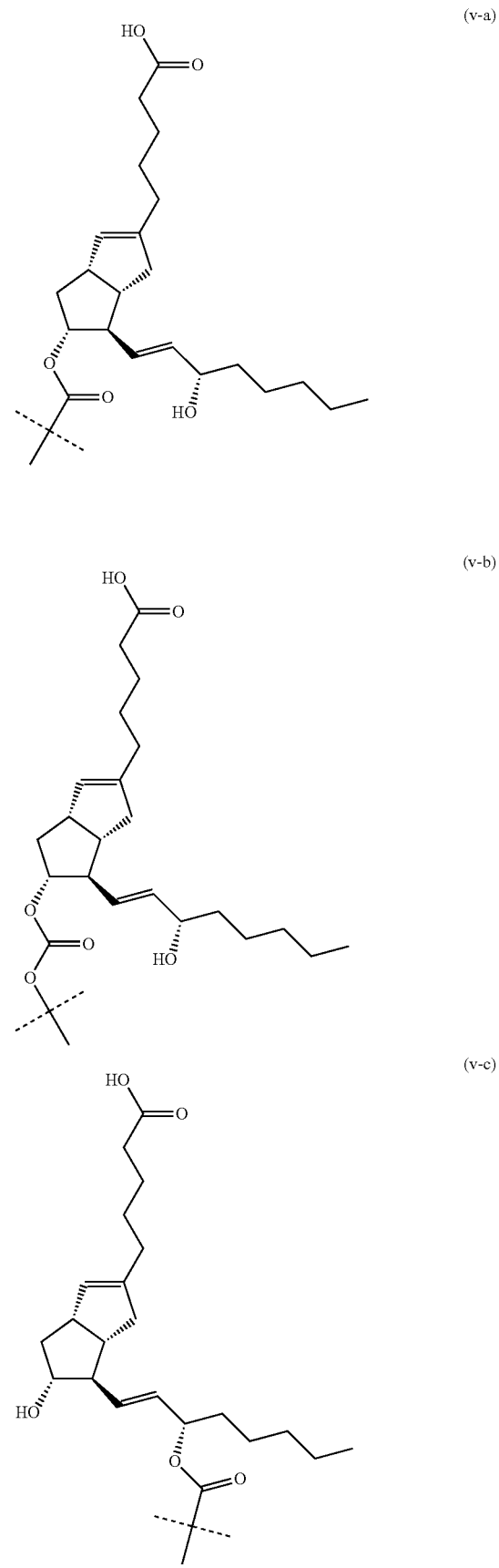

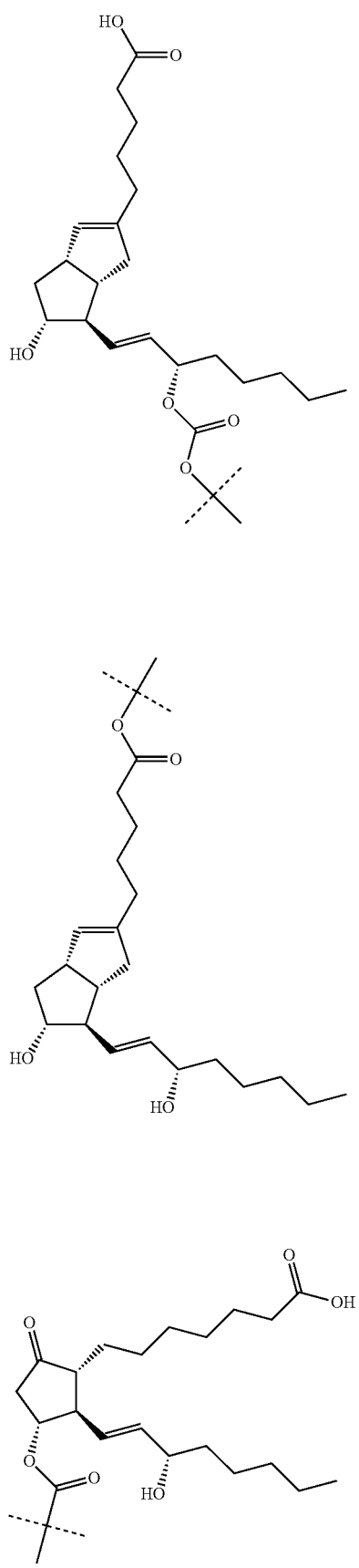
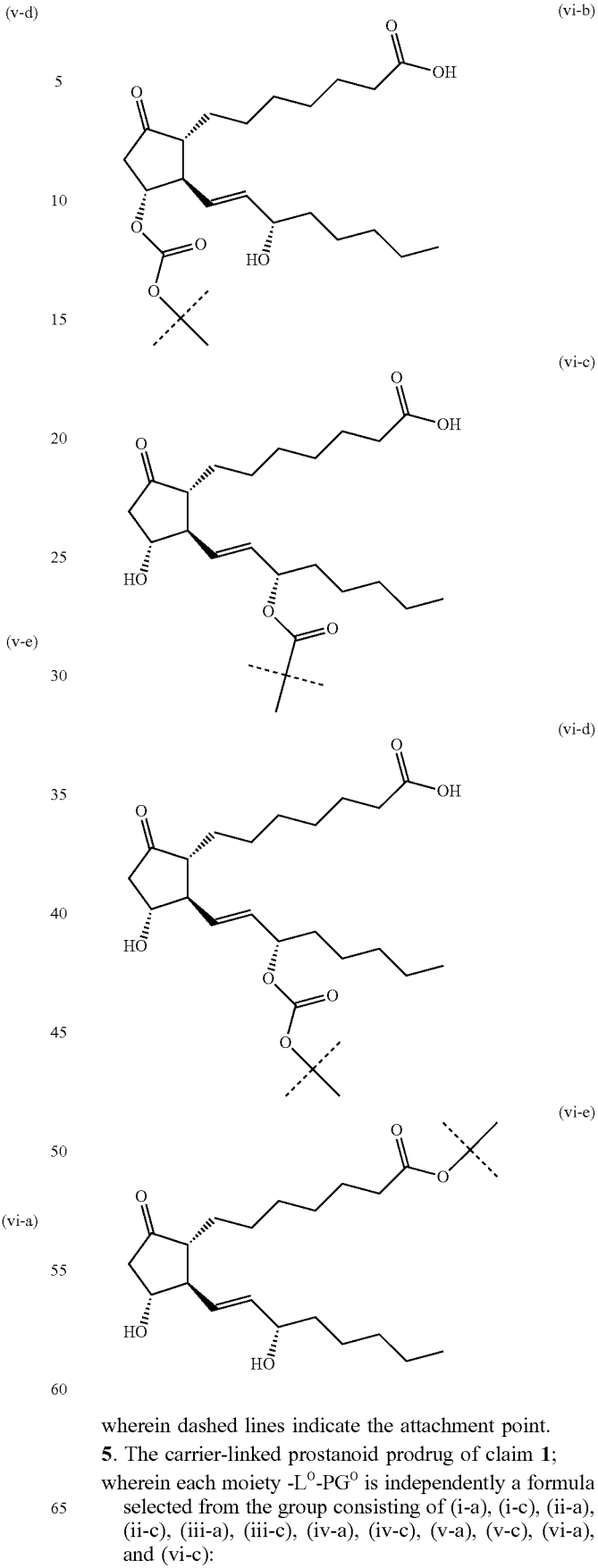
wherein dashed lines indicate the attachment point.
5. The carrier-linked prostanoid prodrug of claim 1; wherein each moiety -L⁰-PG⁰ is independently a formula selected from the group consisting of (i-a), (i-c), (ii-a), (ii-c), (iii-a), (iii-c), (iv-a), (iv-c), (v-a), (v-c), (vi-a), and (vi-c):

117
(i-a)
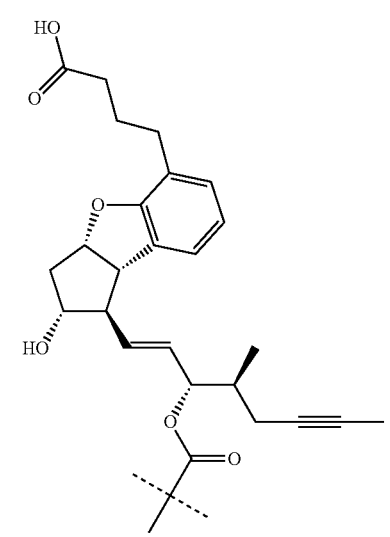
(i-c)
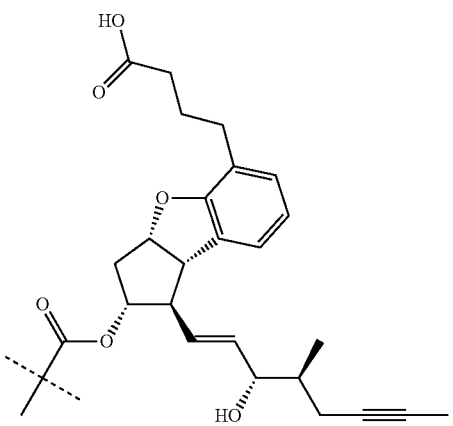
(ii-a)
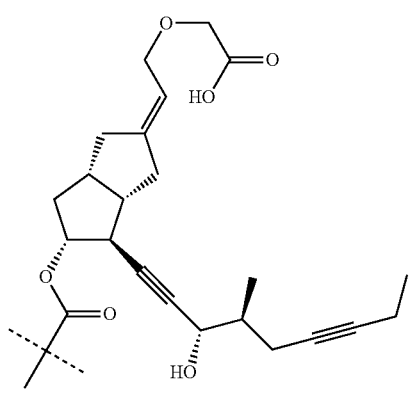
118
-continued
(ii-c)
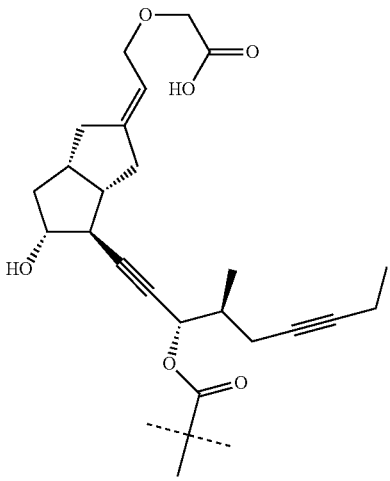
(iii-a)
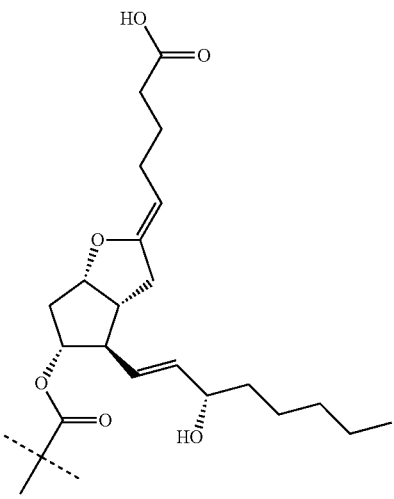
(iii-c)
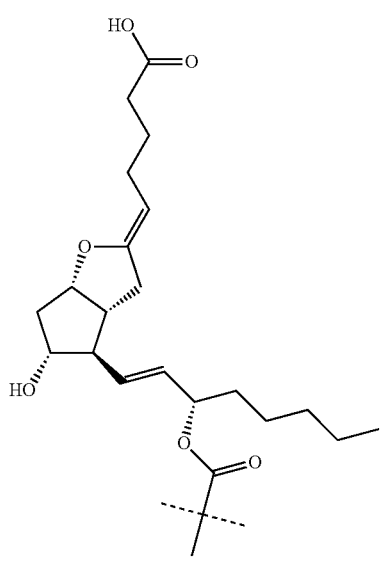

(iv-a)
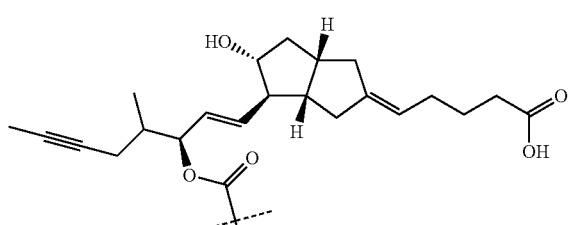
(iv-c)
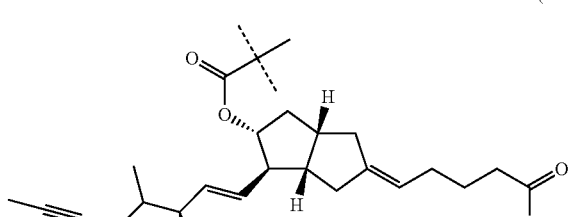
(v-a)
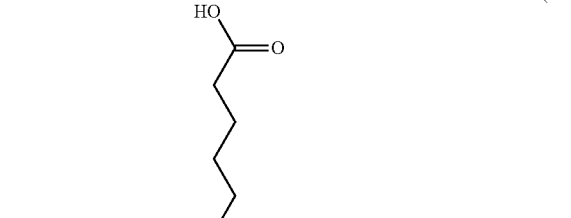
(v-c)
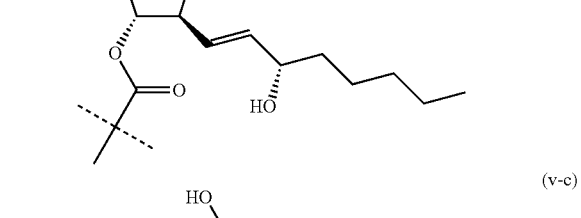
(vi-a)
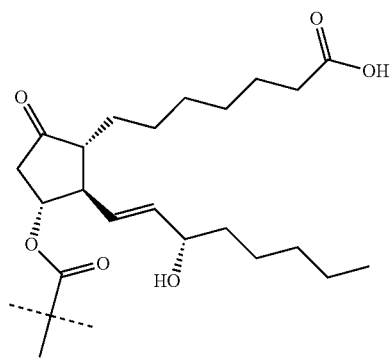
(vi-c)
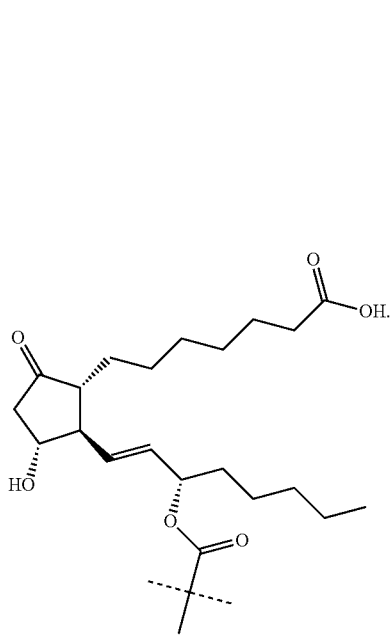
6. The carrier-linked prostanoid prodrug of claim 1; wherein each moiety -L⁰-PG⁰ is of formula (i-a) or (i-c):
(i-a)
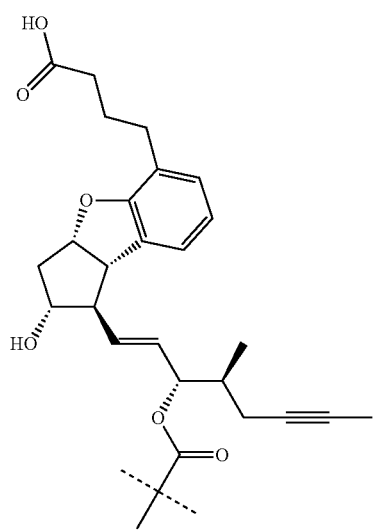

-continued (i-c)

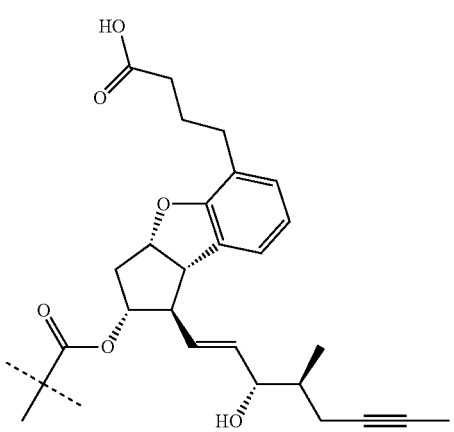

7. The carrier-linked prostanoid prodrug of claim 1; wherein y is 2, 4, 6, 8, 10, 12, 14, 16, 20, 24, 32, or 48.

8. The carrier-linked prostanoid prodrug of claim 1;
wherein $X^{0A}$ is phenyl, $C_{3-10}$ cycloalkyl, 3-membered to 7-membered heterocyclyl, or 8-membered to 11-membered heterobicyclyl, which is optionally substituted with one or more $R^5$; and
wherein $R^5$ is selected from the group consisting of halogen, CN, COOH, OH, C(O)H, C(O)NH$_2$, S(O)$_2$NH$_2$, S(O)NH$_2$, S(O)$_2$H, S(O)H, NHS(O)$_2$NH$_2$, SH, NH$_2$, NO$_2$, OC(O)H, NHC(O)H, NHS(O)$_2$H, NHS(O)H, NHC(O)OH, NHC(O)NH$_2$, OC(O)NH$_2$, oxo (=O) where the ring is at least partially saturated, $C_{1-6}$ alkyl, $C_{2-6}$ alkenyl, and $C_{2-6}$ alkynyl.

9. The carrier-linked prostanoid prodrug of claim 1;
wherein:
$X^{0A}$ is of structure (Iab):

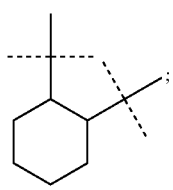

(Iab)

wherein dashed lines indicate attachment points.

10. The carrier-linked prostanoid prodrug of claim 1;
wherein $X^{0B}$ is a linear or branched $C_{1-50}$ alkyl, $C_{2-50}$ alkenyl, or $C_{2-50}$ alkynyl which is optionally one or more times interrupted by at least one group selected from the group consisting of:
$R^1$; and
the following bivalent groups:

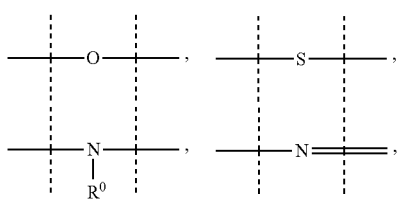

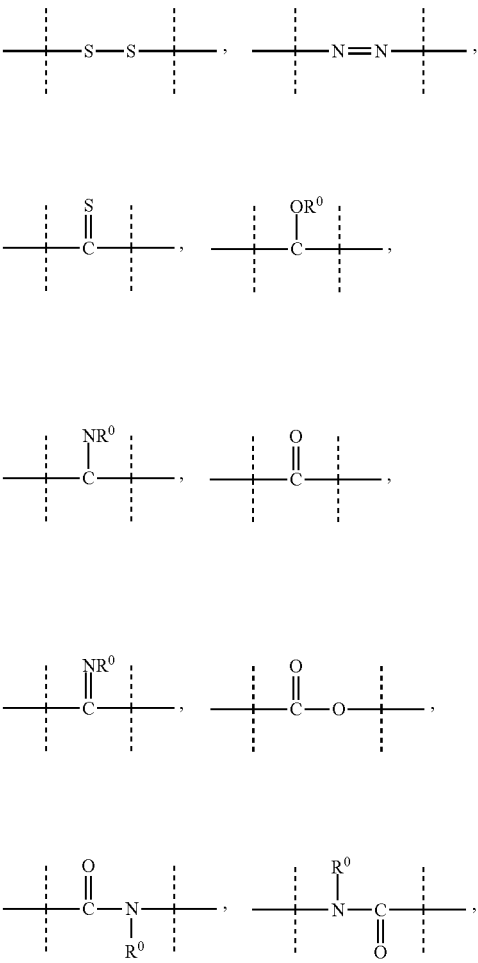

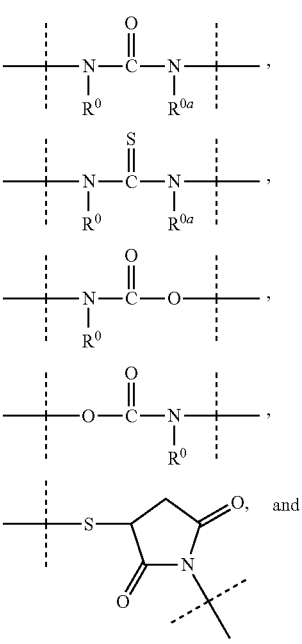

-continued

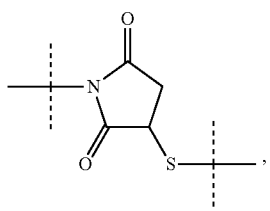

wherein:

dashed lines indicate attachment points;

R⁰ and $R^{0a}$ are independently of each other selected from H and $C_{1-6}$ alkyl; and $R^1$ is halogen, $C_1$ alkyl, CN, C(O)H, C(O)OH, OH, C(O)H, $C(O)NH_2$, $S(O)_2NH_2$, $S(O)NH_2$, $S(O)_2H$, S(O)H, $NHS(O)_2NH_2$, SH, $NH_2$, $NO_2$, OC(O)H, NHC(O)H, $NHSO_2H$, NHS(O)H, $NHC(O)NH_2$, NHC(O)OH, $OC(O)NH_2$, phenyl, naphthyl, azulenyl, indenyl, indanyl, $C_{3-7}$ cycloalkyl, 3-membered to 7-membered heterocyclyl, or 8-membered to 11-membered heterobicyclyl.

11. The carrier-linked prostanoid prodrug of claim 1; wherein $X^{0B}$ is a linear or branched $C_{1-50}$ alkyl, $C_{2-50}$ alkenyl, or $C_{2-50}$ alkynyl which is optionally one or more times interrupted by one or more of the following bivalent groups

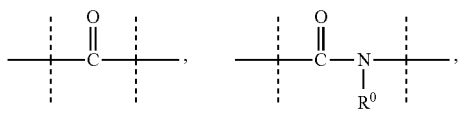

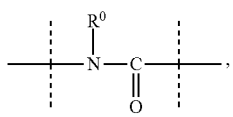

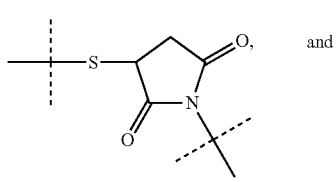 and

-continued

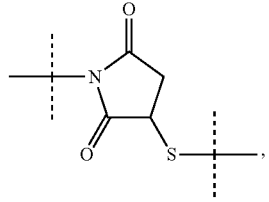

wherein dashed lines indicate the attachment point.

12. The carrier-linked prostanoid prodrug of claim 1; wherein $X^{0B}$ is of formula (Ibd):

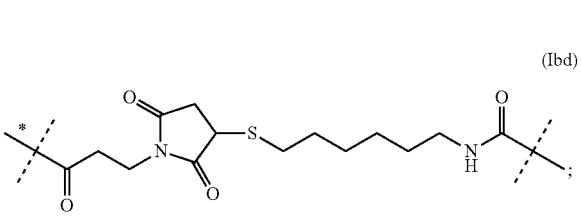

(Ibd)

wherein:

the dashed line marked with the asterisk indicates attachment to $Z^1$; and the unmarked dashed line indicates attachment to $X^{0A}$.

13. The carrier-linked prostanoid prodrug of claim 1; wherein the carrier $Z^1$ is covalently attached to a moiety $X^0$ via an amide linkage.

14. The carrier-linked prostanoid prodrug of claim 1; wherein the carrier $Z^1$ has the structure of formula (A-iv):

$$B-(A)_q \qquad (A-iv);$$

wherein:

B is branching core comprising at least one moiety selected from the group consisting of:

a polyalcohol comprising at least 2 hydroxyl groups; and a polyamine comprising at least 2 amine groups; wherein the polyalcohol or polyamine is in bound form;

each A is independently a PEG-based polymeric chain comprising at least 20% (w/w) ethylene glycol units; and q is an integer of from 3 to 64.

15. The carrier-linked prostanoid prodrug of claim 14; wherein q and y have the same value.

16. The carrier-linked prostanoid prodrug of claim 1; wherein the carrier $Z^1$ has the structure of formula (A-iva):

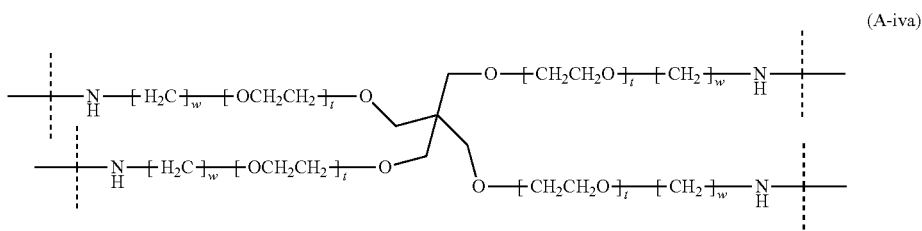

(A-iva)

wherein
dashed lines indicate attachment points to $X^0$;
t is an integer ranging from 80 to 160; and
w is an integer ranging from 2 to 6.

17. The carrier-linked prostanoid prodrug of claim 1;
wherein the carrier-linked prostanoid prodrug has the structure of formula (III):

(III)

wherein $Z^1$ has the structure:

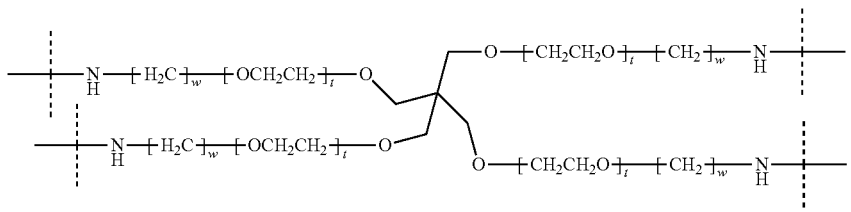

wherein:
dashed lines indicate attachment points to $P^1$;
t is an integer ranging from 80 to 160; and
w is 2 or 3; and wherein each moiety $P^1$ has the structure:

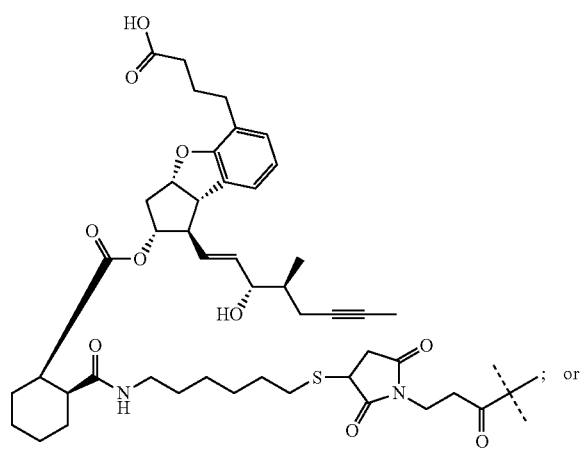

; or

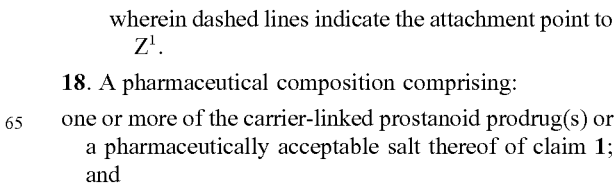

wherein dashed lines indicate the attachment point to $Z^1$.

18. A pharmaceutical composition comprising:
one or more of the carrier-linked prostanoid prodrug(s) or a pharmaceutically acceptable salt thereof of claim 1; and optionally one or more pharmaceutically acceptable excipients.

19. A method of treating pulmonary hypertension, comprising:
administering to a subject in need thereof an effective amount of the carrier-linked prostanoid prodrug or pharmaceutically acceptable salt thereof of claim 1.

20. The method of claim 19;
wherein $PG^0$ is a beraprost moiety.

21. The carrier-linked prostanoid prodrug of claim 9; wherein:
$X^{0.4}$ is of structure (Iac):

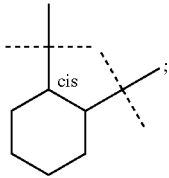

(Iac)

wherein dashed lines indicate attachment points.

* * * * *

UNITED STATES PATENT AND TRADEMARK OFFICE
CERTIFICATE OF CORRECTION

PATENT NO. : 9,913,912 B2
APPLICATION NO. : 14/650175
DATED : March 13, 2018
INVENTOR(S) : Harald Rau et al.

It is certified that error appears in the above-identified patent and that said Letters Patent is hereby corrected as shown below:

In the Specification

Column 20, Lines 5 to 20 and in the Claims, Claim 4, Column 112, Lines 45 to 65 – structure (iii-e):at one end a ketone is drawn instead of an ester – the O was replaced by C. Please replace with the structure below:

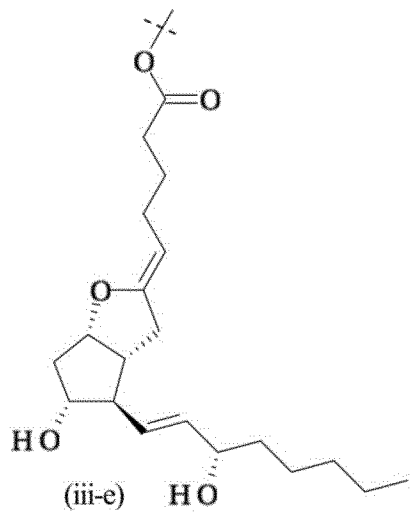

Signed and Sealed this
Fourth Day of June, 2019

Andrei Iancu
*Director of the United States Patent and Trademark Office*

Column 38 – in structures (A-i) and (A-ii) the first square bracket with n3 includes 3 C atoms, instead of 2, as for polyethylene. Please replace with the structure below:
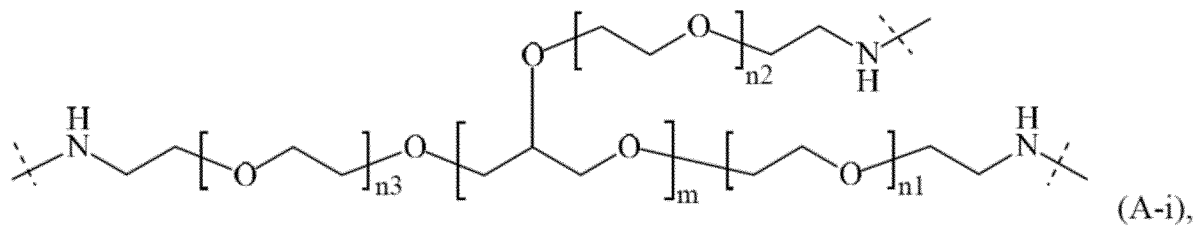 (A-i),
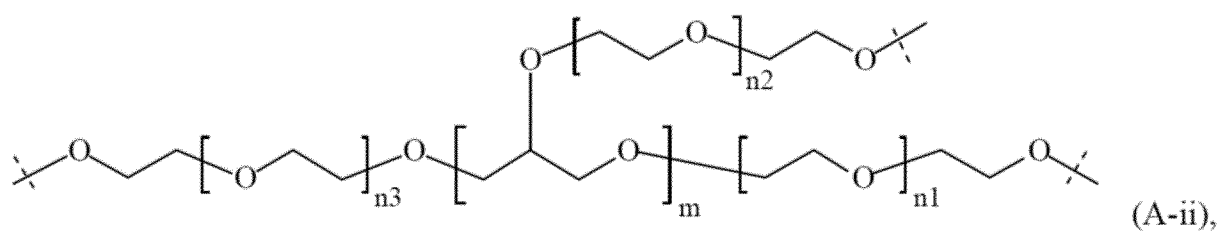 (A-ii), Column 50 – structure (b-iii) is split into two separate parts, the N to C bond should be reunited. Please replace with structure below:
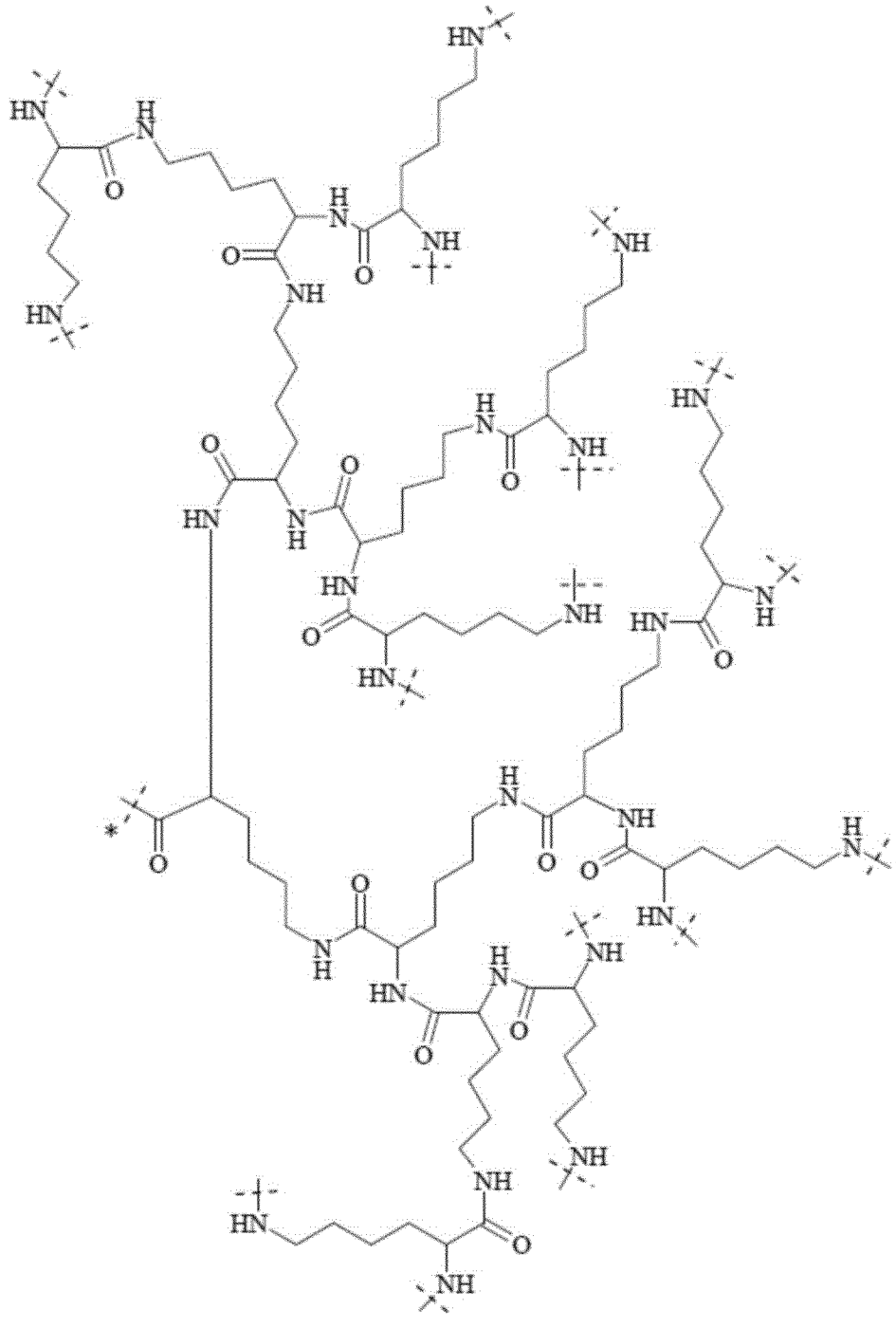
(b-iii).
Column 58, Line 35, please replace with formula below:
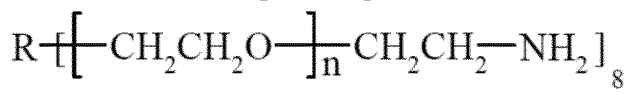

CERTIFICATE OF CORRECTION (continued)
U.S. Pat. No. 9,913,912 B2

Column 58, Line 49, please replace with formula below:

Columns 58, Line 65, please replace with the formula below:

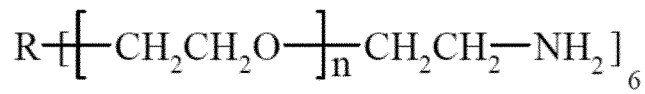

Column 59, Line 16, please replace with the formula below:

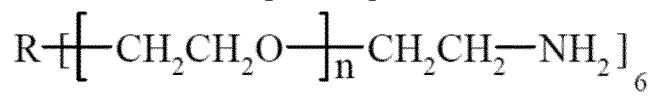

Column 59, Line 51, please replace with the formula below:

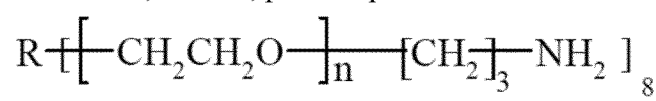

Column 59, Line 66, please replace with the formula below:

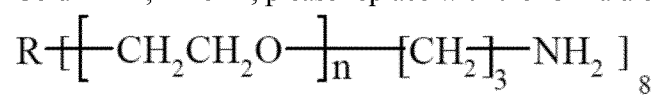

Column 60, Line 16, please replace with the formula below:

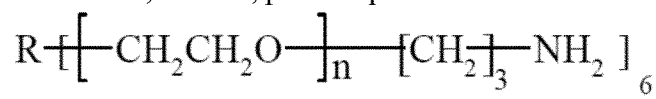

Column 60, Line 34, please replace with the formula below:

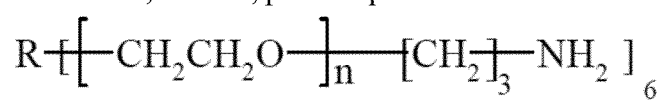

Column 61, Line 4, please replace with the formula below:

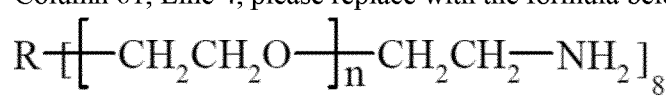

Column 61, Line 19, please replace with the formula below:

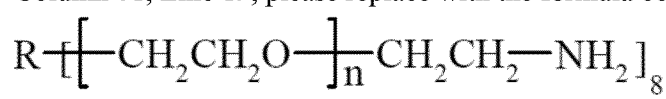

Column 61, Line 36, please replace with the formula below:

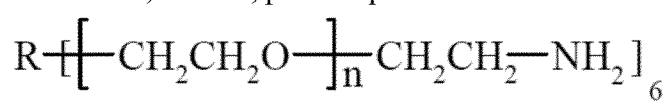

Column 61, Line 52, please replace with the formula below:

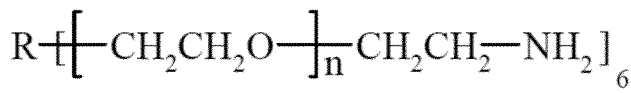

Column 62 Line 15, please replace with the formula below:

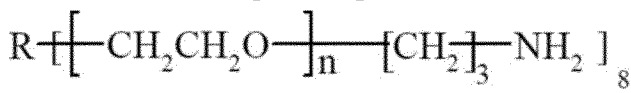

Column 62, Line 28, some bonds within the structures are interrupted and should be one line/bond; please replace with structure below:

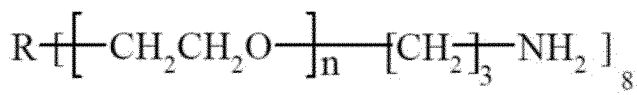

Column 62, Line 44, please replace with structure below:

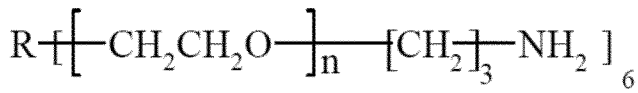

Column 62, Line 58, please replace with structure below:

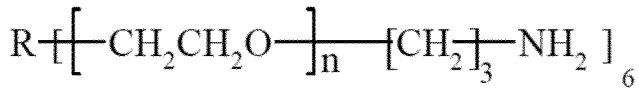

In the Claims

Claim 1, Column 106, Line 63:
--N($R^2$)C(O)$R^2$--
Should be:
--N($R^2$)C(O)$R^{2a}$,--

Claim 1, Column 107, Line 34:
--$C_{1-4}$ alkyl--
Should be:
--$C_{1-6}$ alkyl;--

Claim 10, Column 123, Line 19:
--$C_1$--
Should be:
--$C_{1-6}$ alkyl.--

SEQUENCE LISTING

```
<160> NUMBER OF SEQ ID NOS: 15

<210> SEQ ID NO 1
<211> LENGTH: 20
<212> TYPE: PRT
<213> ORGANISM: Artificial Sequence
<220> FEATURE:
<223> OTHER INFORMATION: polymer cassette

<400> SEQUENCE: 1

Ala Ala Ala Ala Ser Ser Ala Ser Ser Ala Ser Ser Ser Ser Ala
1               5                   10                  15

Ala Ala Ser Ala
            20

<210> SEQ ID NO 2
<211> LENGTH: 20
<212> TYPE: PRT
<213> ORGANISM: Artificial Sequence
<220> FEATURE:
<223> OTHER INFORMATION: polymer cassette

<400> SEQUENCE: 2

Ala Ala Ser Ala Ala Ala Ser Ser Ala Ala Ala Ser Ala Ala Ala
1               5                   10                  15

Ser Ala Ser Ser
            20

<210> SEQ ID NO 3
<211> LENGTH: 20
<212> TYPE: PRT
<213> ORGANISM: Artificial Sequence
<220> FEATURE:
<223> OTHER INFORMATION: polymer cassette

<400> SEQUENCE: 3

Ala Ser Ala Ser Ala Ser Ala Ser Ala Ser Ala Ser Ser Ala Ala Ser
1               5                   10                  15

Ala Ala Ser Ala
            20

<210> SEQ ID NO 4
<211> LENGTH: 20
<212> TYPE: PRT
<213> ORGANISM: Artificial Sequence
<220> FEATURE:
<223> OTHER INFORMATION: polymer cassette

<400> SEQUENCE: 4

Ser Ala Ala Ser Ser Ser Ala Ser Ser Ser Ser Ala Ala Ser Ser Ala
```

-continued

```
                1               5                  10                 15
Ser Ala Ala Ala
            20

<210> SEQ ID NO 5
<211> LENGTH: 20
<212> TYPE: PRT
<213> ORGANISM: Artificial Sequence
<220> FEATURE:
<223> OTHER INFORMATION: polymer cassette

<400> SEQUENCE: 5

Ser Ser Ser Ser Ala Ala Ser Ala Ala Ser Ala Ala Ala Ala Ser
1               5                  10                 15

Ser Ser Ala Ser
            20

<210> SEQ ID NO 6
<211> LENGTH: 20
<212> TYPE: PRT
<213> ORGANISM: Artificial Sequence
<220> FEATURE:
<223> OTHER INFORMATION: polymer cassette

<400> SEQUENCE: 6

Ser Ser Ala Ser Ser Ser Ala Ala Ser Ser Ala Ser Ser Ser Ser
1               5                  10                 15

Ala Ser Ala Ala
            20

<210> SEQ ID NO 7
<211> LENGTH: 20
<212> TYPE: PRT
<213> ORGANISM: Artificial Sequence
<220> FEATURE:
<223> OTHER INFORMATION: polymer cassette

<400> SEQUENCE: 7

Ser Ala Ser Ala Ser Ala Ser Ala Ser Ala Ser Ala Ala Ser Ser Ala
1               5                  10                 15

Ser Ser Ala Ser
            20

<210> SEQ ID NO 8
<211> LENGTH: 20
<212> TYPE: PRT
<213> ORGANISM: Artificial Sequence
<220> FEATURE:
<223> OTHER INFORMATION: polymer cassette

<400> SEQUENCE: 8

Ala Ser Ser Ala Ala Ala Ser Ala Ala Ala Ala Ser Ser Ala Ala Ser
1               5                  10                 15

Ala Ser Ser Ser
            20

<210> SEQ ID NO 9
<211> LENGTH: 20
<212> TYPE: PRT
<213> ORGANISM: Artificial Sequence
<220> FEATURE:
<223> OTHER INFORMATION: polymer cassette

<400> SEQUENCE: 9
```

```
Ala Ser Pro Ala Ala Pro Ala Pro Ala Ser Pro Ala Ala Pro Ala Pro
1               5                   10                  15

Ser Ala Pro Ala
            20

<210> SEQ ID NO 10
<211> LENGTH: 20
<212> TYPE: PRT
<213> ORGANISM: Artificial Sequence
<220> FEATURE:
<223> OTHER INFORMATION: polymer cassette

<400> SEQUENCE: 10

Ala Ala Pro Ala Ser Pro Ala Pro Ala Ala Pro Ser Ala Pro Ala Pro
1               5                   10                  15

Ala Ala Pro Ser
            20

<210> SEQ ID NO 11
<211> LENGTH: 20
<212> TYPE: PRT
<213> ORGANISM: Artificial Sequence
<220> FEATURE:
<223> OTHER INFORMATION: polymer cassette

<400> SEQUENCE: 11

Ala Pro Ser Ser Pro Ser Pro Ser Ala Pro Ser Ser Pro Ser Pro Ala
1               5                   10                  15

Ser Pro Ser Ser
            20

<210> SEQ ID NO 12
<211> LENGTH: 20
<212> TYPE: PRT
<213> ORGANISM: Artificial Sequence
<220> FEATURE:
<223> OTHER INFORMATION: polymer cassette

<400> SEQUENCE: 12

Ser Ser Pro Ser Ala Pro Ser Pro Ser Ser Pro Ala Ser Pro Ser Pro
1               5                   10                  15

Ser Ser Pro Ala
            20

<210> SEQ ID NO 13
<211> LENGTH: 24
<212> TYPE: PRT
<213> ORGANISM: Artificial Sequence
<220> FEATURE:
<223> OTHER INFORMATION: polymer cassette

<400> SEQUENCE: 13

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 14
<211> LENGTH: 20
<212> TYPE: PRT
<213> ORGANISM: Artificial Sequence
<220> FEATURE:
<223> OTHER INFORMATION: polymer cassette

<400> SEQUENCE: 14
```

```
Ala Ser Ala Ala Ala Pro Ala Ala Ala Ser Ala Ala Ala Ser Ala Pro
1               5                   10                  15

Ser Ala Ala Ala
            20

<210> SEQ ID NO 15
<211> LENGTH: 20
<212> TYPE: PRT
<213> ORGANISM: Artificial Sequence
<220> FEATURE:
<223> OTHER INFORMATION: polymer cassette

<400> SEQUENCE: 15

Ser Ala Pro Ser Ser Pro Ser Pro Ser Ala Pro Ser Ser Pro Ser Pro
1               5                   10                  15

Ala Ser Pro Ser
            20
```